US011382614B2

(12) United States Patent
Desai et al.

(10) Patent No.: US 11,382,614 B2
(45) Date of Patent: Jul. 12, 2022

(54) SURGICAL END EFFECTORS

(71) Applicant: Covidien LP, Mansfield, MA (US)

(72) Inventors: Arpan Desai, Hamden, CT (US); Paul C. DiCesare, Easton, CT (US); Danial Ferreira, Shelton, CT (US); Brandon Michael Zalewski, Shelton, CT (US)

(73) Assignee: COVIDIEN LP, Mansfield, MA (US)

( * ) Notice: Subject to any disclaimer, the term of this patent is extended or adjusted under 35 U.S.C. 154(b) by 275 days.

(21) Appl. No.: 16/844,280

(22) Filed: Apr. 9, 2020

(65) Prior Publication Data

US 2020/0245999 A1 Aug. 6, 2020

Related U.S. Application Data

(63) Continuation of application No. 15/678,156, filed on Aug. 16, 2017, now Pat. No. 10,617,409.

(Continued)

(51) Int. Cl.
*A61B 17/34* (2006.01)
*A61B 17/04* (2006.01)
(Continued)

(52) U.S. Cl.
CPC ...... *A61B 17/0469* (2013.01); *A61B 17/3496* (2013.01); *A61B 18/1445* (2013.01);
(Continued)

(58) Field of Classification Search
CPC ............ A61B 17/0469; A61B 17/0493; A61B 17/062; A61B 17/06004; A61B 17/3496; A61B 2017/00367; A61B 2017/0409; A61B 2017/06176; A61B 2017/06014; A61B 18/1445; A61M 2025/0089; A61M 2025/0095

See application file for complete search history.

(56) References Cited

U.S. PATENT DOCUMENTS 3,596,528 A 8/1971 Dittrich et al.
3,866,510 A 2/1975 Eibes et al.
(Continued)

FOREIGN PATENT DOCUMENTS

EP 0374088 A1 6/1990
JP S60129041 A 7/1985
(Continued)

OTHER PUBLICATIONS

European Office Action dated Mar. 25, 2020 corresponding to counterpart Patent Application EP 17197448.8.
(Continued)

*Primary Examiner* — Ryan J. Severson

(57) ABSTRACT

According to an aspect of the present disclosure, an end effector for use with a surgical device is provided. The end effector includes a driver, a clip assembly, a needle assembly, and biasing element. The clip assembly is disposed in mechanical cooperation with the driver. Rotation of the driver results in longitudinal translation of the clip assembly. The needle assembly is selectively engaged with the clip assembly. The biasing element is disposed in mechanical cooperation with the needle assembly and is configured to bias the needle assembly proximally.

20 Claims, 59 Drawing Sheets

Related U.S. Application Data

(60) Provisional application No. 62/410,878, filed on Oct. 21, 2016.

(51) Int. Cl.

| | |
|---|---|
| *A61B 18/14* | (2006.01) |
| *A61B 90/00* | (2016.01) |
| *A61B 17/00* | (2006.01) |
| *A61B 17/06* | (2006.01) |
| *A61B 17/062* | (2006.01) |
| *A61B 17/29* | (2006.01) |

(52) U.S. Cl.
CPC ......... *A61B 17/0493* (2013.01); *A61B 17/062* (2013.01); *A61B 17/29* (2013.01); *A61B 2017/00367* (2013.01); *A61B 2017/00473* (2013.01); *A61B 2017/0409* (2013.01); *A61B 2017/0417* (2013.01); *A61B 2017/0472* (2013.01); *A61B 2017/06176* (2013.01); *A61B 2090/0801* (2016.02)

(56) References Cited

U.S. PATENT DOCUMENTS

| | | |
|---|---|---|
| 4,350,491 A | 9/1982 | Steuer |
| 4,730,726 A | 3/1988 | Holzwarth |
| 4,884,572 A | 12/1989 | Bays et al. |
| 5,085,661 A | 2/1992 | Moss |
| 5,144,942 A | 9/1992 | Decarie et al. |
| 5,156,267 A | 10/1992 | Yates, Jr. et al. |
| 5,171,247 A | 12/1992 | Hughett et al. |
| 5,171,249 A | 12/1992 | Stefanchik et al. |
| 5,176,306 A | 1/1993 | Heimerl et al. |
| 5,207,697 A | 5/1993 | Carusillo et al. |
| 5,228,256 A | 7/1993 | Dreveny |
| 5,236,563 A | 8/1993 | Loh |
| 5,246,441 A | 9/1993 | Ross et al. |
| 5,246,450 A | 9/1993 | Thornton et al. |
| 5,249,583 A | 10/1993 | Mallaby |
| 5,312,023 A | 5/1994 | Green et al. |
| 5,330,487 A | 7/1994 | Thornton et al. |
| 5,344,061 A | 9/1994 | Crainich |
| 5,353,929 A | 10/1994 | Foster |
| 5,356,064 A | 10/1994 | Green et al. |
| 5,381,896 A | 1/1995 | Simons |
| 5,382,254 A | 1/1995 | McGarry et al. |
| 5,398,861 A | 3/1995 | Green |
| 5,403,327 A | 4/1995 | Thornton et al. |
| 5,407,070 A | 4/1995 | Bascos et al. |
| 5,433,721 A | 7/1995 | Hooven et al. |
| 5,439,468 A | 8/1995 | Schulze et al. |
| 5,466,243 A | 11/1995 | Schmieding et al. |
| 5,467,911 A | 11/1995 | Tsuruta et al. |
| 5,474,566 A | 12/1995 | Alesi et al. |
| 5,474,567 A | 12/1995 | Stefanchik et al. |
| 5,522,844 A | 6/1996 | Johnson |
| 5,527,319 A | 6/1996 | Green et al. |
| 5,553,765 A | 9/1996 | Knodel et al. |
| 5,562,685 A | 10/1996 | Mollenauer et al. |
| 5,564,615 A | 10/1996 | Bishop et al. |
| 5,582,615 A | 12/1996 | Foshee et al. |
| 5,582,616 A | 12/1996 | Bolduc et al. |
| 5,584,425 A | 12/1996 | Savage et al. |
| 5,588,581 A | 12/1996 | Conlon et al. |
| 5,601,571 A | 2/1997 | Moss |
| 5,601,573 A | 2/1997 | Fogelberg et al. |
| 5,607,436 A | 3/1997 | Pratt et al. |
| 5,626,613 A | 5/1997 | Schmieding |
| 5,628,752 A | 5/1997 | Asnis et al. |
| 5,649,931 A | 7/1997 | Bryant et al. |
| 5,662,662 A | 9/1997 | Bishop et al. |
| 5,681,330 A | 10/1997 | Hughett et al. |
| 5,683,401 A | 11/1997 | Schmieding et al. |
| 5,685,474 A | 11/1997 | Seeber |
| 5,697,935 A | 12/1997 | Moran et al. |
| 5,702,420 A | 12/1997 | Sterling et al. |
| 5,704,534 A | 1/1998 | Huitema et al. |
| 5,709,692 A | 1/1998 | Mollenauer et al. |
| 5,728,116 A | 3/1998 | Rosenman |
| 5,730,744 A | 3/1998 | Justin et al. |
| 5,732,806 A | 3/1998 | Foshee et al. |
| 5,735,854 A | 4/1998 | Caron et al. |
| 5,741,268 A | 4/1998 | Schutz |
| 5,762,255 A | 6/1998 | Chrisman et al. |
| 5,782,844 A | 7/1998 | Yoon et al. |
| 5,792,165 A | 8/1998 | Klieman et al. |
| 5,810,882 A | 9/1998 | Bolduc et al. |
| 5,824,008 A | 10/1998 | Bolduc et al. |
| 5,830,221 A | 11/1998 | Stein et al. |
| 5,843,087 A | 12/1998 | Jensen et al. |
| 5,897,564 A | 4/1999 | Schulze et al. |
| 5,904,693 A | 5/1999 | Dicesare et al. |
| 5,910,105 A | 6/1999 | Swain et al. |
| 5,911,722 A | 6/1999 | Adler et al. |
| 5,928,244 A | 7/1999 | Tovey et al. |
| 5,928,252 A | 7/1999 | Steadman et al. |
| 5,931,844 A | 8/1999 | Thompson et al. |
| 5,941,439 A | 8/1999 | Kammerer et al. |
| 5,954,259 A | 9/1999 | Viola et al. |
| 5,961,524 A | 10/1999 | Crombie |
| 5,964,772 A | 10/1999 | Bolduc et al. |
| 5,976,160 A | 11/1999 | Crainich |
| 5,997,552 A | 12/1999 | Person et al. |
| 6,010,513 A | 1/2000 | Tormala et al. |
| 6,013,991 A | 1/2000 | Philipp |
| 6,039,753 A | 3/2000 | Meislin |
| 6,074,395 A | 6/2000 | Trott et al. |
| 6,099,537 A | 8/2000 | Sugai et al. |
| 6,126,670 A | 10/2000 | Walker et al. |
| 6,132,435 A | 10/2000 | Young |
| 6,146,387 A | 11/2000 | Trott et al. |
| 6,183,479 B1 | 2/2001 | Tormala et al. |
| 6,228,098 B1 | 5/2001 | Kayan et al. |
| 6,235,058 B1 | 5/2001 | Huene |
| 6,241,736 B1 | 6/2001 | Sater et al. |
| 6,261,302 B1 | 7/2001 | Voegele et al. |
| 6,296,656 B1 | 10/2001 | Bolduc et al. |
| 6,330,964 B1 | 12/2001 | Kayan et al. |
| 6,387,113 B1 | 5/2002 | Hawkins et al. |
| 6,402,701 B1 * | 6/2002 | Kaplan ............. A61B 10/0233 600/567 |
| 6,402,757 B1 | 6/2002 | Moore, III et al. |
| 6,402,780 B2 | 6/2002 | Williamson, IV et al. |
| 6,425,900 B1 | 7/2002 | Knodel et al. |
| 6,439,446 B1 | 8/2002 | Perry et al. |
| 6,440,136 B1 | 8/2002 | Gambale et al. |
| 6,450,391 B1 | 9/2002 | Kayan et al. |
| 6,457,625 B1 | 10/2002 | Tormala et al. |
| 6,551,333 B2 | 4/2003 | Kuhns et al. |
| 6,562,051 B1 | 5/2003 | Bolduc et al. |
| 6,572,563 B2 * | 6/2003 | Ouchi ............... A61B 10/0275 600/564 |
| 6,572,626 B1 | 6/2003 | Knodel et al. |
| 6,579,300 B2 * | 6/2003 | Griego .......... A61B 17/320016 606/167 |
| 6,589,249 B2 | 7/2003 | Sater et al. |
| 6,592,593 B1 | 7/2003 | Parodi et al. |
| 6,626,916 B1 | 9/2003 | Yeung et al. |
| 6,632,228 B2 | 10/2003 | Fortier et al. |
| 6,652,538 B2 | 11/2003 | Kayan et al. |
| 6,663,656 B2 | 12/2003 | Schmieding et al. |
| 6,666,854 B1 | 12/2003 | Lange |
| 6,695,867 B2 | 2/2004 | Ginn et al. |
| 6,733,506 B1 | 5/2004 | McDevitt et al. |
| 6,743,240 B2 | 6/2004 | Smith et al. |
| 6,749,621 B2 | 6/2004 | Pantages et al. |
| 6,755,836 B1 | 6/2004 | Lewis |
| 6,773,438 B1 | 8/2004 | Knodel et al. |
| 6,800,081 B2 | 10/2004 | Parodi |
| 6,811,552 B2 | 11/2004 | Weil, Sr. et al. |
| 6,824,548 B2 | 11/2004 | Smith et al. |
| 6,837,893 B2 | 1/2005 | Miller |
| 6,840,943 B2 | 1/2005 | Kennefick et al. |

(56) References Cited

U.S. PATENT DOCUMENTS

| | | | |
|---|---|---|---|
| 6,843,794 B2 | 1/2005 | Sixto, Jr. et al. |
| 6,869,435 B2 | 3/2005 | Blake, III |
| 6,884,248 B2 | 4/2005 | Bolduc et al. |
| 6,887,244 B1 | 5/2005 | Walker et al. |
| 6,893,446 B2 | 5/2005 | Sater et al. |
| 6,905,057 B2 | 6/2005 | Swayze et al. |
| 6,929,661 B2 | 8/2005 | Bolduc et al. |
| 6,942,674 B2 | 9/2005 | Belef et al. |
| 6,945,979 B2 | 9/2005 | Kortenbach et al. |
| 6,960,217 B2 | 11/2005 | Bolduc |
| 6,966,919 B2 | 11/2005 | Sixto, Jr. et al. |
| 6,988,650 B2 | 1/2006 | Schwemberger et al. |
| 7,000,819 B2 | 2/2006 | Swayze et al. |
| 7,070,601 B2 | 7/2006 | Culbert et al. |
| 7,122,028 B2 | 10/2006 | Looper et al. |
| 7,128,754 B2 | 10/2006 | Bolduc |
| 7,147,657 B2 | 12/2006 | Chiang et al. |
| 7,204,847 B1 | 4/2007 | Gambale |
| 7,261,716 B2 | 8/2007 | Strobel et al. |
| 7,357,287 B2 | 4/2008 | Shelton, IV et al. |
| 7,380,696 B2 | 6/2008 | Shelton, IV et al. |
| 7,404,508 B2 | 7/2008 | Smith et al. |
| 7,410,086 B2 | 8/2008 | Ortiz et al. |
| 7,434,717 B2 | 10/2008 | Shelton, IV et al. |
| 7,461,574 B2 | 12/2008 | Lewis et al. |
| 7,491,232 B2 | 2/2009 | Bolduc et al. |
| 7,544,198 B2 | 6/2009 | Parodi |
| 7,591,842 B2 | 9/2009 | Parodi |
| 7,611,521 B2 | 11/2009 | Lubbers et al. |
| 7,637,905 B2 | 12/2009 | Saadat et al. |
| 7,637,932 B2 | 12/2009 | Bolduc et al. |
| 7,670,362 B2 | 3/2010 | Zergiebel |
| 7,740,159 B2 | 6/2010 | Shelton, IV et al. |
| 7,758,591 B2 * | 7/2010 | Griego | A61B 17/32056 606/113 |
| 7,758,612 B2 | 7/2010 | Shipp |
| 7,811,312 B2 | 10/2010 | Stevens et al. |
| 7,819,884 B2 | 10/2010 | Lee et al. |
| 7,823,267 B2 | 11/2010 | Bolduc |
| 7,824,376 B2 * | 11/2010 | Fujisaki | A61B 17/3478 600/106 |
| 7,828,838 B2 | 11/2010 | Bolduc et al. |
| 7,862,573 B2 | 1/2011 | Darois et al. |
| 7,867,252 B2 | 1/2011 | Criscuolo et al. |
| 7,905,890 B2 | 3/2011 | Whitfield et al. |
| 7,913,892 B2 | 3/2011 | Cole et al. |
| 7,922,061 B2 | 4/2011 | Shelton, IV et al. |
| 7,922,063 B2 | 4/2011 | Zemlok et al. |
| 7,931,660 B2 | 4/2011 | Aranyi et al. |
| 7,959,663 B2 | 6/2011 | Bolduc |
| 7,959,670 B2 | 6/2011 | Bolduc |
| 8,002,811 B2 | 8/2011 | Corradi et al. |
| 8,006,365 B2 | 8/2011 | Levin et al. |
| 8,034,076 B2 | 10/2011 | Criscuolo et al. |
| 8,062,306 B2 | 11/2011 | Nobis et al. |
| 8,075,570 B2 | 12/2011 | Bolduc et al. |
| 8,083,752 B2 | 12/2011 | Bolduc |
| 8,087,142 B2 | 1/2012 | Levin et al. |
| 8,092,519 B2 | 1/2012 | Bolduc |
| 8,114,099 B2 | 2/2012 | Shipp |
| 8,114,101 B2 | 2/2012 | Criscuolo et al. |
| 8,152,820 B2 | 4/2012 | Mohamed et al. |
| 8,167,815 B2 * | 5/2012 | Parihar | A61B 10/0275 600/564 |
| 8,181,840 B2 | 5/2012 | Milliman |
| 8,216,254 B2 | 7/2012 | McLean et al. |
| 8,216,272 B2 | 7/2012 | Shipp |
| 8,231,639 B2 | 7/2012 | Bolduc et al. |
| 8,282,670 B2 | 10/2012 | Shipp |
| 8,292,933 B2 | 10/2012 | Zergiebel |
| 8,323,314 B2 | 12/2012 | Blier |
| 8,328,823 B2 | 12/2012 | Aranyi et al. |
| 8,333,776 B2 | 12/2012 | Cheng et al. |
| 8,343,176 B2 | 1/2013 | Criscuolo et al. |
| 8,343,184 B2 | 1/2013 | Blier |
| 8,377,044 B2 | 2/2013 | Coe et al. |
| 8,382,773 B2 | 2/2013 | Whitfield et al. |
| 8,382,778 B2 | 2/2013 | Criscuolo et al. |
| 8,388,629 B2 * | 3/2013 | Griego | A61B 17/32056 606/113 |
| 8,414,627 B2 | 4/2013 | Corradi et al. |
| 8,424,740 B2 | 4/2013 | Shelton, IV et al. |
| 8,465,520 B2 | 6/2013 | Blier |
| 8,474,679 B2 | 7/2013 | Felix |
| 8,579,919 B2 | 11/2013 | Bolduc et al. |
| 8,579,920 B2 | 11/2013 | Nering et al. |
| 8,597,311 B2 | 12/2013 | Criscuolo et al. |
| 8,603,135 B2 | 12/2013 | Mueller |
| 8,672,209 B2 | 3/2014 | Crainich |
| 8,684,247 B2 | 4/2014 | Scirica et al. |
| 8,685,044 B2 | 4/2014 | Bolduc et al. |
| 8,690,889 B2 | 4/2014 | Colesanti et al. |
| 8,690,897 B2 | 4/2014 | Bolduc |
| 8,728,098 B2 | 5/2014 | Daniel et al. |
| 8,728,099 B2 | 5/2014 | Cohn et al. |
| 8,728,100 B2 * | 5/2014 | Daniel | A61B 17/0469 606/144 |
| 8,728,102 B2 | 5/2014 | Criscuolo et al. |
| 8,728,120 B2 | 5/2014 | Blier |
| 8,771,288 B2 * | 7/2014 | Griego | A61B 17/32056 606/113 |
| 8,777,969 B2 | 7/2014 | Kayan |
| 8,821,514 B2 | 9/2014 | Aranyi |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 8,894,669 B2 | 11/2014 | Nering et al. |
| 8,920,439 B2 | 12/2014 | Cardinale et al. |
| 8,926,637 B2 | 1/2015 | Zergiebel |
| 9,017,345 B2 | 4/2015 | Taylor et al. |
| 9,023,065 B2 | 5/2015 | Bolduc et al. |
| 9,028,495 B2 | 5/2015 | Mueller et al. |
| 9,101,385 B2 * | 8/2015 | Shelton, IV | A61B 34/37 |
| 9,186,138 B2 | 11/2015 | Corradi et al. |
| 9,259,221 B2 | 2/2016 | Zergiebel |
| 9,282,961 B2 | 3/2016 | Whitman et al. |
| 9,332,983 B2 | 5/2016 | Shipp |
| 9,345,462 B2 | 5/2016 | Weitzner et al. |
| 9,351,728 B2 | 5/2016 | Sniffin et al. |
| 9,351,733 B2 | 5/2016 | Fischvogt |
| 9,358,004 B2 | 6/2016 | Sniffin et al. |
| 9,358,010 B2 | 6/2016 | Wenchell et al. |
| 9,364,231 B2 | 6/2016 | Wenchell |
| 9,364,274 B2 | 6/2016 | Zergiebel |
| 9,386,983 B2 | 7/2016 | Swensgard et al. |
| 9,402,623 B2 | 8/2016 | Kayan |
| 9,445,814 B2 | 9/2016 | Ranucci et al. |
| 9,480,818 B2 * | 11/2016 | Hollett | A61M 25/0069 |
| 9,486,218 B2 | 11/2016 | Criscuolo et al. |
| 9,526,498 B2 | 12/2016 | Reed |
| 9,615,830 B2 | 4/2017 | Ranucci et al. |
| 9,655,621 B2 | 5/2017 | Abuzaina et al. |
| 9,655,686 B2 * | 5/2017 | Lee | A61B 90/11 |
| 9,662,106 B2 | 5/2017 | Corradi et al. |
| 9,668,730 B2 | 6/2017 | Sniffin et al. |
| 9,730,727 B2 * | 8/2017 | Sato | A61B 10/04 |
| 9,783,329 B2 | 10/2017 | Sniffin et al. |
| 9,788,833 B2 | 10/2017 | Zergiebel et al. |
| 9,826,972 B2 * | 11/2017 | Ranucci | A61B 17/0401 |
| 9,924,938 B2 * | 3/2018 | Ziniti | A61B 17/0469 |
| 10,058,309 B2 * | 8/2018 | Hatta | A61B 10/0283 |
| 10,085,746 B2 | 10/2018 | Fischvogt |
| 10,232,146 B2 * | 3/2019 | Braithwaite | A61M 25/0631 |
| 10,617,409 B2 | 4/2020 | Desai et al. |
| 10,743,859 B2 * | 8/2020 | Desai | A61B 17/06066 |
| 2001/0005778 A1 * | 6/2001 | Ouchi | A61B 10/0275 606/171 |
| 2002/0095168 A1 * | 7/2002 | Griego | A61B 17/320016 606/167 |
| 2003/0009441 A1 | 1/2003 | Holsten et al. |
| 2004/0015177 A1 | 1/2004 | Chu |
| 2004/0092937 A1 | 5/2004 | Criscuolo et al. |
| 2005/0222665 A1 | 10/2005 | Aranyi |
| 2006/0129152 A1 | 6/2006 | Shipp |

(56) References Cited

U.S. PATENT DOCUMENTS

| | | | |
|---|---|---|---|
| 2006/0173413 A1* | 8/2006 | Fan | A61M 25/0631 604/164.04 |
| 2007/0038220 A1 | 2/2007 | Shipp | |
| 2007/0088390 A1 | 4/2007 | Paz et al. | |
| 2007/0106317 A1 | 5/2007 | Shelton et al. | |
| 2007/0162030 A1 | 7/2007 | Aranyi et al. | |
| 2008/0097523 A1 | 4/2008 | Bolduc et al. | |
| 2008/0312687 A1 | 12/2008 | Blier | |
| 2009/0043258 A1* | 2/2009 | Fujisaki | A61M 25/0084 600/106 |
| 2009/0112234 A1 | 4/2009 | Crainich et al. | |
| 2009/0118776 A1 | 5/2009 | Kelsch et al. | |
| 2009/0131872 A1 | 5/2009 | Popov | |
| 2009/0216154 A1 | 8/2009 | Lin Lee | |
| 2010/0270354 A1 | 10/2010 | Rimer et al. | |
| 2011/0022065 A1 | 1/2011 | Shipp | |
| 2011/0224575 A1* | 9/2011 | Carrillo, Jr. | A61B 10/0233 604/272 |
| 2011/0295282 A1 | 12/2011 | Glick et al. | |
| 2012/0059397 A1 | 3/2012 | Criscuolo et al. | |
| 2012/0109157 A1 | 5/2012 | Criscuolo et al. | |
| 2012/0323261 A1 | 12/2012 | Gaynor et al. | |
| 2013/0116709 A1 | 5/2013 | Ziniti et al. | |
| 2014/0005678 A1 | 1/2014 | Shelton, IV et al. | |
| 2014/0014707 A1 | 1/2014 | Onukuri et al. | |
| 2014/0200587 A1 | 7/2014 | Pompee et al. | |
| 2014/0243855 A1 | 8/2014 | Sholev et al. | |
| 2014/0276967 A1 | 9/2014 | Fischvogt et al. | |
| 2015/0032130 A1 | 1/2015 | Russo | |
| 2015/0133970 A1 | 5/2015 | Ranucci et al. | |
| 2015/0150558 A1 | 6/2015 | Zergiebel | |
| 2015/0289857 A1* | 10/2015 | Hatta | A61B 10/0283 600/563 |
| 2015/0327859 A1 | 11/2015 | Bolduc | |
| 2016/0007991 A1 | 1/2016 | Bolduc | |
| 2016/0007996 A1 | 1/2016 | Bolduc | |
| 2016/0045222 A1 | 2/2016 | Lee | |
| 2016/0074034 A1 | 3/2016 | Shipp | |
| 2016/0166255 A1 | 6/2016 | Fischvogt | |
| 2016/0249912 A1 | 9/2016 | Fischvogt | |
| 2016/0270778 A1 | 9/2016 | Zergiebel | |
| 2016/0270835 A1 | 9/2016 | Reed | |
| 2016/0278766 A1 | 9/2016 | Wenchell et al. | |
| 2016/0302824 A1* | 10/2016 | Sato | A61B 17/3478 |
| 2016/0338694 A1 | 11/2016 | Kayan | |
| 2016/0345967 A1 | 12/2016 | Sniffin et al. | |
| 2018/0110510 A1* | 4/2018 | Desai | A61B 17/0401 |
| 2018/0110512 A1* | 4/2018 | Desai | A61B 17/0491 |
| 2020/0245999 A1* | 8/2020 | Desai | A61B 17/0469 |

FOREIGN PATENT DOCUMENTS

| | | |
|---|---|---|
| JP | 09149906 | 6/1997 |
| WO | 9316644 A1 | 9/1993 |
| WO | 03037194 A1 | 5/2003 |

OTHER PUBLICATIONS

Extended European Search Report corresponding to counterpart EP Appln. No. 17 19 7448.8 dated May 15, 2018.

Partial European Search Report corresponding to counterpart European Patent Appln. No. EP 17 19 7448.8 dated Jan. 12, 2018.

Extended European Search Report corresponding to EP 14 15 8946.5, completed Jun. 20, 2014 and dated Jul. 8, 2014; (9 pp).

Extended European Search Report corresponding to EP 14 17 8107.0, completed Nov. 24, 2014 and dated Dec. 3, 2014; (5 pp).

Extended European Search Report corresponding to EP 14 17 4656.0, completed Jan. 16, 2015 and dated Jan. 26, 2015; (7 pp).

Extended European Search Report corresponding to EP 14 18 4907.5, completed Jan. 12, 2015 and dated Jan. 27, 2015; (9 pp).

EP Search Report corresponding to EP 14 18 1900.3, completed Mar. 31, 2015 and dated Apr. 9, 2015; 7pp.

Extended European Search Report corresponding to counterpart application EP 14 19 7885.8 dated Apr. 30, 2015; 9pp.

Extended European Search Report corresponding to EP No. 11 25 0549.0, completed Sep. 9, 2013 and dated Sep. 17, 2013; 9 pages.

Extended European Search Report corresponding to EP 14 15 9394.7, completed Apr. 16, 2014 and dated Apr. 29, 2014; 8 pages.

European Search Report corresponding to EP No. 10 01 2659.8, completed Dec. 21, 2010; dated Jan. 3, 2011; 3 pages.

European Search Report corresponding to Ep No. 10 01 2646.5, completed Feb. 11, 2011; dated Feb. 22, 2011.

Extended European Search Report corresponding to Int'l Application No. EP 14 15 1663.3 dated Jun. 7, 2016.

Supplementary European Search Report dated Feb. 2, 2017 in corresponding European Patent Application No. 14817036, 8 pages.

European Search Report dated May 10, 2017 in corresponding European Patent Application No. 17157259.7, 12 pages.

Extended European Search Report corresponding to counterpart Patent Appln. EP 17 19 7477.7 dated Jul. 23, 2018.

Extended European Search Report corresponding to counterpart European Patent Appln. No. EP 17 19 7455.3 dated Jan. 17, 2018.

* cited by examiner

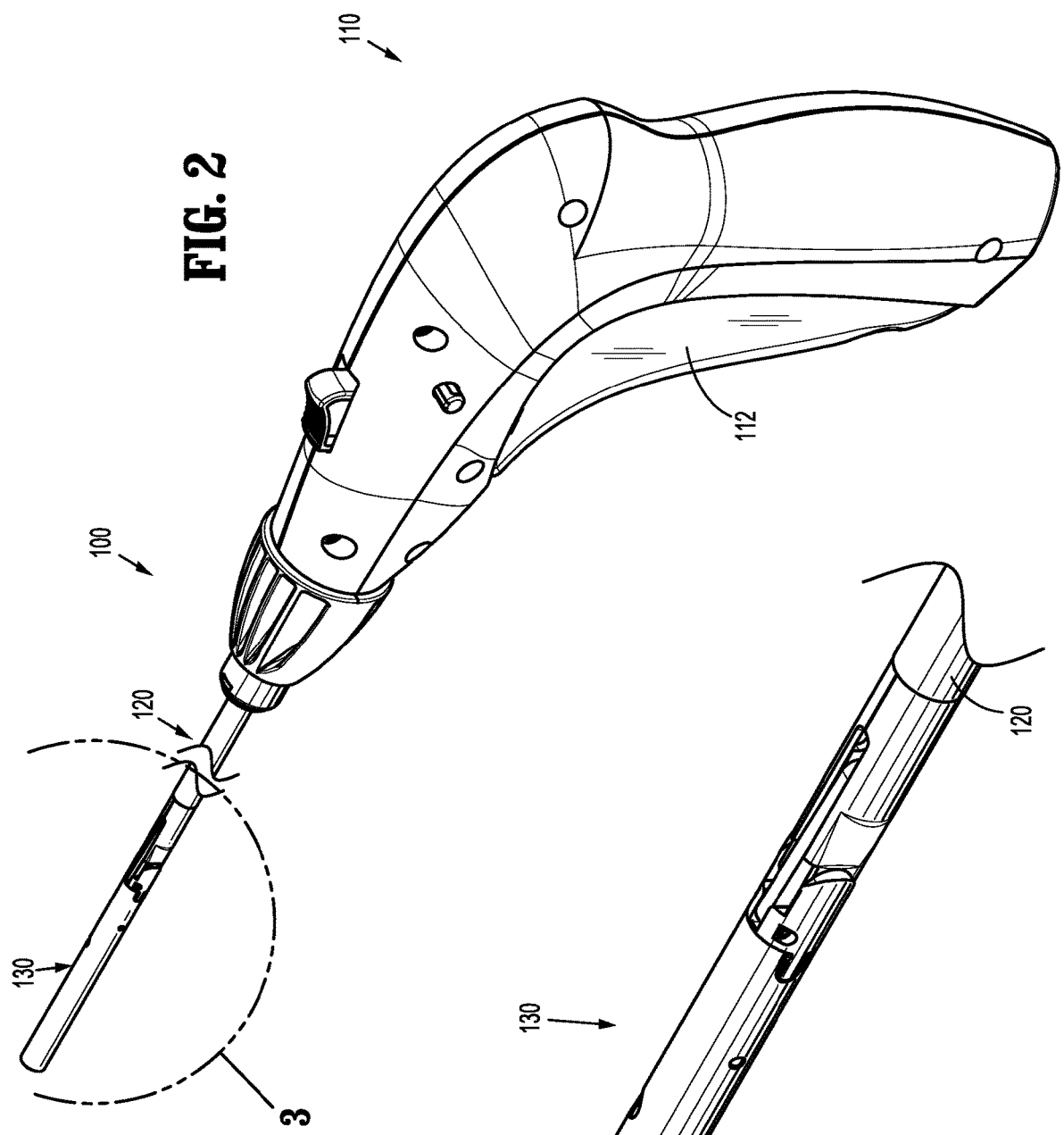

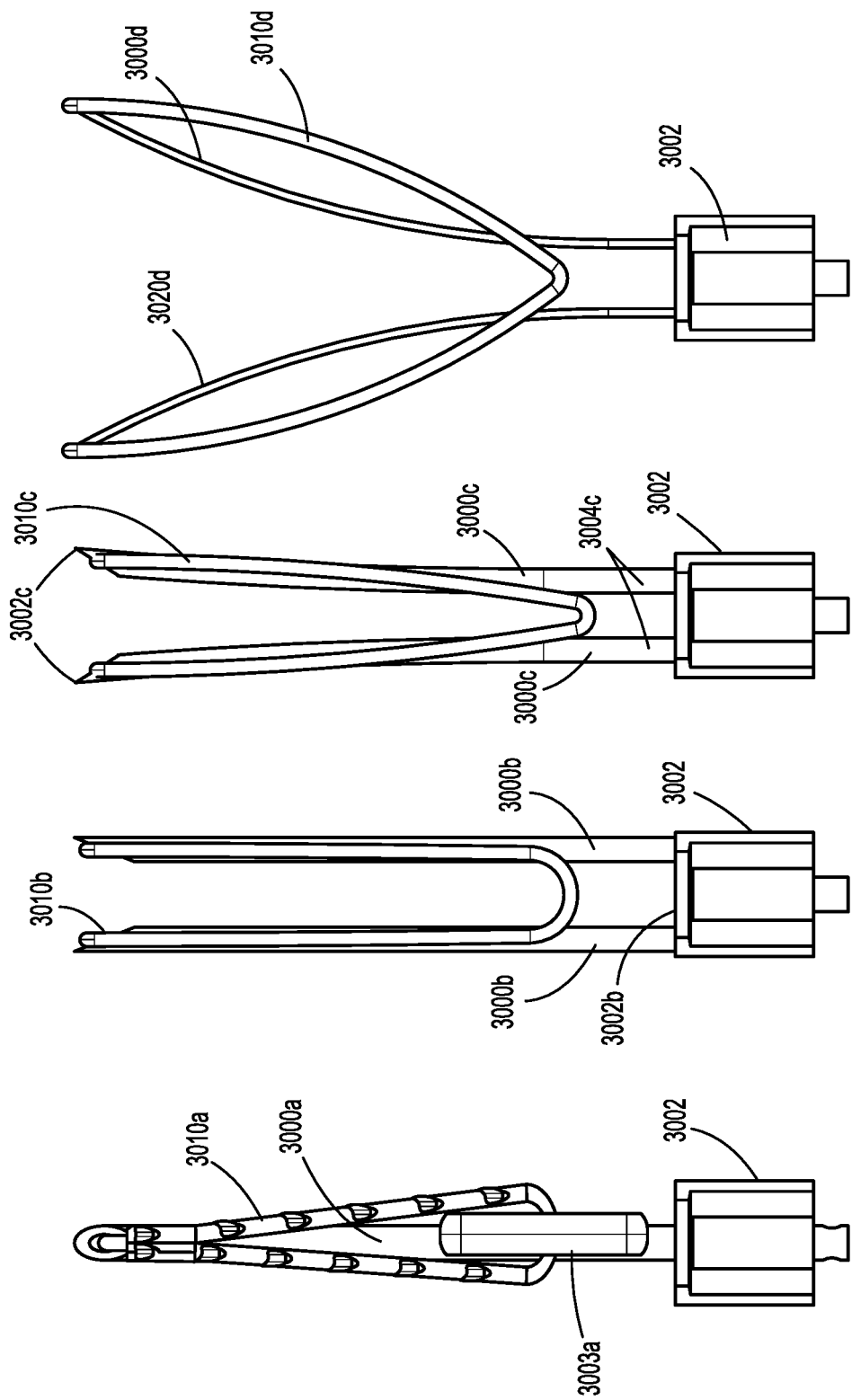

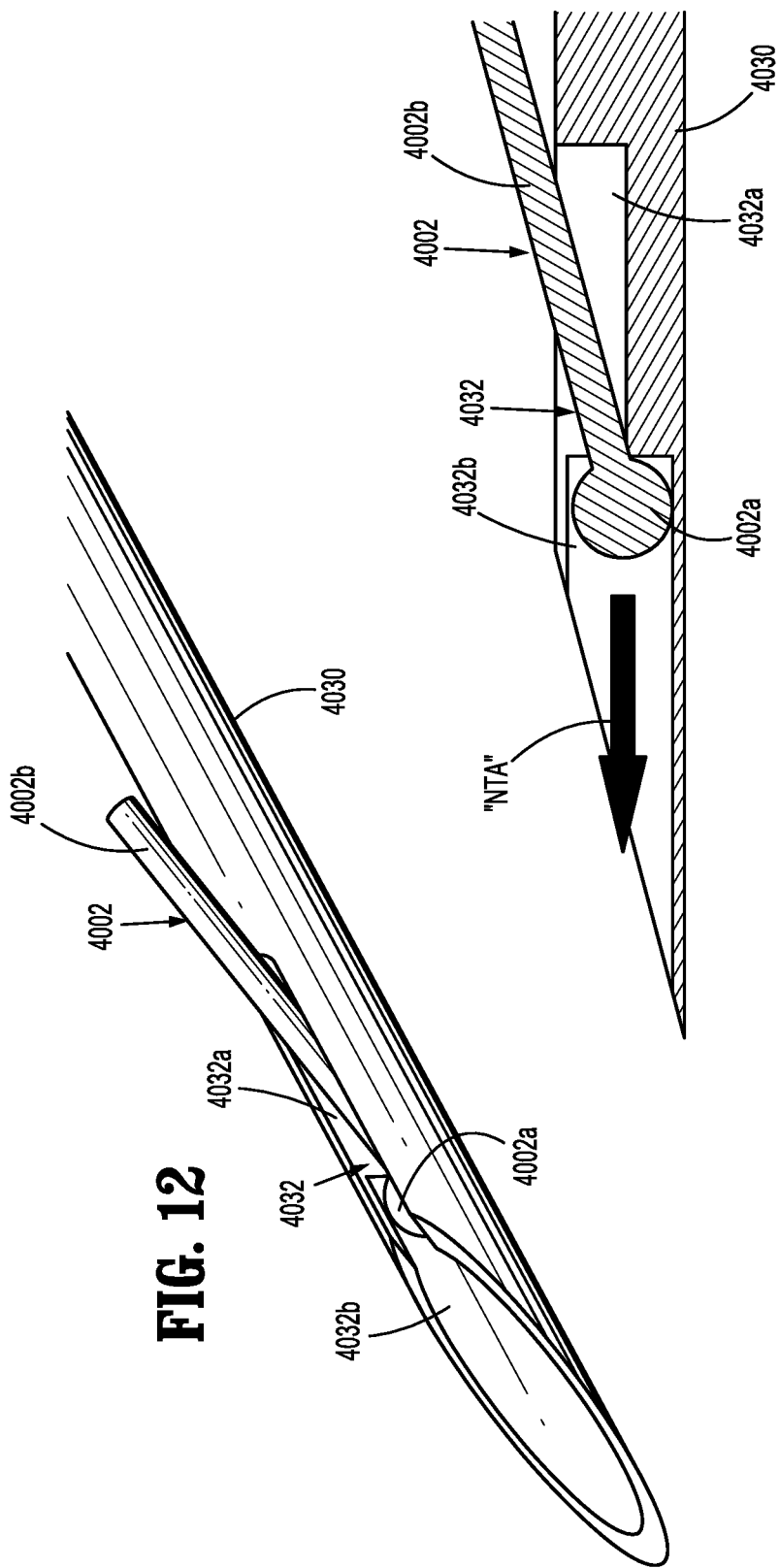

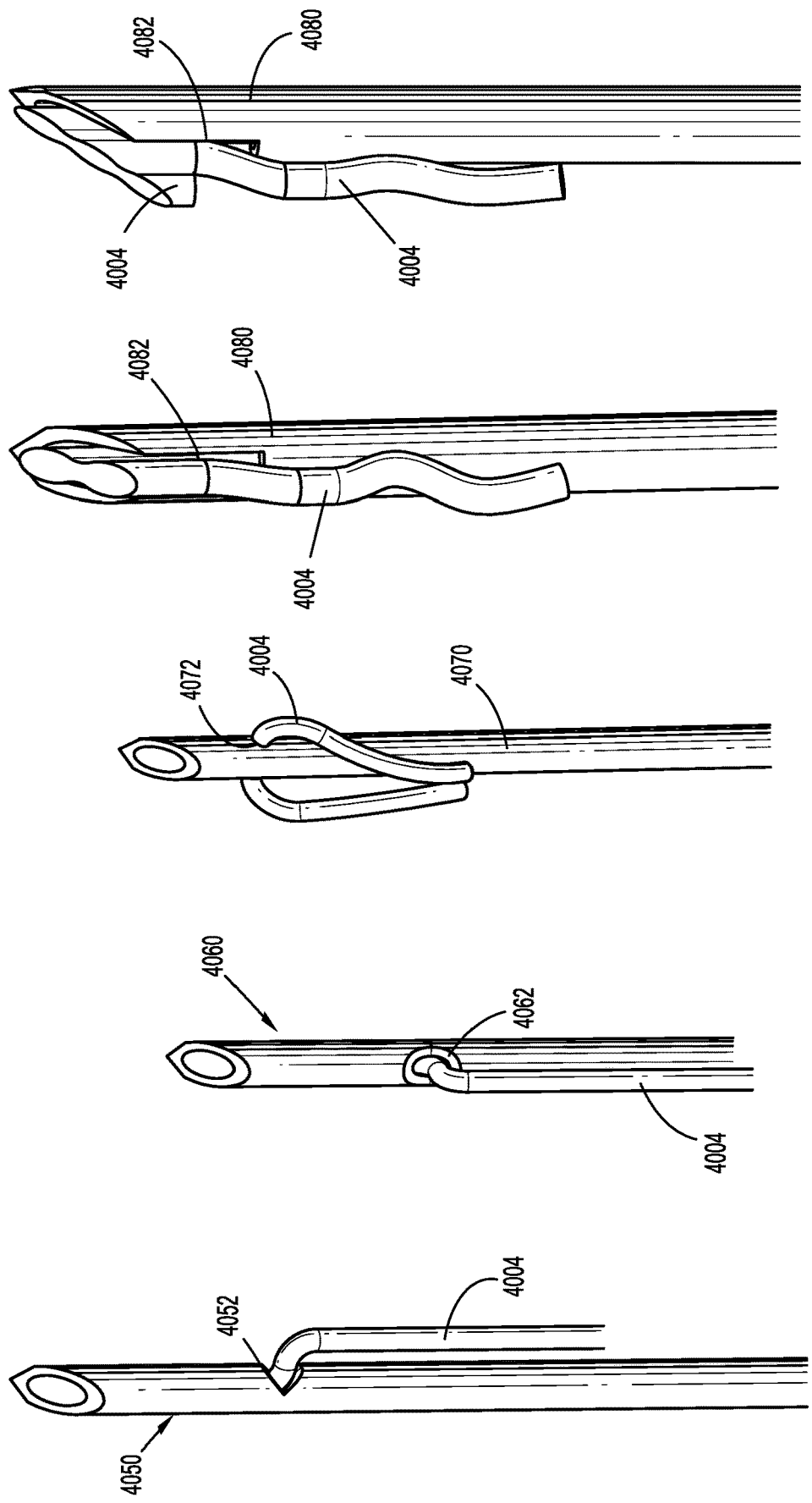

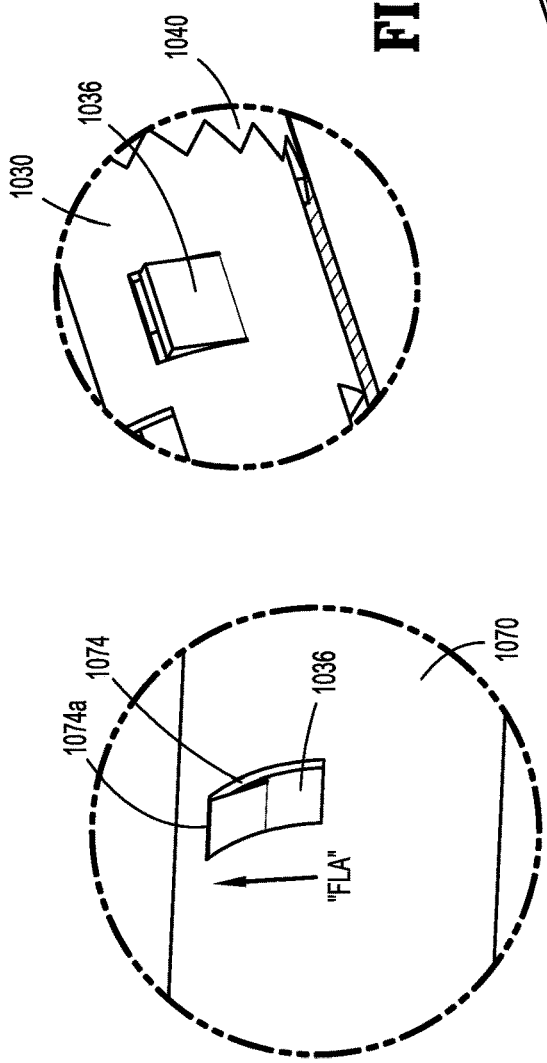
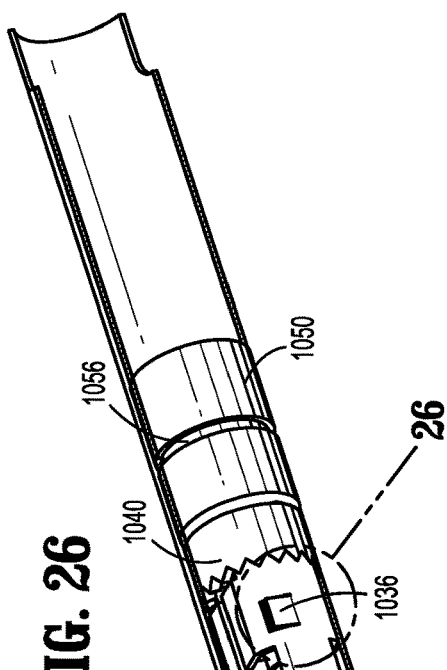
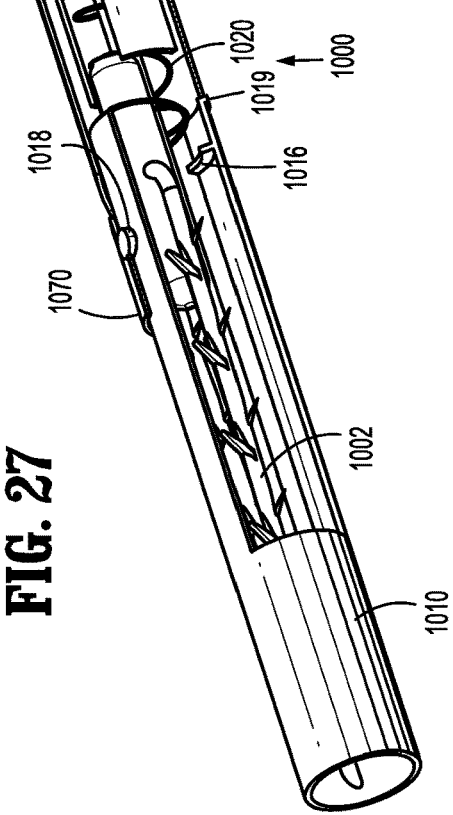

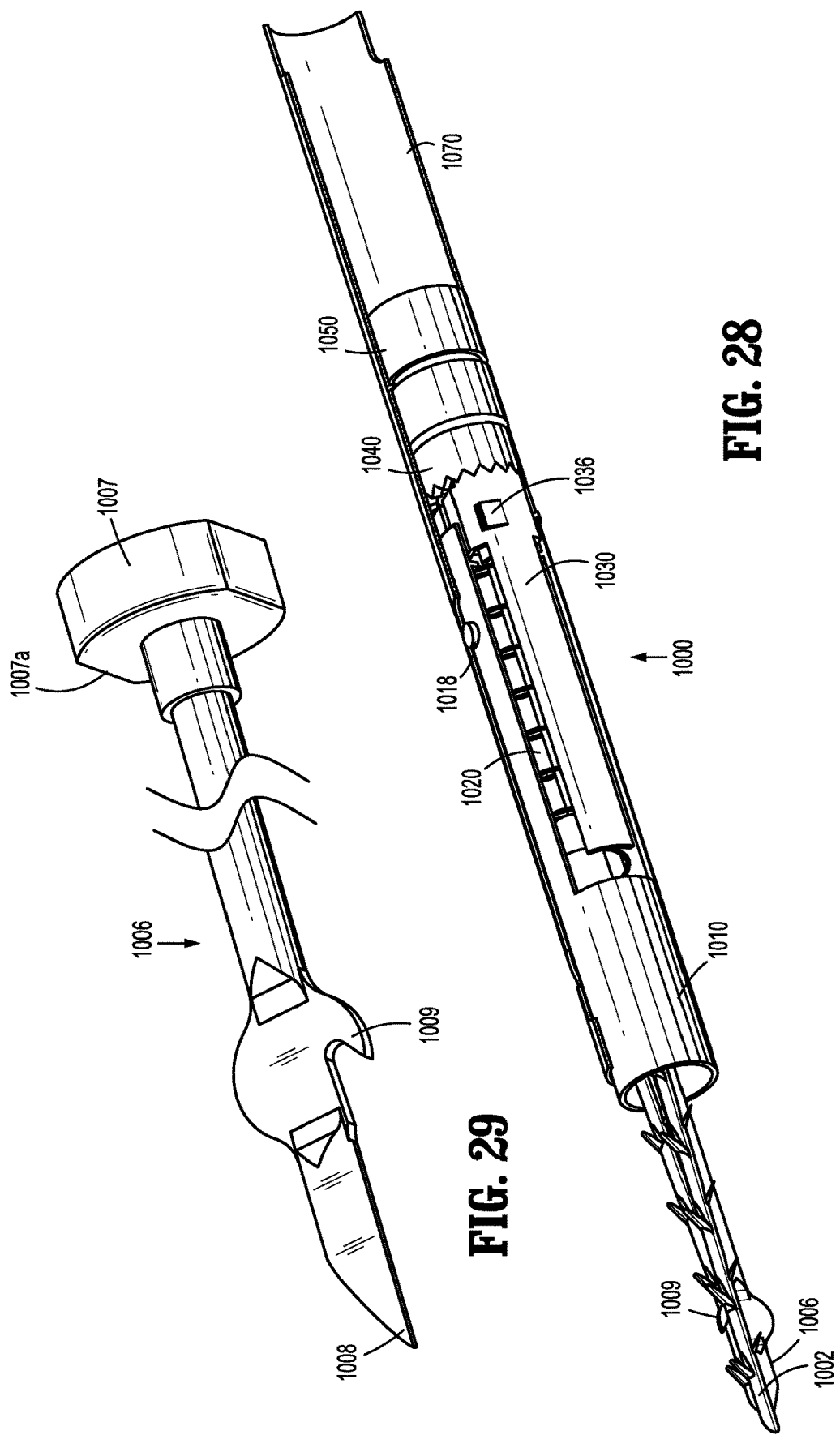

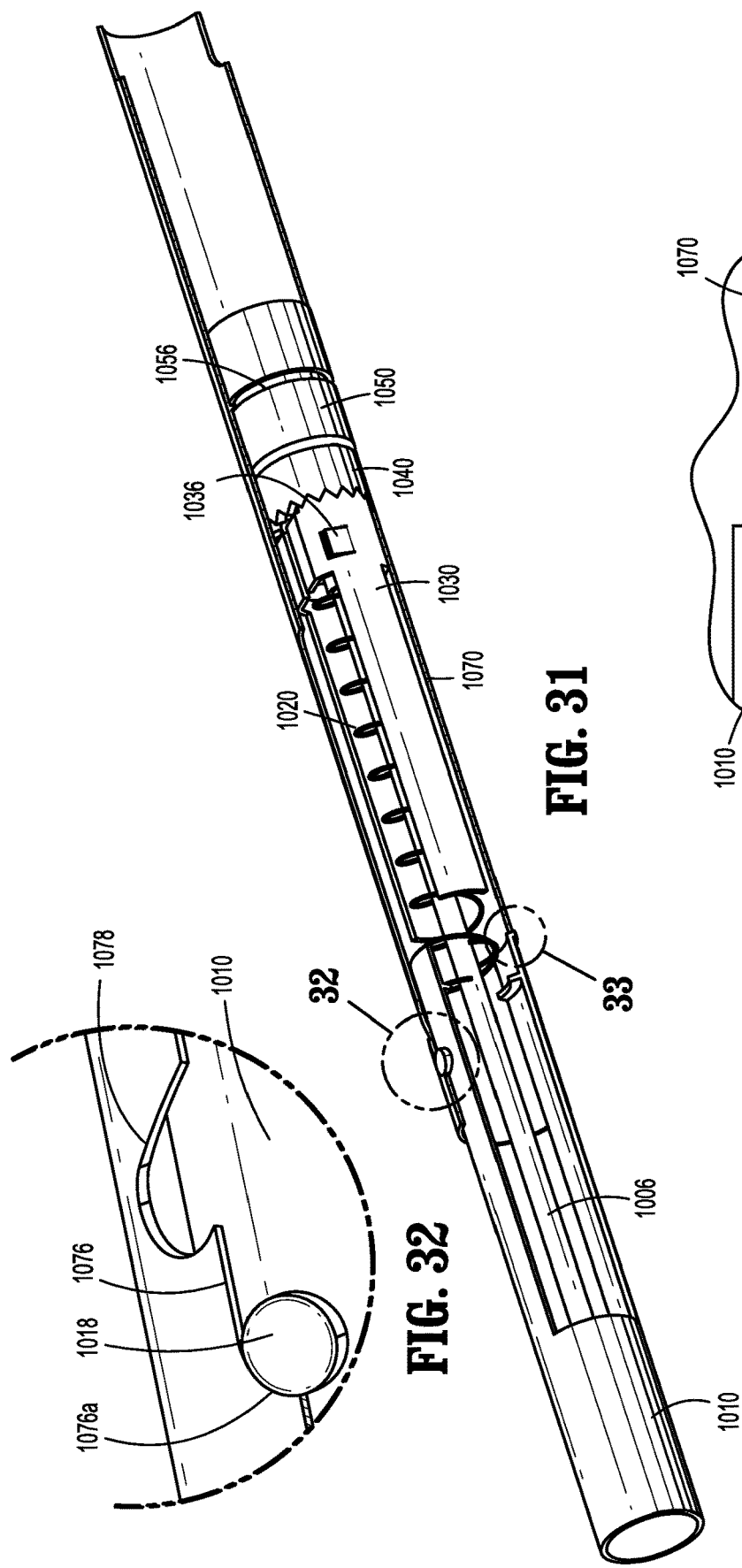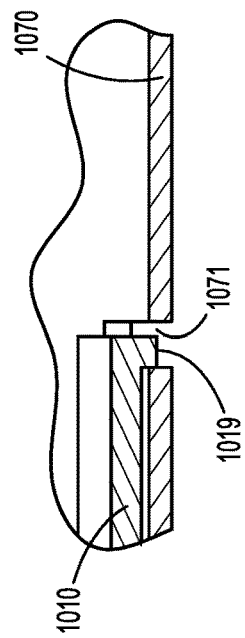

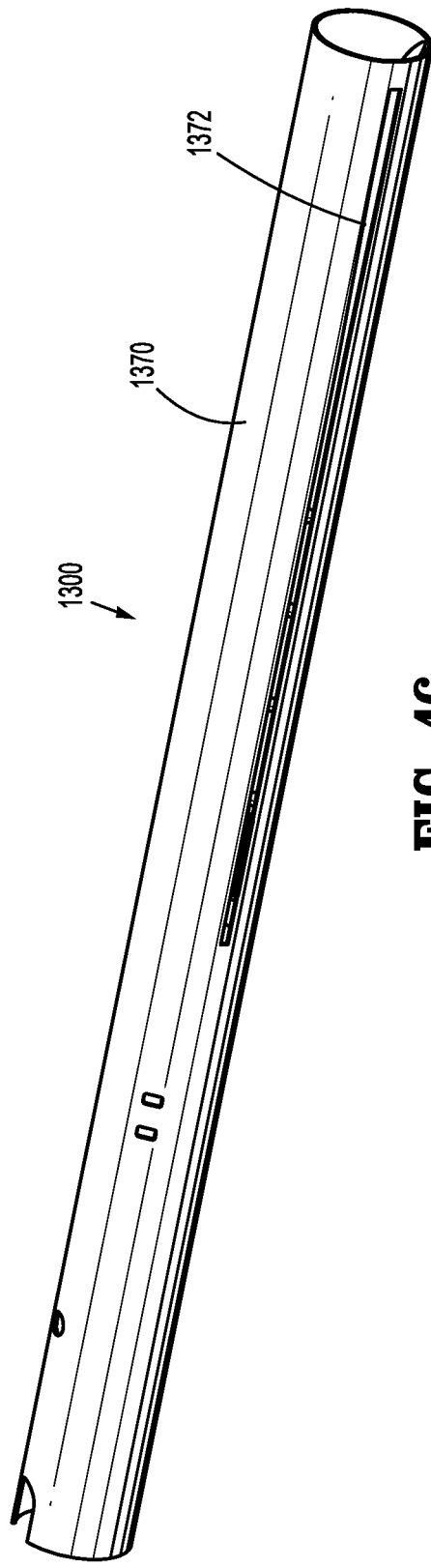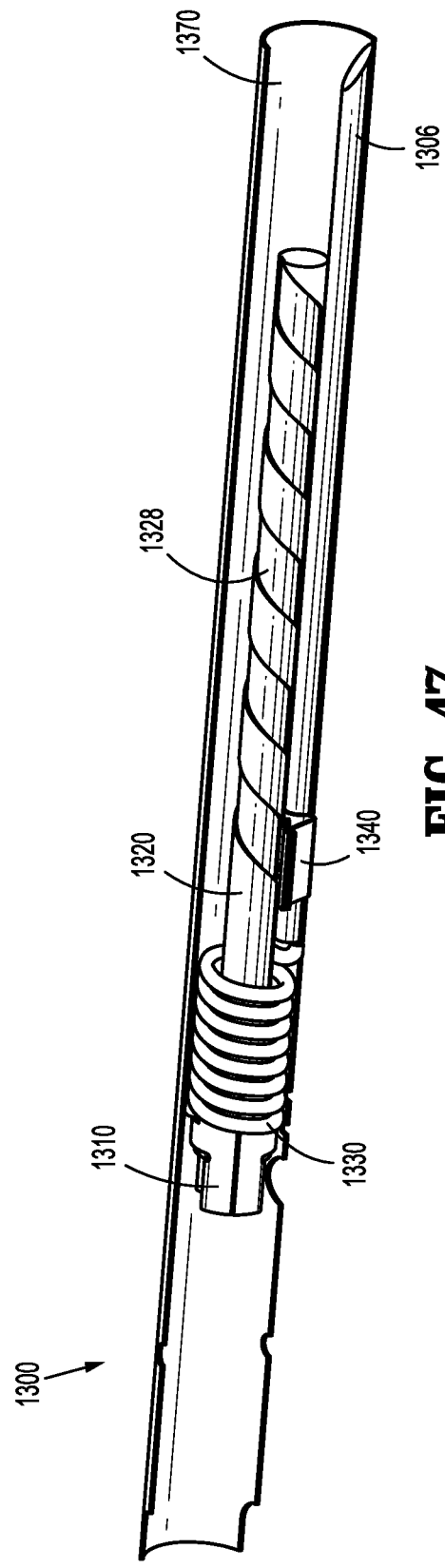

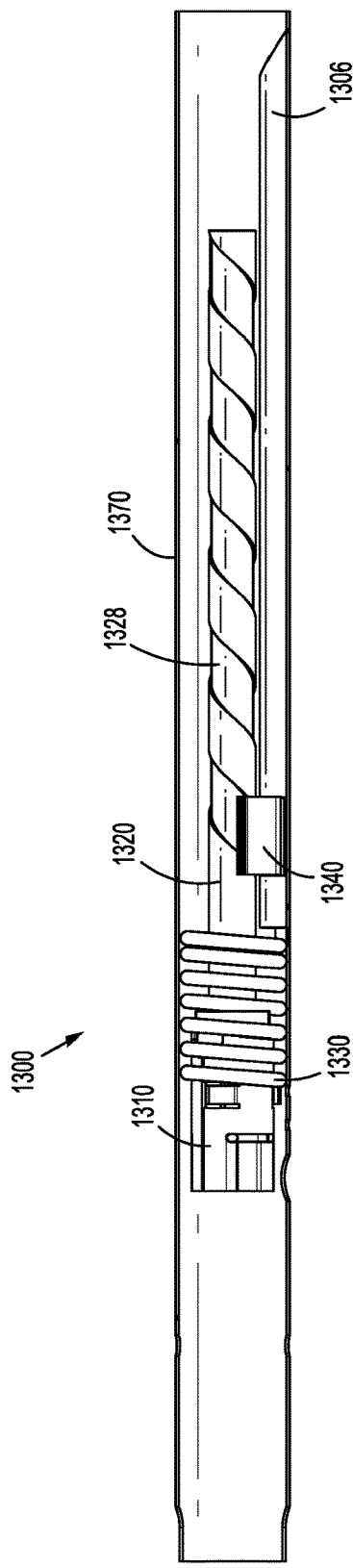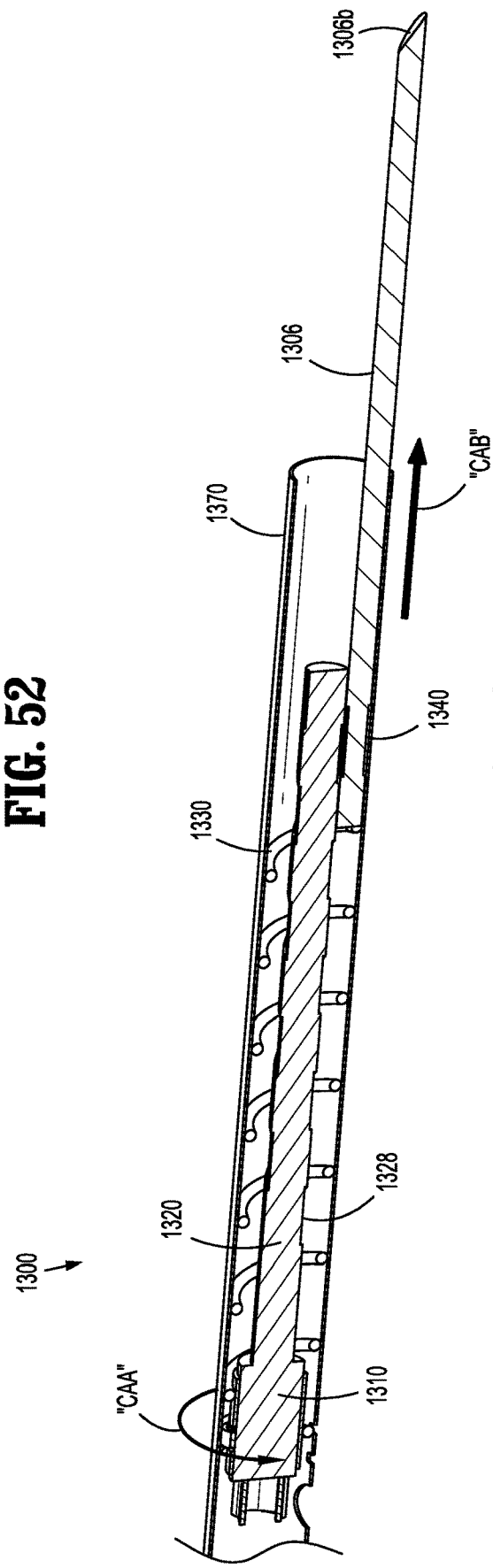
FIG. 52
FIG. 53

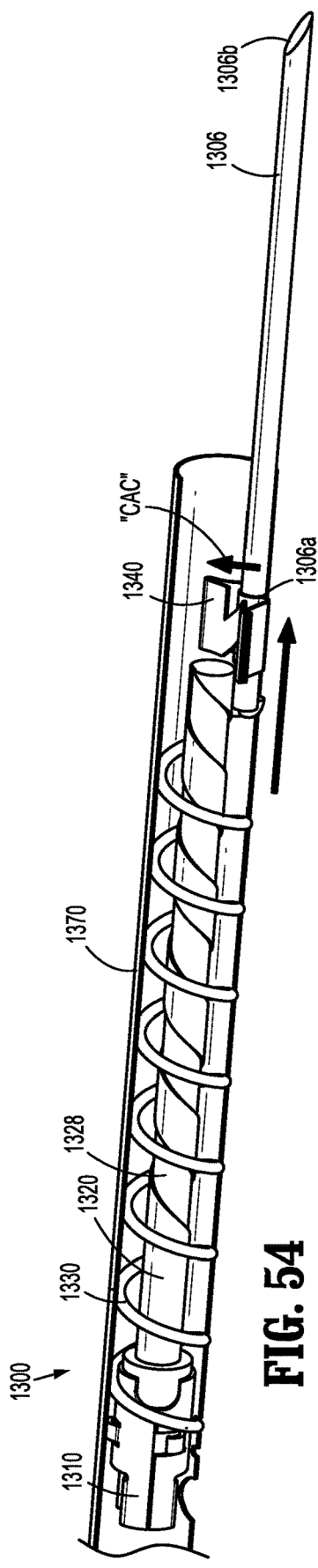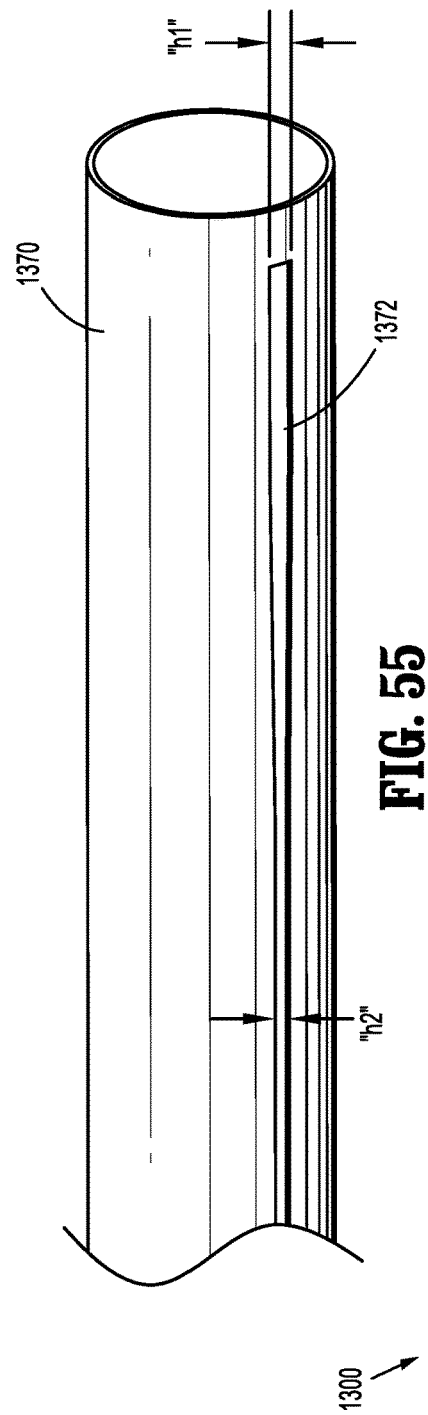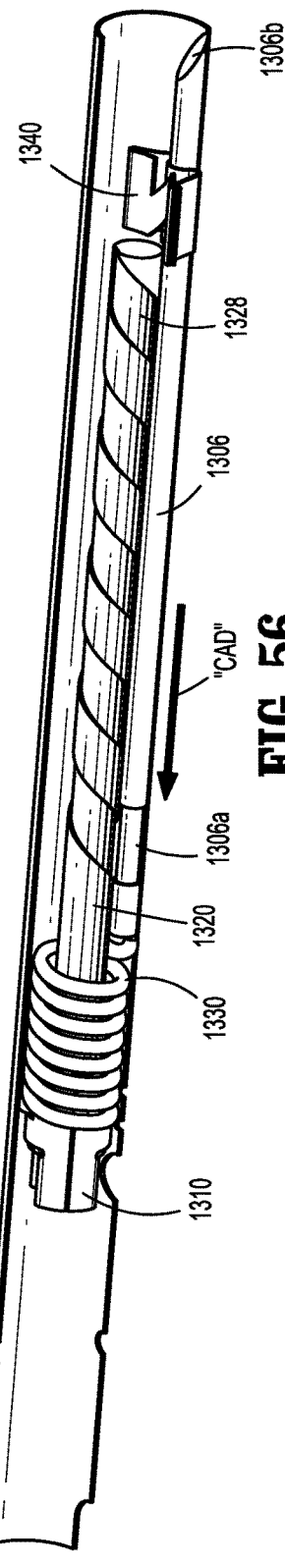

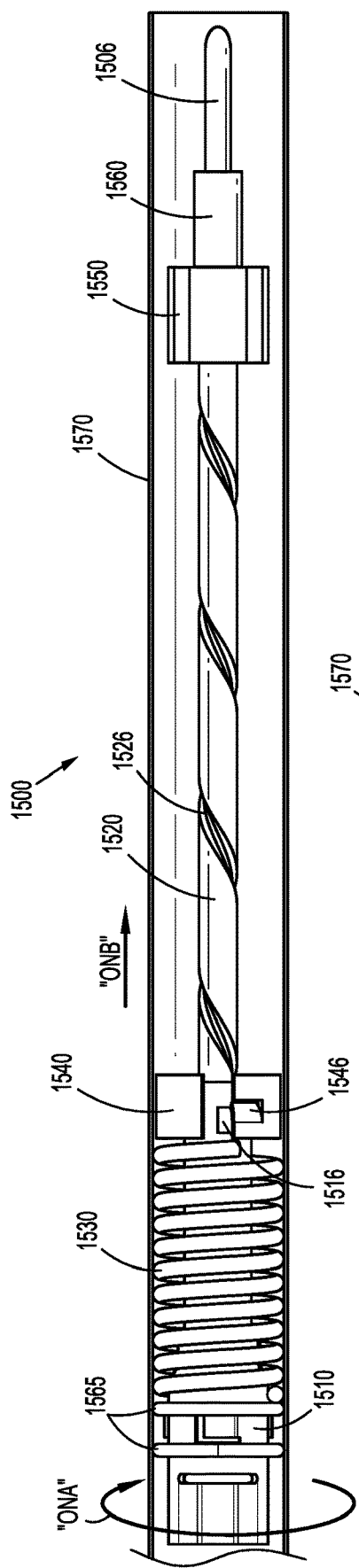
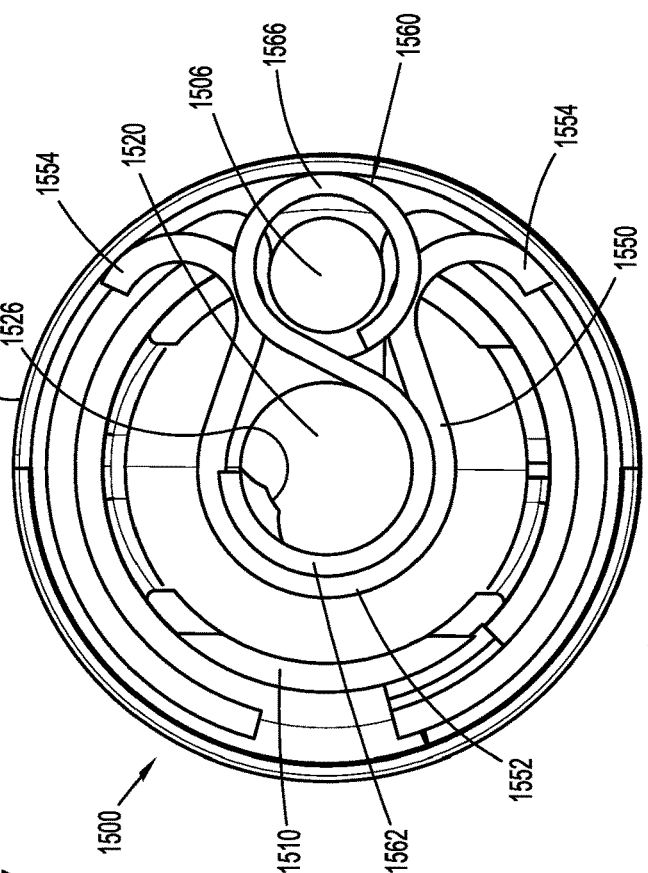

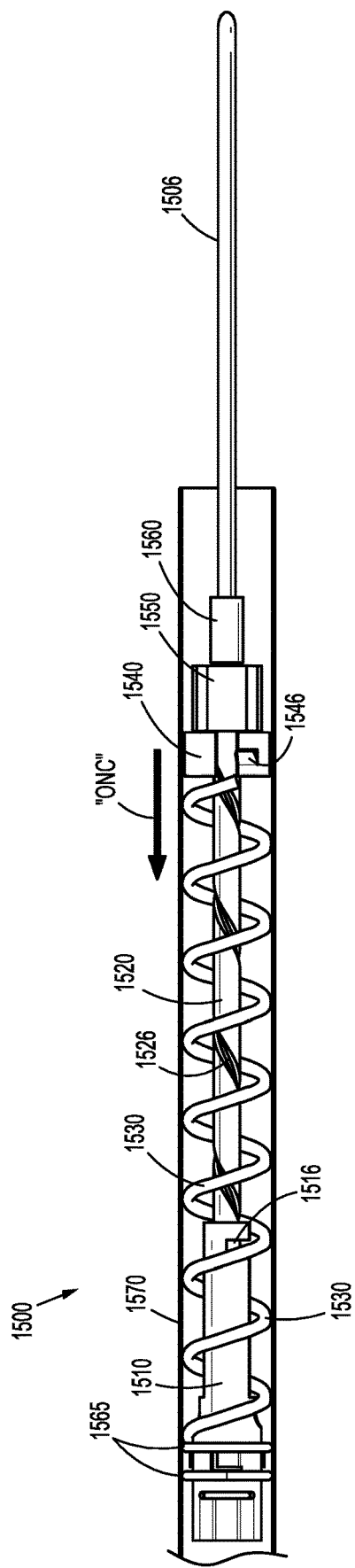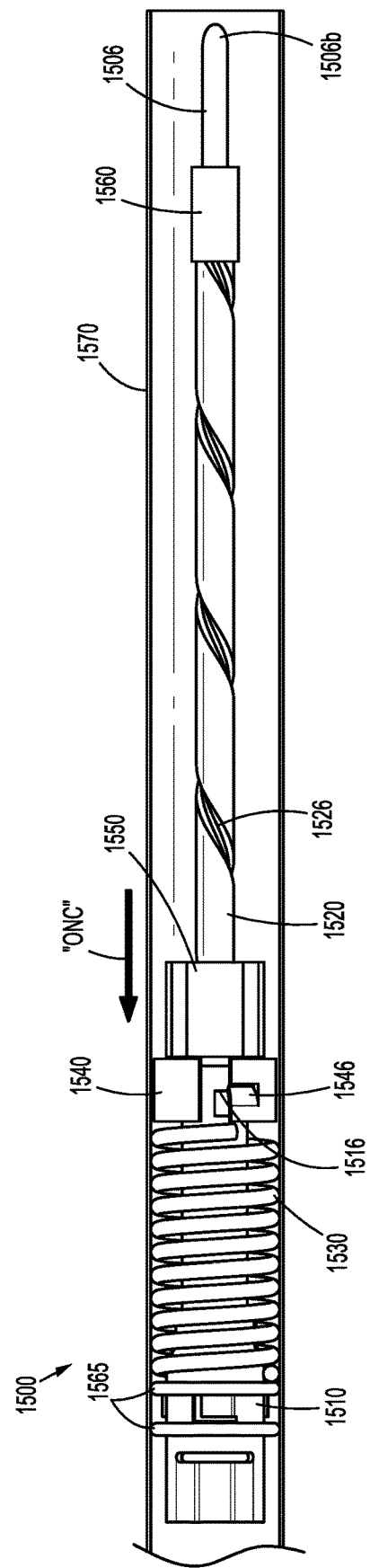

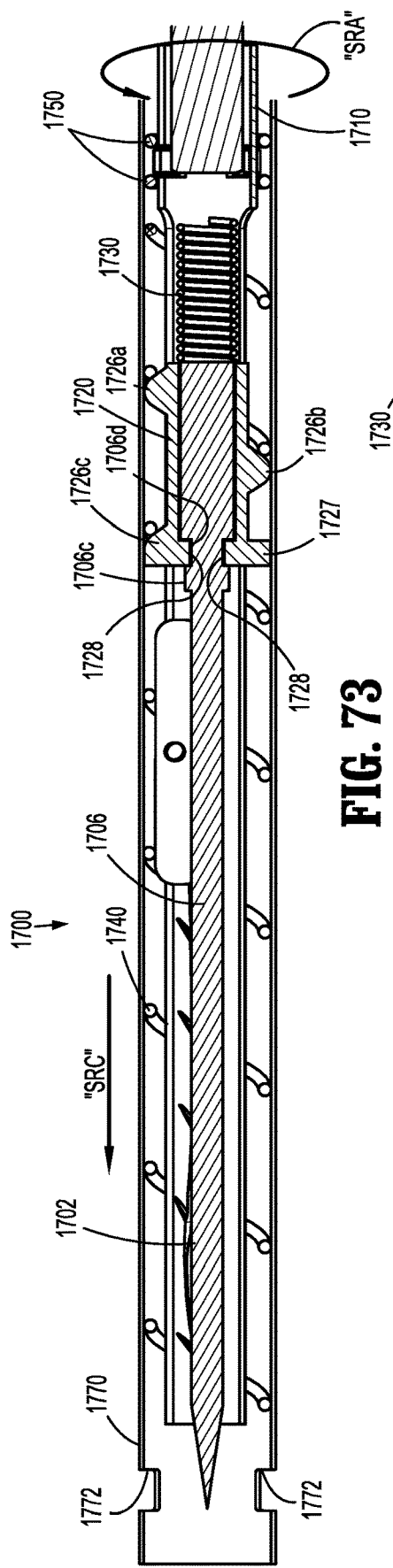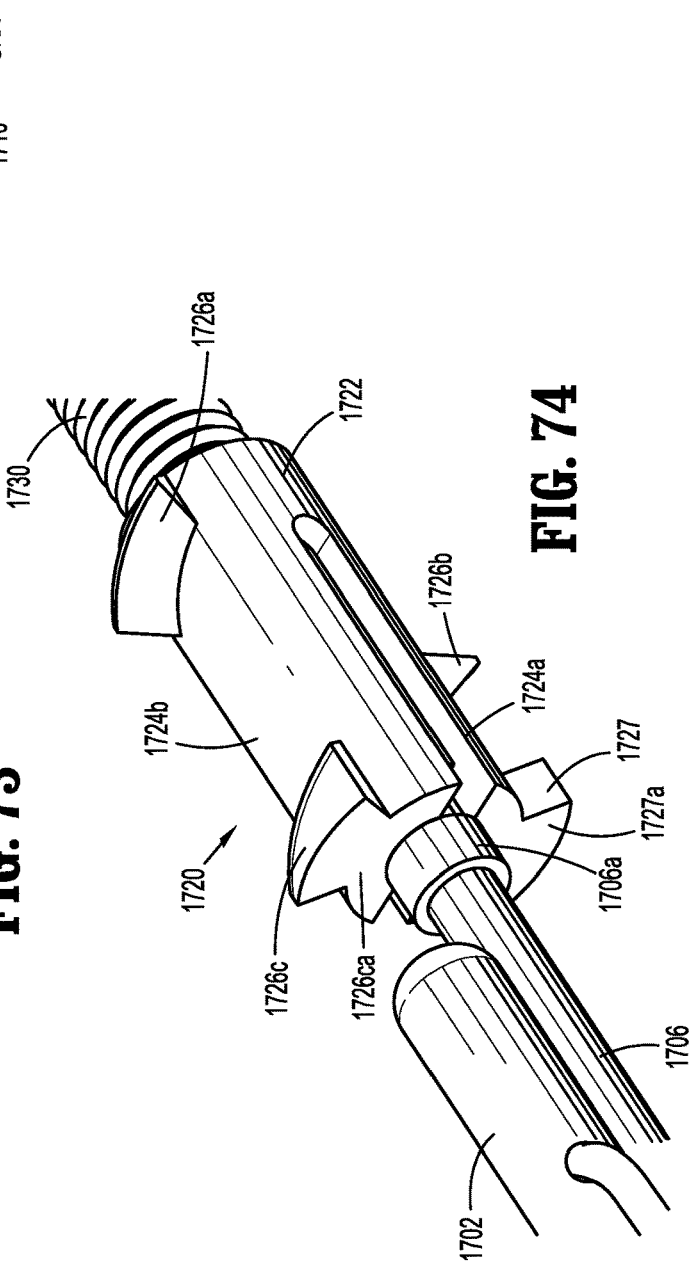

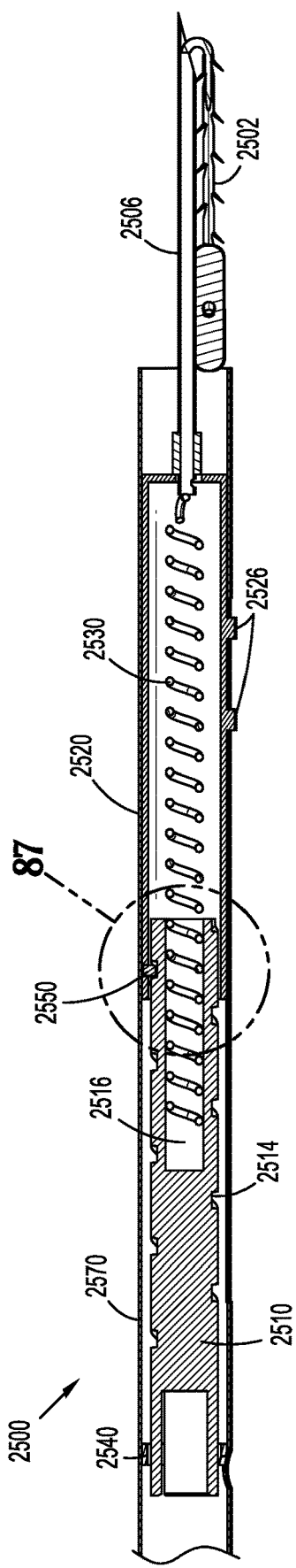
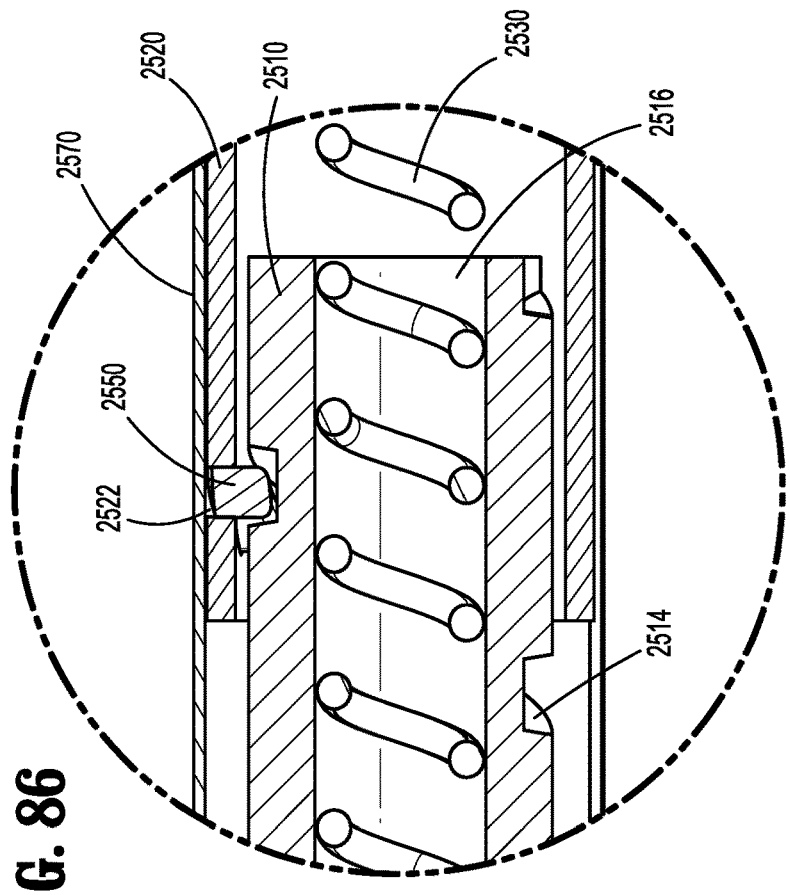
FIG. 86
FIG. 87

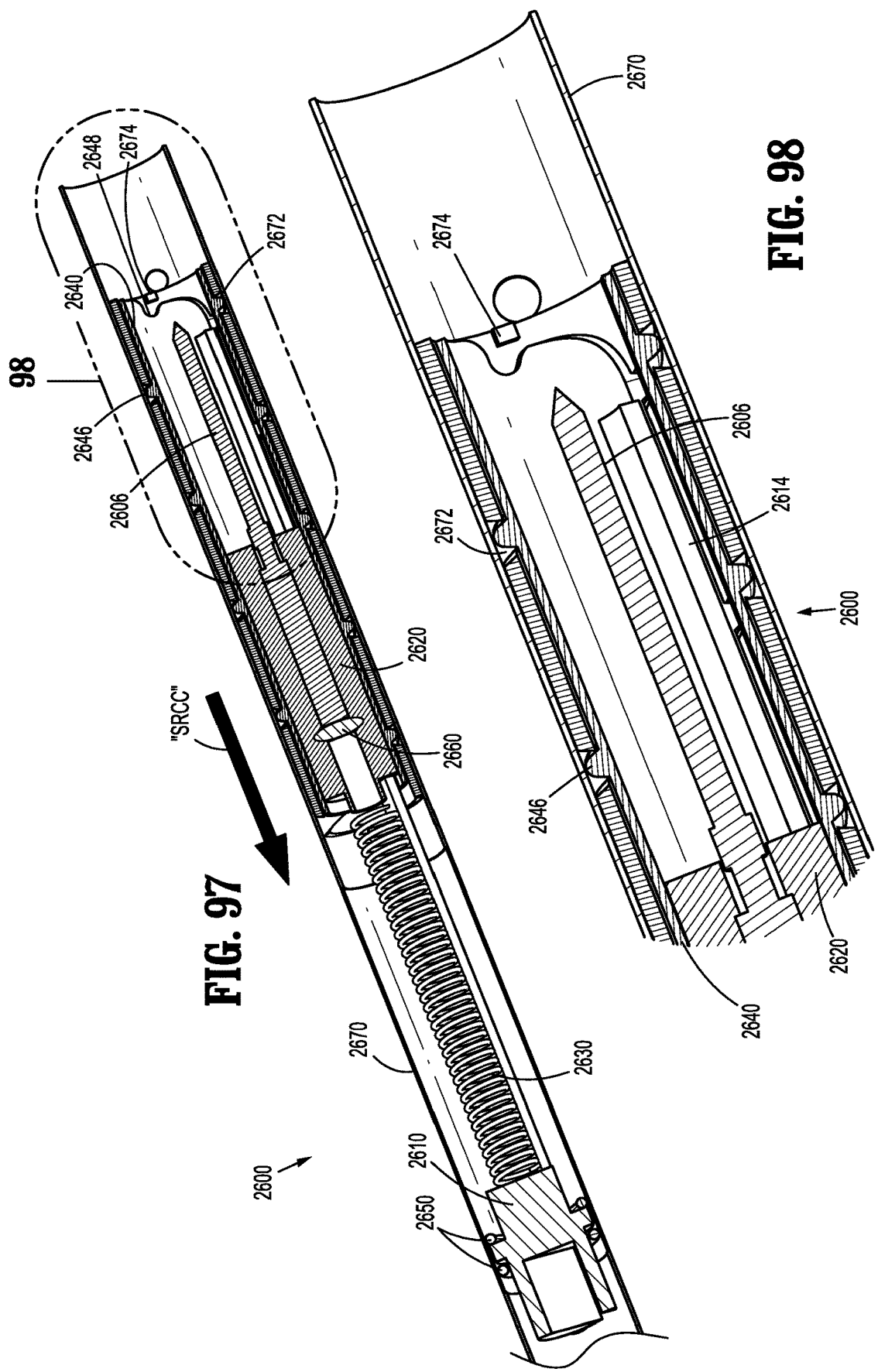

SURGICAL END EFFECTORS

CROSS-REFERENCE TO RELATED APPLICATIONS

This application is a continuation of U.S. patent application Ser. No. 15/678,156, filed on Aug. 16, 2017 (now U.S. Pat. No. 10,617,409), which claims the benefit of and priority to U.S. Provisional Patent Application No. 62/410,879, filed Oct. 21, 2016, the entire disclosures of each of which are incorporated by reference herein.

BACKGROUND

Technical Field

The present disclosure relates to end effectors for use with a surgical device for performing endoscopic surgical procedures and methods of use thereof. More specifically, the present disclosure relates to end effectors for advancing at least a portion of a needle into tissue.

Background of Related Art

During laparoscopic or endoscopic surgical procedures, access to a surgical site is achieved through a small incision or through a narrow cannula inserted through a small entrance wound in a patient. Several types of such surgical procedures include advancing at least part of a needle and/or suture into tissue. For example, it may be desired to insert a suture (e.g., a barbed suture) through an implant (e.g., mesh) and into tissue to help secure the implant to tissue. It may also be desired to replace suture that was previously inserted through the implant.

Additionally, after a needle is advanced into tissue, it may be desired to retract the needle in an outer tube of a surgical device or an end effector to prevent or minimize unintended contact between the needle and a physician, for instance.

Accordingly, a need exists for endoscopic surgical devices or end effectors for use therewith including the ability to advance and retract a needle into its outer tube.

SUMMARY

The present disclosure relates to an end effector for use with a surgical device, where the end effector includes a driver, a clip assembly, a needle assembly, and biasing element. The clip assembly is disposed in mechanical cooperation with the driver. Rotation of the driver results in longitudinal translation of the clip assembly. The needle assembly is selectively engaged with the clip assembly. The biasing element is disposed in mechanical cooperation with the needle assembly and is configured to bias the needle assembly proximally.

In disclosed embodiments, the clip assembly engages the needle assembly when the needle assembly is in a first, proximal position, and the clip assembly is free from engagement with the needle assembly when the needle assembly is in a distal position.

In aspects of the present disclosure, engagement between the clip assembly and the needle assembly resists the bias exerted on the needle assembly by the biasing element.

It is also disclosed that the end effector includes an outer tube disposed radially outward of the driver. In embodiments, the clip assembly includes at least one arm, and the needle assembly is selectively engaged with the at least one arm of the clip assembly. It is further disclosed that the at least one arm of the clip assembly is biased radially outward into contact with a portion of the outer tube. In embodiments, the outer tube includes at least one aperture defined with a distal portion of the outer tube. A portion of the at least one arm of the clip assembly is configured to engage the at least one aperture after a predetermined amount of distal movement of the clip assembly with respect to the outer tube. Further, engagement between the at least one arm of the clip assembly and the at least one aperture causes the clip assembly to be free from engagement with the needle assembly, and results in proximal movement of the needle assembly with respect to the outer tube.

In disclosed embodiments, the end effector also includes a pin extending laterally through the outer tube. A proximal portion of the biasing element is mechanically engaged with the pin. Further, the pin extends through a longitudinal slot of the clip assembly.

It is also disclosed that the needle assembly includes a first needle extending distally from a needle block, and second needle extending distally from the needle block. The first needle is parallel to the second needle.

It is further disclosed that the end effector includes a suture disposed in mechanical cooperation with a needle of the needle assembly.

The present disclosure also relates to an end effector for use with a surgical device, wherein the end effector includes a driver assembly, a driver, a needle assembly, and a biasing element. The driver is disposed in mechanical cooperation with the drive assembly and includes a threaded portion. The needle assembly is disposed in mechanical cooperation with the driver. Rotation of the drive assembly in a first direction causes distal translation of the driver and the needle assembly with respect to the drive assembly. The biasing element disposed in mechanical cooperation with the needle assembly, the biasing element configured to bias the needle assembly proximally.

It is also disclosed that the needle assembly is configured to move proximally with respect to the driver.

In disclosed embodiments, the end effector includes an outer tube disposed radially outward of at least a portion of the drive assembly. The threaded portion of the driver is configured to engage a threaded portion of the outer tube.

It is further disclosed that a proximal portion of the needle assembly is configured to directly engage a distal portion of the biasing element.

Additionally, it is disclosed that the needle assembly is configured to disengage from the driver after the driver has distally travelled a predetermined amount with respect to the drive assembly.

In aspects of the disclosure, the driver includes a pair of arms biased radially outwardly. Additionally, the end effector includes a tab extending radially inward from at least one arm of the pair of arms. The tab is configured to releasably engage a recess of the needle assembly. In embodiments, the end effector includes an outer tube disposed radially outward of at least a portion of the drive assembly. The outer tube includes at least one notch disposed adjacent a distal end of the outer tube. At least one arm of the pair of arms is configured to move from a first position where the at least one arm is free from engagement with the at least one notch, to a second position where the at least one arm is engaged with the at least one notch. Further, the pair of arms is biased from a first position where the pair of arms is engaged with the needle assembly to a second position where the pair of arms is free from engagement with the needle assembly.

Additionally, engagement between the pair of arms and the needle assembly opposes a biasing force exerted by the biasing element.

It is further disclosed that the end effector includes a suture disposed in mechanical cooperation with a needle of the needle assembly.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIGS. 1 and 2 are perspective views of a surgical device including an end effector engaged therewith according to embodiments of the present disclosure;

FIG. 3 is an enlarged view of the indicated area of detail of FIG. 2;

FIGS. 5-8 illustrate various types of needles and sutures in accordance with embodiments of the present disclosure;

FIGS. 9-20 illustrate various embodiments showing a needle engaged with a suture in accordance with embodiments of the present disclosure;

FIG. 25 is a perspective view of portions of the end effector of FIGS. 21-24;

FIG. 26 is an enlarged view of the area of detail indicated in FIG. 25;

FIG. 27 is an enlarged view of the area of detail indicated in FIG. 25;

FIG. 28 is a perspective view of portions of the end effector of FIGS. 21-27;

FIG. 29 is a perspective view of the needle of FIG. 28;

FIG. 31 is a perspective view of portions of the end effector of FIGS. 21-30;

FIG. 32 is an enlarged view of the area of detail indicated in FIG. 31;

FIG. 33 is an enlarged view of the area of detail indicated in FIG. 31;

FIG. 46 is a perspective view of an end effector in accordance with embodiments of the present disclosure;

FIG. 47 is a perspective view of portions of the end effector of FIG. 46;

FIG. 52 is a side view of portions of the end effector of FIGS. 46-51;

FIG. 53 is a cut-away view of portions of the end effector of FIGS. 46-52 illustrating a needle in an advanced position;

FIG. 54 is a perspective view of portions of the end effector of FIGS. 46-53 illustrating a needle in an advanced position;

FIG. 55 is a perspective view of a distal portion of the end effector of FIGS. 46-54;

FIG. 56 is a perspective view of portions of the end effector of FIGS. 46-55 illustrating a needle in a retracted position;

FIG. 67 is a side view of portions of the end effector of FIGS. 65-66;

FIG. 68 is an end view of the end effector of FIGS. 65-67;

FIG. 69 is a side view of portions of the end effector of FIGS. 65-68 illustrating a needle in an advanced position;

FIG. 70 is a side view of portions of the end effector of FIGS. 65-69 illustrating the needle in a retraced position;

FIG. 73 is a cross-sectional view of the end effector of FIGS. 71-72;

FIG. 74 is a perspective view of portions of the end effector of FIGS. 71-73;

FIG. 86 is a cross-sectional view of the end effector of FIGS. 83-85 illustrating a needle in an advanced position;

FIG. 87 is an enlarged view of the area of detail indicated in FIG. 86;

FIG. 97 is a cross-sectional view of the end effector of FIGS. 91-96;

FIG. 98 is an enlarged view of the area of detail indicated in FIG. 97;

DETAILED DESCRIPTION

Figure 1:
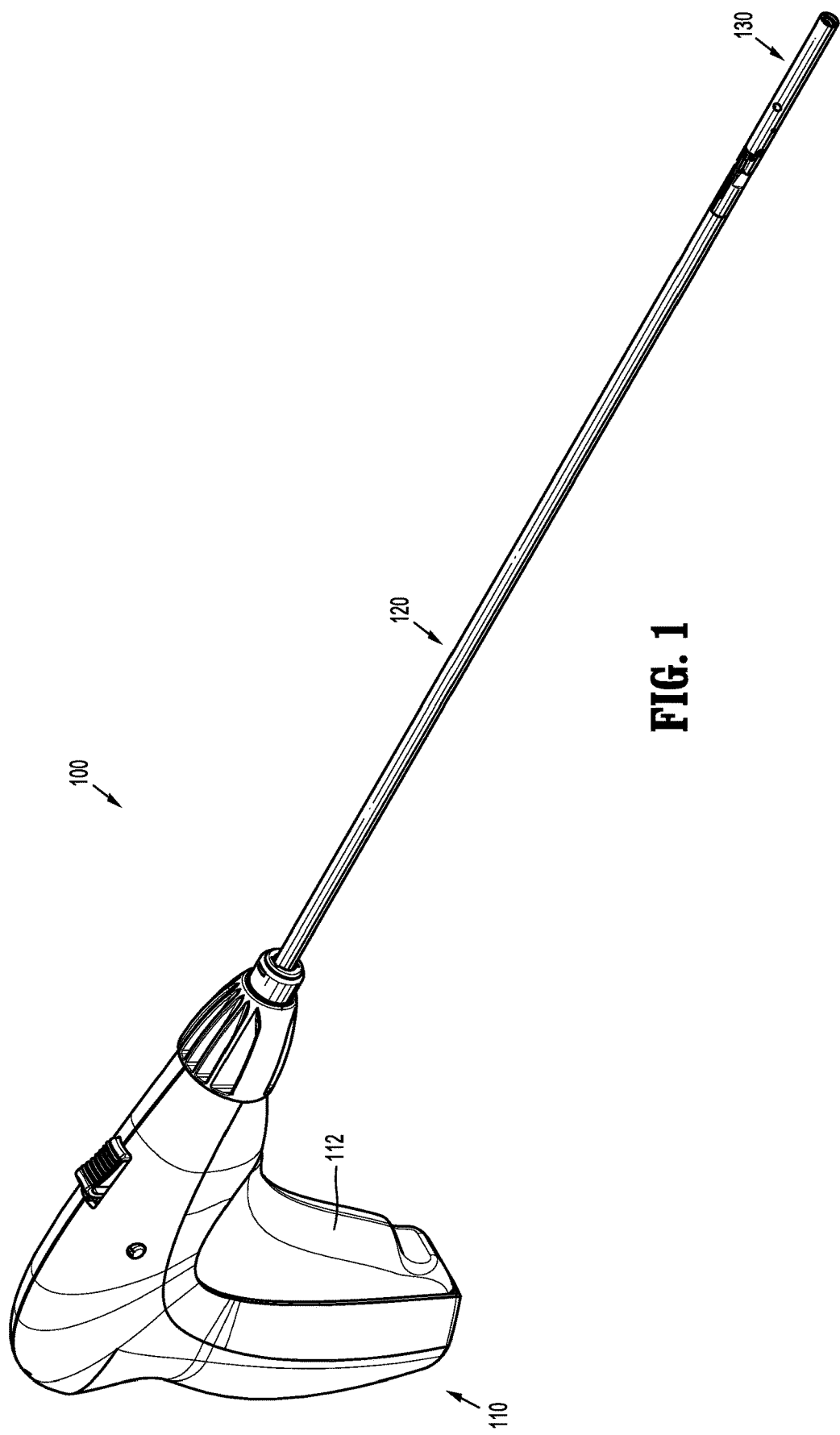
Figure 4:
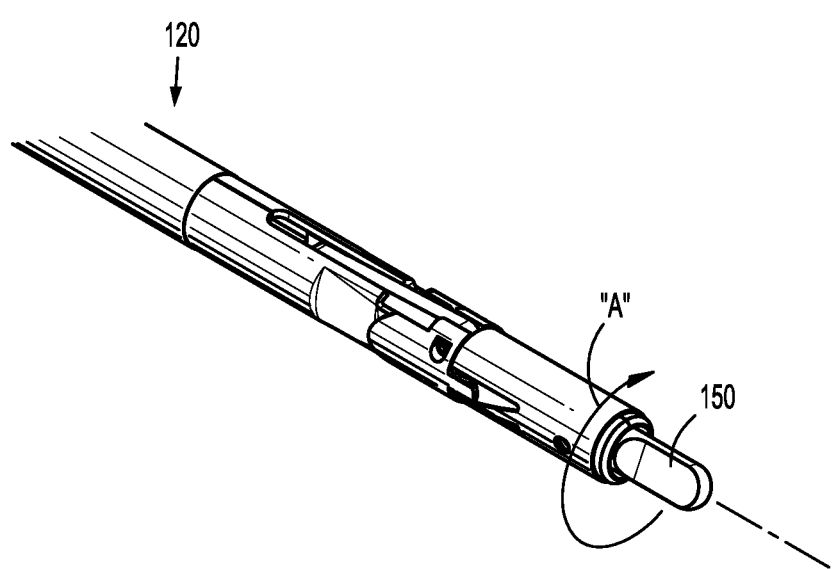
FIG. 4 is a perspective view of a distal portion of an elongated portion of the surgical device of FIGS. 1-3.

Embodiments of the presently disclosed endoscopic surgical device is described in detail with reference to the drawings, in which like reference numerals designate identical or corresponding elements in each of the several views. As used herein the term "distal" refers to that portion of the endoscopic surgical device that is farther from the user, while the term "proximal" refers to that portion of the surgical device that is closer to the user.

Non-limiting examples of surgical devices which may include articulation joints according to the present disclosure include manual, mechanical and/or electromechanical surgical tack appliers (i.e., tackers), clip appliers, surgical forceps, and the like.

Referring initial to FIGS. 1-4, a surgical instrument for use with the various end effectors of the present disclosure is generally designated as surgical device 100. Surgical device 100 includes a handle assembly 110, an elongated portion 120 extending distally from handle assembly 110, an end effector 130 disposed in mechanical cooperation (e.g., releasably engaged) with a distal portion of elongated portion 120, and a drive rod 150 disposed at least partially within elongated portion 120 and configured to engage (e.g., releasably engage) end effector 130. For clarity, FIGS. 1-3 illustrate a general end effector 130; various other end effectors are shown and described throughout this application and are configured for use with surgical device 100. Generally, end effector 130 is a separable component that is able to be used with a surgical instrument (e.g., a surgical fixation device handle). After its use (e.g., after one or more barbed sutures are released therefrom), the end effector 130 can be removed from the remainder of the surgical instrument, and a new or reloaded end effector 130 can then engage the surgical instrument and be used.

Handle assembly 110 includes a trigger or an actuator 112 (e.g., button, switch, etc.) thereon. In general, actuation of actuator 112 results in rotation of drive rod 150, e.g., in the general direction of arrow "A" in FIG. 4. There are a variety of ways surgical device 100 can transfer the movement caused by actuation of actuator 112 to rotation of drive rod 150, such as those disclosed in U.S. patent application Ser. No. 15/049,511, filed on Feb. 22, 2016, now U.S. Pat. No. 10,085,746, the entire contents of which are hereby incorporated by reference herein.

Several of the end effectors of the present disclosure are usable to advance at least a portion of a needle and/or at least a portion of a suture (e.g., a barbed suture) or other fixation device into tissue and/or mesh, for instance. An example of a disclosed use of the end effectors relates to positioning and/or fixation of laparoscopic ventral mesh. In such procedures, stay-sutures are typically tied to the corners and/or cardinal points by surgeons. The mesh and sutures are then rolled and introduced through the trocar and into the laparoscopic working space. The mesh is then unrolled, and positioned into place. If the sutures have needles attached, care must be taken during rolling, insertion, unrolling and positioning to help ensure the needle points do not damage the mesh (especially if the mesh includes an adhesion barrier layer) or to injure the patient or clinician. Once the mesh is properly unrolled and placed against the abdominal wall in the correct location, the stay-sutures are delivered across the abdominal wall (either from the inside toward the outside using an attached needle, or from the outside toward the inside using a suture passer introduced from outside the abdominal wall to grasp and pull the suture from the laparoscopic working space). After the stay-sutures have all been inserted, the clinician can finish fixating the mesh to the abdominal wall with a separate fixation device, such as a surgical tack applier.

The various end effectors disclosed herein help standardize surgical procedures (e.g., positioning and/or fixation of laparoscopic ventral mesh) and reduce the number of steps and time required to fixate the mesh with stay-sutures. The needle assemblies of the present disclosure allow a surgeon to introduce and pass a stay-suture through the implant and abdominal wall without the need to pre-attach the stay-sutures to needles, and without the risk of accidental needle sticks. The disclosed end effectors can used as a reload for use with standard surgical device handles to minimize the number of surgical devices (and the expense) needed for related surgical procedures.

Needle Styles

A variety of different types of needles may be used in combination with various embodiments of the present disclosure. While FIGS. 5-8 illustrate several types of needles, other types of needles may be used with the various end effectors disclosed herein. FIG. 5 illustrates a single needle 3000a extending from a needle block 3002, and a barbed suture 3010a operatively engaged (e.g., releasably engaged) therewith such that needle 3000a and barbed suture 3010a are insertable into an implant/tissue, and barbed suture 3010a remains in engagement with the implant/tissue when needle 3000a is retracted. A pledget 3003a is also included adjacent proximal portions of needle 3000a and barbed suture 3010a, which may releasably hold barbed suture 3010a, and which may act as a stop to help limit the distal advancement of barbed suture 3010a into the implant/tissue. A distal portion of barbed suture 3010a may be bent into a hollow cavity at a distal portion of needle 3000a to help releasably retain barbed suture 3010a in engagement with needle 3000a. FIG. 6 illustrates a pair of needles 3000b disposed in a parallel relationship extending from needle block 3002, and a suture 3010b supported between needles 3000b. Each needle of pair of needles 3000b extends distally from needle block 3002 in a direction that is perpendicular to a distal face 3002b of needle block 3002 (e.g., parallel to a longitudinal axis defined by an elongated portion of surgical device 100 engaged with needle block 3002). Pair of needles 3000b is sufficiently sturdy to support suture 3010b therebetween. A distal portion of suture 3010b may be bent into a hollow cavity at a distal portion of needle 3000b to help releasably retain suture 3010b in engagement with needles 3000b. It is envisioned that an adhesive is used to temporarily retain suture 3010b in the illustrated position. In use, at least a portion of needles 3000b and suture 3010b are inserted into/through an implant/tissue to emplace suture 3010b through the implant, for example. Suture 3010b remains emplaced through the implant up retraction of needles 3000b. Another suture 3010b can then be positioned between needles of pair of needles 3000b to allow for repeated use of pair of needles 3000b. FIG. 7 illustrates a pair of needles 3000c disposed in a bowed relationship extending from needle block 3002, and a suture 3010c supported between needles 3000c. Needles 3000c extend radially outward from each other, such that distal ends 3002c of needles 3000c are farther apart than proximal ends 3004c of needles 3000c. Pair of needles 3000c is sufficiently sturdy to support suture 3010c therebetween. A distal portion of suture 3010c may be bent into a hollow cavity at a distal portion of needle 3000c to help releasably retain suture 3010c in engagement with needles 3000c. It is envisioned that an adhesive is used to temporarily retain suture 3010c in the illustrated position. FIG. 8 illustrates a pair of needles 3000d extending in an arcuate manner from needle block 3002, and supporting a suture 3010d at least partially therebetween. Further, distal portions of suture 3010d are engaged with distal portions of needles 3000d. A distal portion of suture 3010d may be bent into a hollow cavity at a distal portion of needle 3000d to help releasably retain suture 3010d in engagement with needles 3000d. It is envisioned that an adhesive is used to temporarily retain suture 3010d in the illustrated position. Pair of needles 3000d may be used when a clinician desires to secure a relatively wide portion of an implant or tissue, as the distal tips of needles 3000d are positioned far away from each other, with respect to pair of needles 3000b and 3000c. It is envisioned that needles 3000a, 3000b, 3000c and 3000d are made from a shape memory material, such as nitinol.

Needle Tip Attachment

Figure 9:
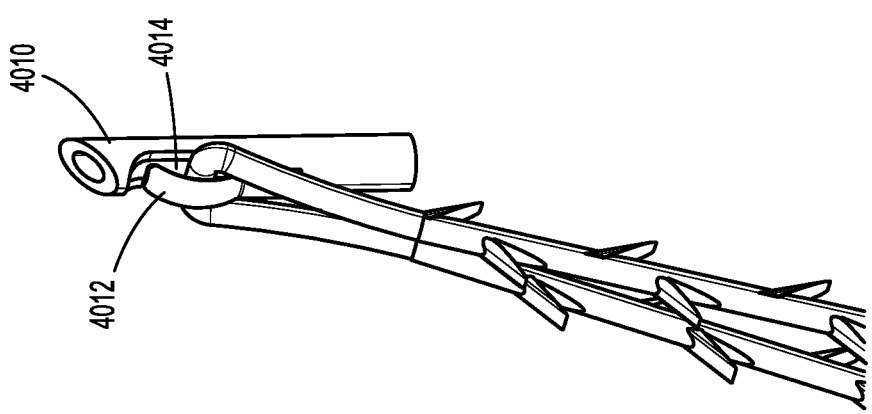

Several different ways of coupling needles with suture are usable with embodiments of end effectors disclosed herein and are illustrated in FIGS. 9-20. In FIG. 9, a needle 4010 is shown including a flange 4012 projecting from a recess 4014 within a shaft of needle 4010. A distal end of flange 4012 may be able to move, flex or pivot away from recess 4014. A barbed suture 4000 is releasably held by flange 4012. In use, distal advancement of needle 4010 towards (e.g., into) tissue causes a corresponding distal advancement of barbed suture 4000. When needle 4010 is moved proximally or retracted, flange 4012 moves over or releases barbed suture 4000, thus leaving barbed suture 4000 within tissue, for example.

Figure 11:
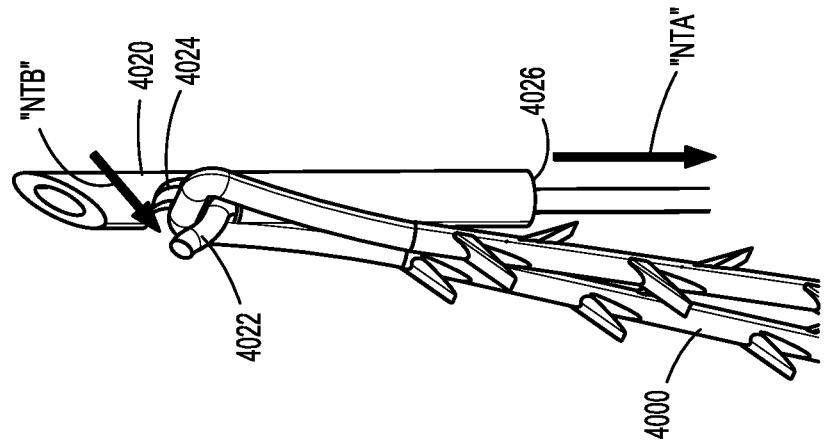
Figure 10:
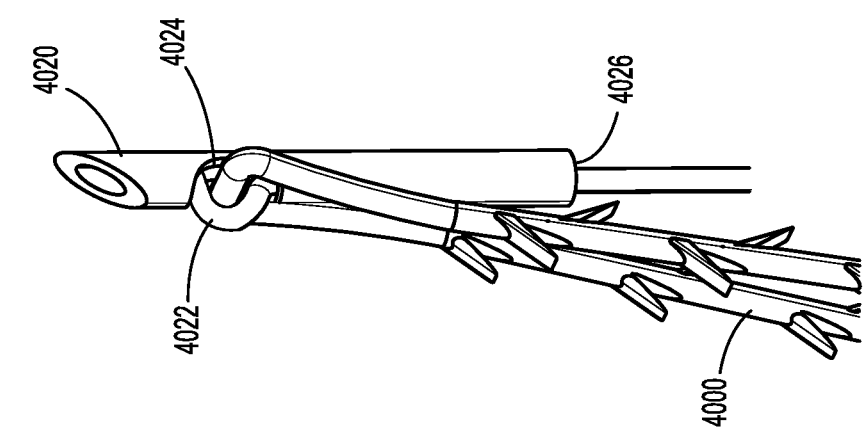

In FIGS. 10-11, a needle 4020 is shown including an actuation suture 4022 extending through needle 4020 between a recess 4024 within a shaft of needle 4020 and a proximal opening 4026 of needle 4020. A distal portion of actuation suture 4022 releasably holds barbed suture 4000. In use, distal advancement of needle 4020 towards (e.g., into) tissue causes a corresponding distal advancement of barbed suture 4000. When actuation suture 4022 is moved proximally or retracted in the general direction of arrow "NTA," distal portion of actuation suture 4022 moves in the general direction of arrow "NTB" or releases barbed suture 4000, thus leaving barbed suture 4000 within tissue, for example. It is envisioned that a proximal portion of actuation suture 4022 is engaged with an appropriate anchor portion of an end effector such that advancement of needle 4020 moves needle 4020 away from the anchor portion of the end effector, which causes a relative retraction of actuation suture 4022.

In FIGS. 12-13, a needle 4030 is shown including a suture 4002 engaged with a cavity 4032 of needle 4030. Cavity 4032 of needle 4030 includes a first, proximal portion 4032a and a second, distal portion 4032b. As shown, distal portion 4032b of cavity 4032 is deeper than proximal portion 4032a of cavity 4032. Distal portion 4032b of cavity 4032 is configured to releasably engage an enlarged or ball portion 4002a of suture 4002, and proximal portion 4032a of cavity 4032 is configured to releasably engage a body portion 4002b of suture 4002. In use, distal advancement of needle 4030 towards (e.g., into) tissue causes a corresponding distal advancement of suture 4002. When needle 4030 is moved proximally or retracted, suture 4002 is able to slide in the general direction of arrow "NTA" relative to needle 4030, thus leaving suture 4002 within tissue, for example.

Figure 15:
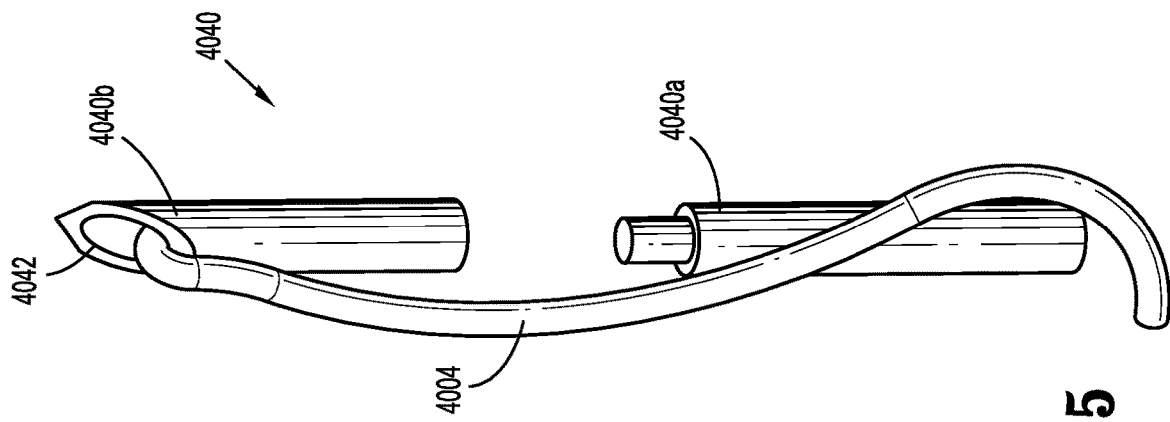
Figure 14:
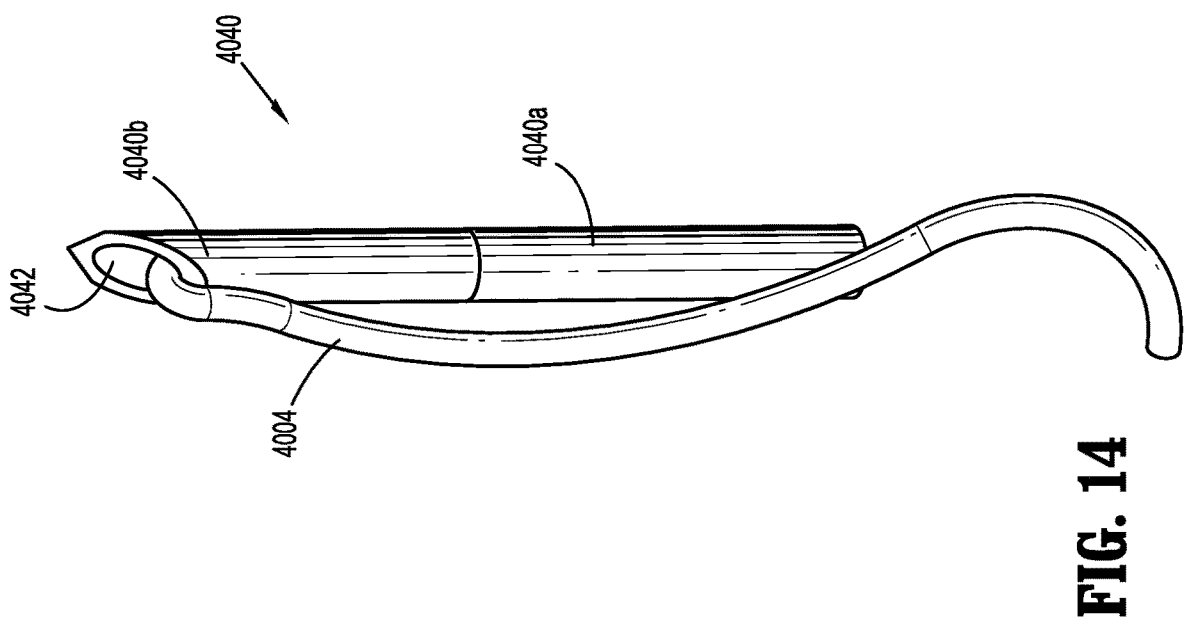

In FIGS. 14-15, a needle 4040 is shown including a proximal portion 4040a and a distal portion 4040b. Proximal portion 4040a and distal portion 4040b of needle 4040 are releasably engaged with each other. Accordingly, moving proximal portion 4040a proximally with respect to distal portion 4040b, for example, can separate the two portions of needle 4040. A suture 4004 is engaged with a distal part of distal portion 4040b of needle 4040. For example, a portion of suture 4004 is disposed within a cavity 4042 of distal portion 4040b of needle 4040. In use, distal advancement of needle 4040 towards (e.g., into) tissue causes a corresponding distal advancement of suture 4004. When proximal portion 4040a of needle 4040 is moved proximally or retracted, distal portion 4040b of needle 4040 separates from proximal portion 4040a, which results in distal portion 4040b of needle 4040 and portions of suture 4004 remaining in tissue.

In FIG. 16, a needle 4050 is shown including an angled axial cut 4052 disposed therein. Angled axial cut 4052 of needle 4050 is configured to frictionally and releasably hold a portion of suture 4004 therein. In use, distal advancement of needle 4050 towards (e.g., into) tissue causes a corresponding distal advancement of suture 4004. When needle 4050 is moved proximally or retracted, portions of suture 4004 release from angled axial cut 4052 and remain within tissue, for example. It is envisioned that needle 4050 may be manufactured using an angled mill.

In FIG. 17, a needle 4060 is shown including a perpendicular axial cut 4062 disposed therein. Perpendicular axial cut 4062 of needle 4060 is configured to frictionally and releasably hold a portion of suture 4004 therein. In use, distal advancement of needle 4060 towards (e.g., into) tissue causes a corresponding distal advancement of suture 4004. When needle 4060 is moved proximally or retracted, portions of suture 4004 release from perpendicular axial cut 4062 and remain within tissue, for example. It is envisioned that needle 4060 may be manufactured using a cut off wheel.

In FIG. 18, a needle 4070 is shown including a lateral aperture 4072 disposed therethrough. Lateral aperture 4072 of needle 4070 is configured to allow a portion of suture 4004 to be threaded therethrough. In use, distal advancement of needle 4070 towards (e.g., into) tissue causes a corresponding distal advancement of suture 4004. When needle 4070 is moved proximally or retracted, portions of suture 4004 are removed from lateral aperture 4072 and remain within tissue, for example. It is envisioned that a pin or wire travels through needle 4070 to sever suture 4004.

In FIGS. 19 and 20, a needle 4080 is shown including a slotted tip 4082. Slotted tip 4082 of needle 4080 is configured to frictionally and releasably hold a portion of suture 4004 (FIG. 19) or multiple sutures (FIG. 20) therein. In use, distal advancement of needle 4080 towards (e.g., into) tissue causes a corresponding distal advancement of suture(s) 4004. When needle 4080 is moved proximally or retracted, portions of suture(s) 4004 are removed from slotted tip 4082 and remain within tissue, for example.

Spring Loaded Safety Cover

Referring now to FIGS. 21-33, an embodiment of an end effector 1000 including a spring-loaded safety cover assembly is shown. End effector 1000 is configured for use in connection with surgical device 100. Generally, end effector 1000 is configured to prevent unintentional contact with a needle and/or a barbed suture within or extending distally from its outer tube. While FIGS. 21-33 illustrate a particular type of barbed suture 1002 and a particular type of needle 1006, end effector 1000 may be used with different types of sutures and/or needles.

Figure 21:
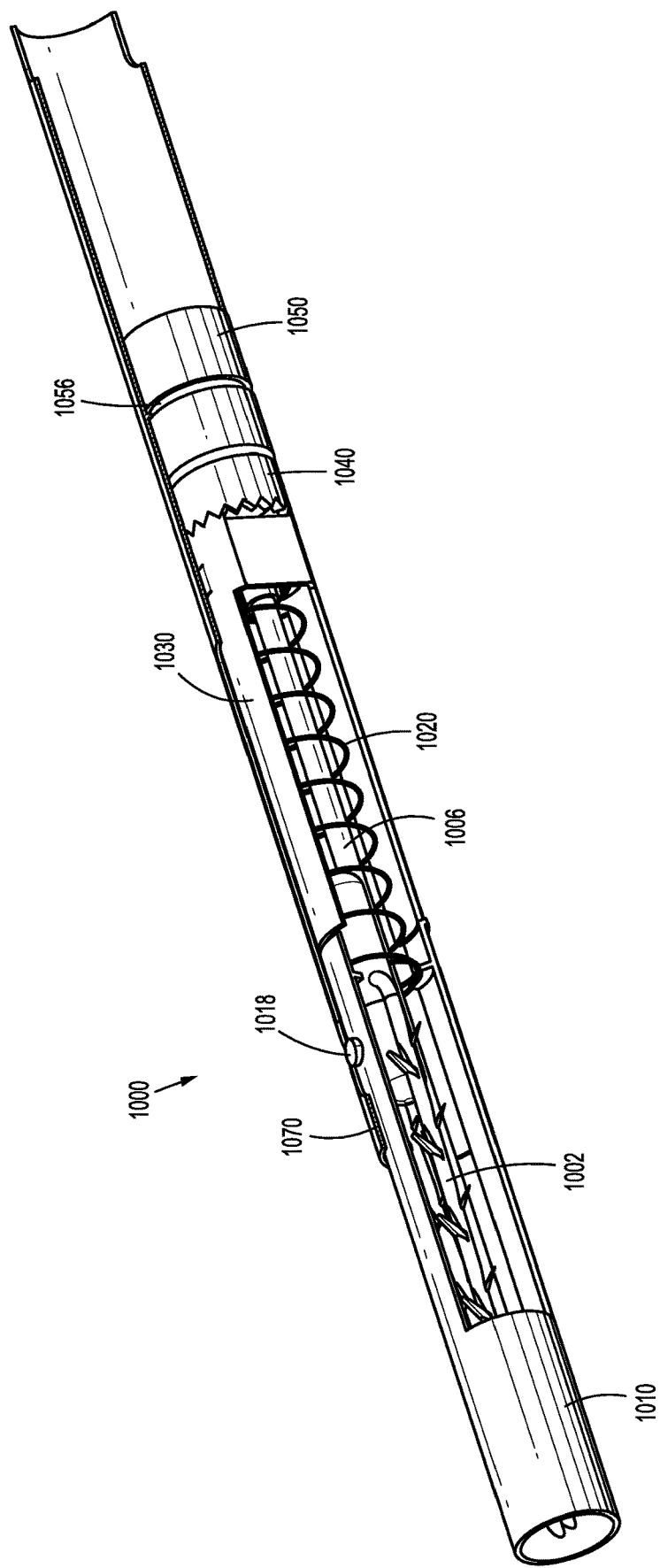
FIG. 21 is a perspective view of portions of an end effector in accordance with embodiments of the present disclosure.
Figure 22:
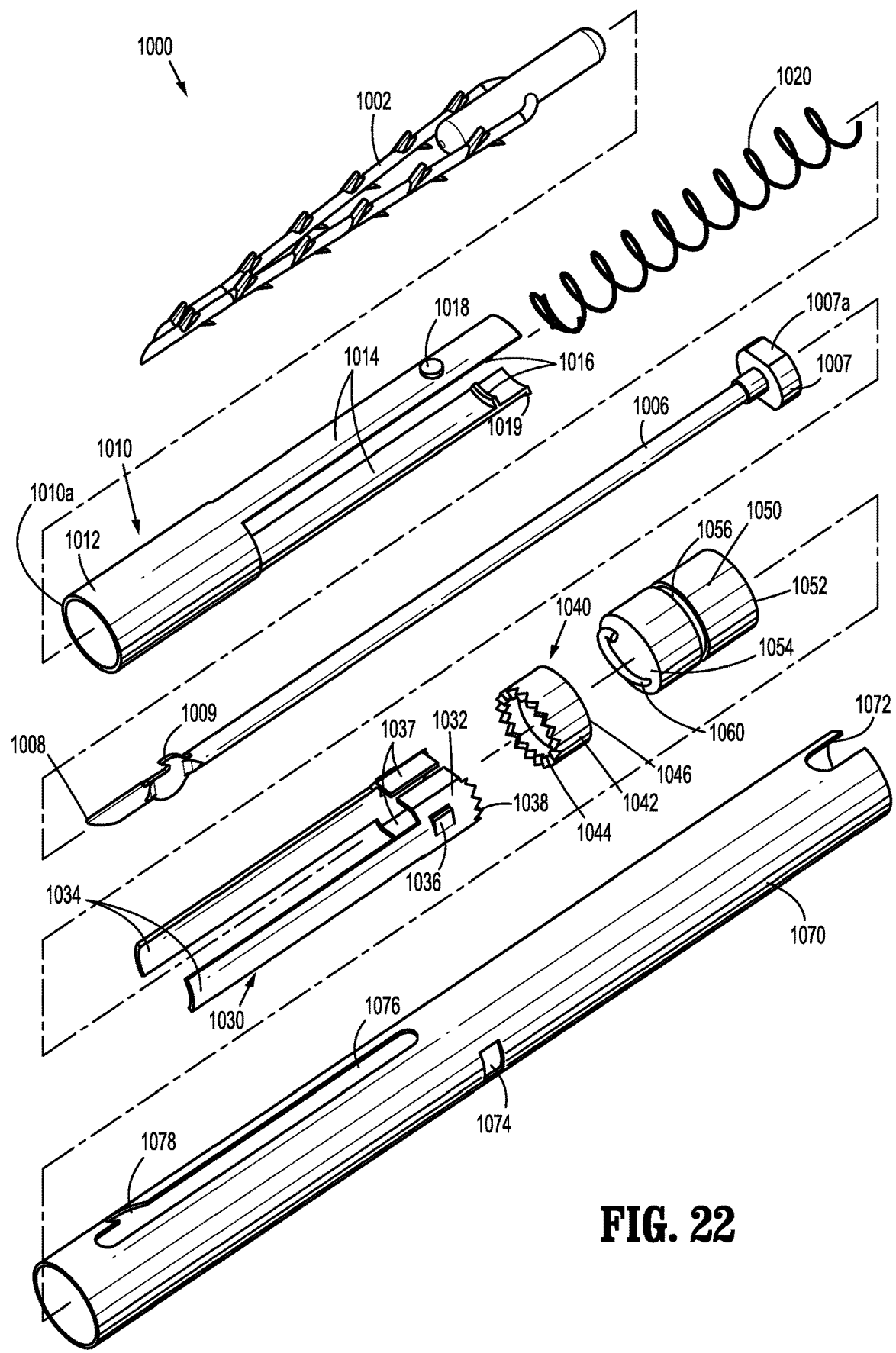
FIG. 22 is an assembly view of the end effector of FIG. 21.

With particular reference to FIGS. 21 and 22, end effector 1000 includes a cover 1010, a first biasing element or spring 1020, a clevis 1030, a clutch 1040, a drive element 1050, a second biasing element or spring 1060 (FIG. 22), and an outer tube 1070.

Cover 1010 of end effector 1000 includes a cylindrical body portion 1012, a pair of arms 1014 extending proximally from body portion 1012, a lip 1016 extending radially inward from a proximal portion of each arm 1014, and a tab 1018 extending radially outward from a proximal portion of one the arms 1014.

Clevis 1030 of end effector 1000 includes a body portion 1032, a pair of arms 1034 extending distally from body portion 1032, a flange 1036 extending radially outward from body portion 1032, and a plurality of teeth 1038 disposed on a proximal end of body portion 1032. First biasing element 1020 is positioned between arms 1034 of clevis 1030 and arms 1014 of cover 1010. Body portion 1032 of clevis 1030 engages a proximal end of first biasing element 1020; lips 1016 of cover 1010 engage a distal end of first biasing element 1020.

A proximal portion 1007 of needle 1006 is positioned radially inward of body portion 1032 of clevis 1030. Further, flat portions 1007a (see FIG. 28) of proximal portion 1007 of needle 1006 engage corresponding flat portions 1037 of body portion 1032 of clevis 1030, thus limiting or preventing rotation therebetween. Needle 1006 also includes a distal tip 1008 and a hook 1009. Distal tip 1008 of needle 1006 is configured to pierce tissue, and hook 1009 of needle 1006 is configured to engage a portion of barbed suture 1002.

Clutch 1040 of end effector 1000 includes a body portion 1042, a plurality of teeth 1044 disposed on a distal end of body portion 1042, and a proximal surface 1046. Teeth 1044 of clutch 1040 are configured to engage teeth 1038 of clevis 1030.

Drive element 1050 of end effector 1000 is mechanically engaged (e.g., operatively coupled, directly affixed, etc.) to drive rod 150 of surgical device 100 of the present disclosure. Drive element 1050 includes a proximal end 1052, a distal end 1054, and a groove 1056. Groove 1056 of drive element 1050 is configured to engage a shipping wedge (not shown) to help lock drive element 1050 in place with respect to outer tube 1070, for example. Proximal end 1052 of drive element 1050 is configured to engage the drive rod. Distal end 1054 of drive element 1050 is mechanically engaged with second biasing element 1060. Proximal surface 1046 of clutch 1040 is positioned to engage second biasing element 1060. That is, second biasing element 1060 is positioned between proximal surface 1046 of clutch 1040 and distal end 1054 of drive element 1050.

Outer tube 1070 of end effector 1000 includes a proximal notch 1072, a cutout 1074, and a longitudinal groove 1076 having an angled slot 1078 extending therefrom. Outer tube 1070 is configured for positioning radially outward of, and to at least partially contain, at least portions of barbed suture 1002, needle 1006, cover 1010, first biasing element 1020, clevis 1030, clutch 1040, drive element 1050, and second biasing element 1060.

Figure 23:
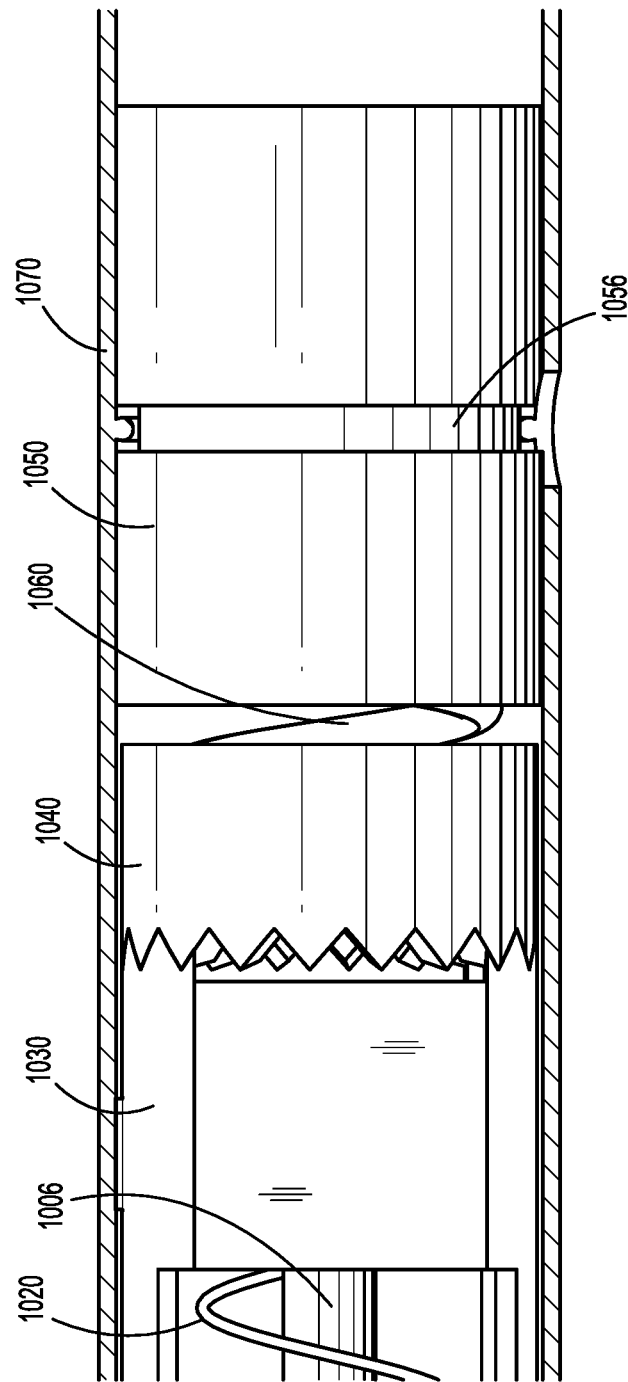
FIG. 23 is a cross-sectional view of a portion of the end effector of FIGS. 21 and 22.

As shown in FIG. 23, prior to use, a portion of proximal notch 1072 is longitudinally aligned with groove 1056 of drive element 1050 such that a shipping wedge (not shown) can extend through proximal notch 1072 and into engagement with groove 1056. The engagement between drive element 1050, second biasing element 1060, clutch 1040, and clevis 1030 is also shown in FIG. 23. As shown, second biasing element 1060 is disposed between drive element 1050 and clutch 1040, thus transferring rotational movement from drive element 1050 (and drive rod 150, as discussed above) to clutch 1040. Additionally, second biasing element 1060 enacts a distal force onto clutch 1040 to help maintain engagement between teeth 1044 of clutch 1040 and teeth 1038 of clevis 1030. Accordingly, rotation of clutch 1040 results in a corresponding rotation of clevis 1030.

Figure 24:
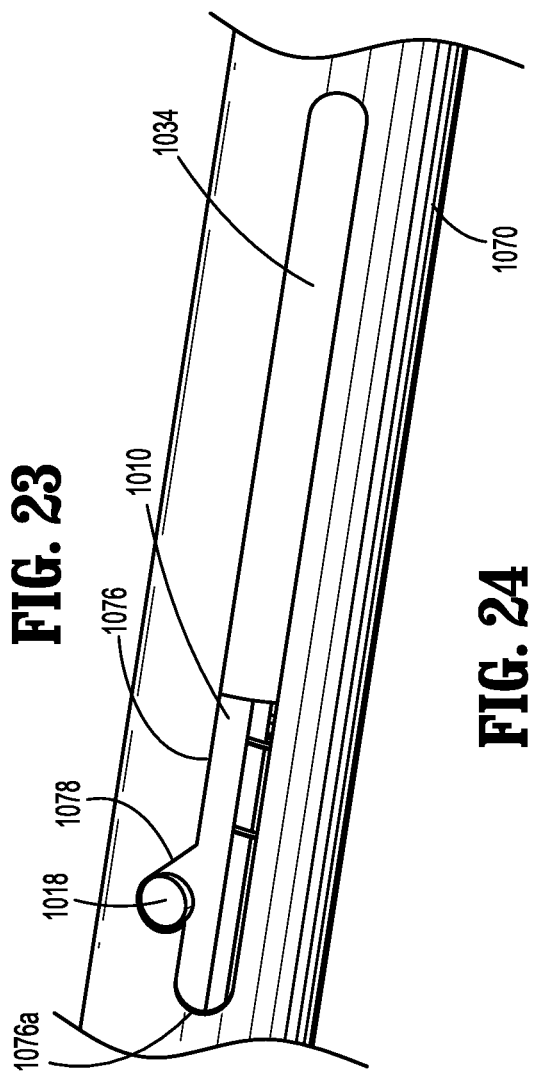
FIG. 24 is a perspective view of a portion of the end effector of FIGS. 21-23.
Figure 30:
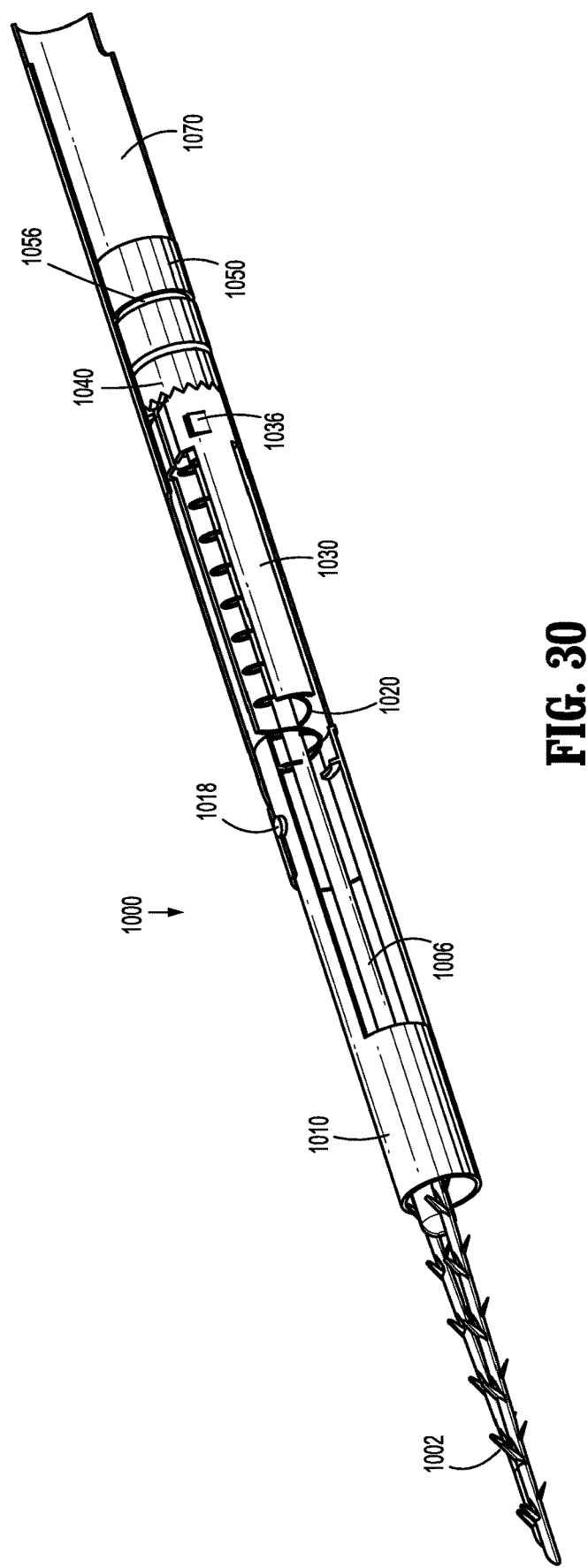
FIG. 30 is a perspective view of portions of the end effector of FIGS. 21-27 and with a needle in an advanced position.

With particular reference to FIG. 24, prior to use, tab 1018 of cover 1010 of end effector 1000 is disposed within angled slot 1078 of longitudinal groove 1076 of outer tube 1070. The engagement between tab 1018 and angled slot 1078 prevents cover 1010 from distally advancing with respect to outer tube 1070. In this position, cover 1010 is in its distal-most position where it radially surrounds distal tip 1008 of needle 1006 and barbed suture 1002.

In use, in response to at least a partial actuation of the trigger, the drive rod 150 rotates, as discussed above. Rotation of the drive rod results in a corresponding rotation of drive element 1050, clutch 1040, and clevis 1030. A predetermined amount of rotation (e.g., about) 90° of clevis 1030 causes flange 1036 of clevis 1030 to rotate in the general direction of arrow "FLA" from a first position within cutout 1074 of outer tube 1070, to a second position where flange 1036 engages a lateral wall 1074a of cutout 1074 of outer tube 1070 (see FIG. 27). Engagement between flange 1036 and lateral wall 1074a prevents continued rotation of clevis 1030 with respect to outer tube 1070 in the direction of arrow "FLA." Accordingly, when clevis 1030 continues to rotate in the direction of arrow "FLA" (e.g., in response to continued or additional actuation of the trigger), outer tube 1070 also rotates in the direction of arrow "FLA" with respect to cover 1010.

Rotation of outer tube 1070 in the direction of arrow "FLA" with respect to cover 1010 causes angled slot 1078 of outer tube 1070 to disengage from tab 1018 of cover 1010, which causes tab 1018 of cover 1010 to be within longitudinal groove 1076 of outer tube 1070. When tab 1018 of cover 1010 is within longitudinal groove 1076 of outer tube 1070, cover 1010 is in an unlocked position.

Next, a user presses a distal tip of surgical device 100 against tissue and/or mesh to emplace barbed suture 1002 at least partially therein and/or therethrough. More particularly, the user pushes a distal edge 1010a of cover 1010 against the tissue/mesh, which causes cover 1010 to move proximally with respect to outer tube 1070 against the bias of first biasing element 1020. As cover 1010 moves proximally, tab 1018 of cover 1010 travels proximally within longitudinal groove 1076 of outer tube 1070. The proximal movement of cover 1010 exposes barbed suture 1002 and distal tip 1008 of needle 1006, at least portions of which extend distally beyond outer tube 1070, and enables barbed suture 1002 and distal tip 1008 to penetrate the tissue/mesh.

As the user moves the surgical device 100 proximally (e.g., after barbed suture 1002 has been emplaced in tissue/mesh), first biasing element 1020 urges cover 1010 distally with respect to outer tube 1070. Cover 1010 continues to move distally while tab 1018 of cover 1010 travels within longitudinal groove 1076 of outer tube 1070 until tab 1018 contacts a distal edge 1076a of longitudinal groove 1076, preventing further distal movement of cover 1010 with respect to outer tube 1070 (see FIGS. 31 and 32). Further, as tab 1018 of cover 1010 contacts distal edge 1076a of longitudinal groove 1076, at least one proximal finger 1019 of cover 1010 enters an aperture 1071 of outer tube 1070 (e.g., in response to a radial outward bias of arms 1014), thus effectively locking the longitudinal position of cover 1010 with respect to outer tube 1070 (see FIGS. 31 and 33).

Folding Safety Cover

Figure 35:
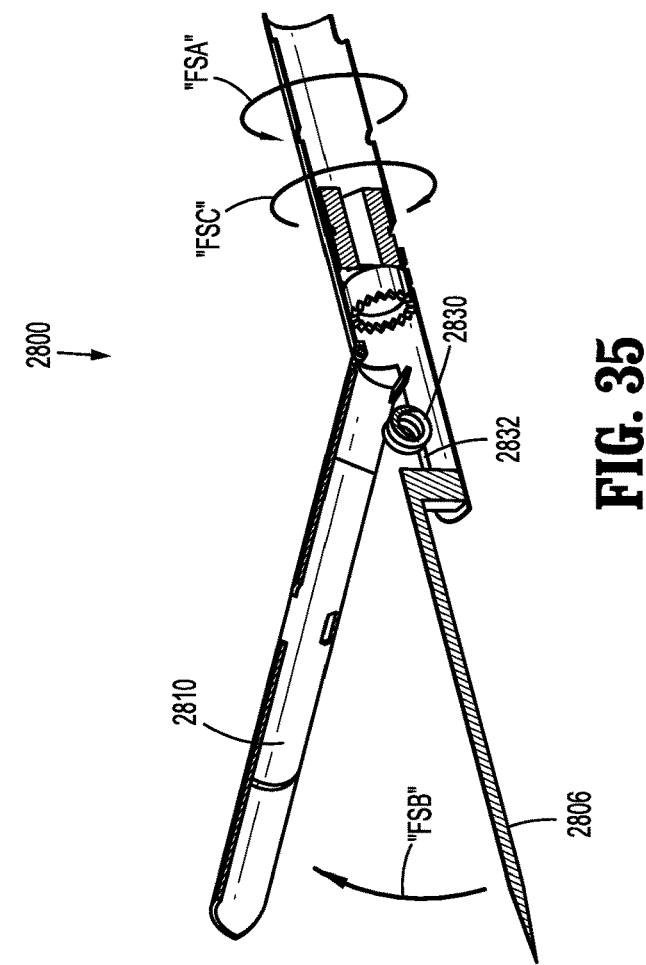
FIGS. 35 and 36 are cut-away views of portions of the end effector of FIG. 34.
Figure 34:
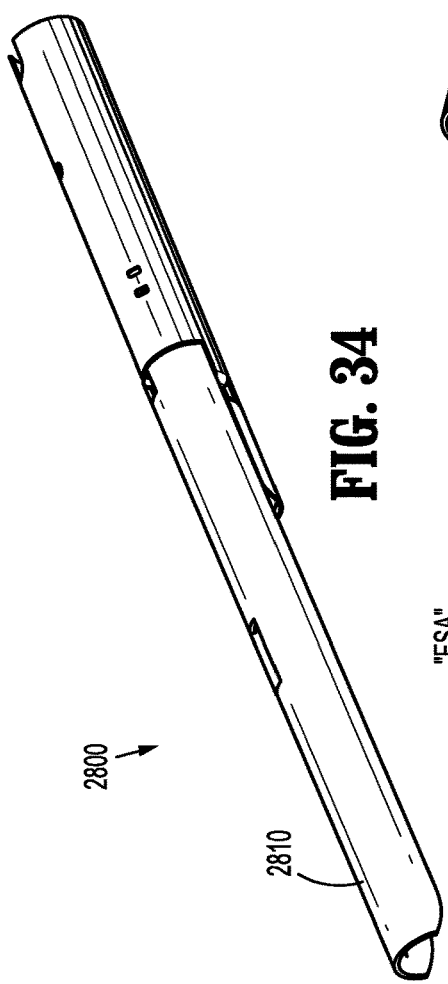
FIG. 34 is a perspective view of an end effector in accordance with embodiments of the present disclosure.

With reference to FIGS. 34-37, a safety cover assembly 2800 for use with various end effectors disclosed herein is shown. A cover 2810 of safety cover assembly 2800 is configured to pivot between a first position where safety cover 2800 helps prevent unintentional contact with a needle 2806 (FIG. 34), and a second position where safety cover 2800 allows needle 2806 to be driven into tissue (FIG. 35).

Figure 36:
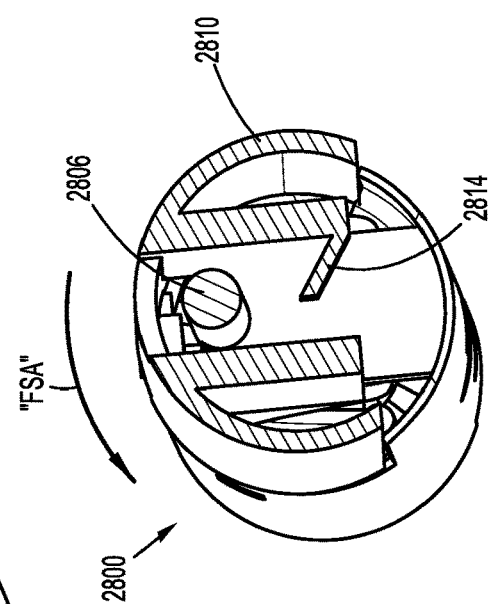
Figure 37:
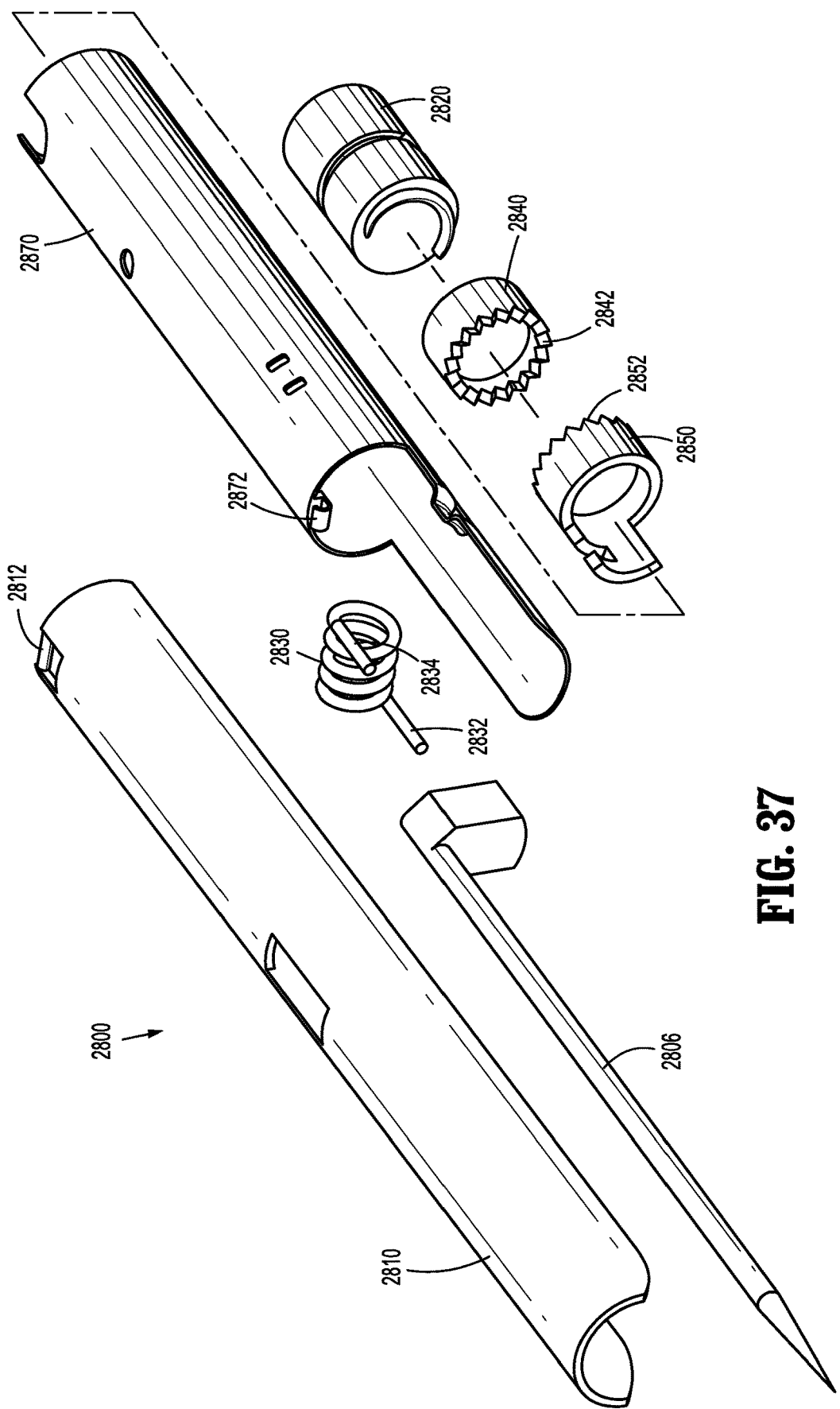
FIG. 37 is an assembly view of the end effector of FIGS. 34-36.
Figure 38:
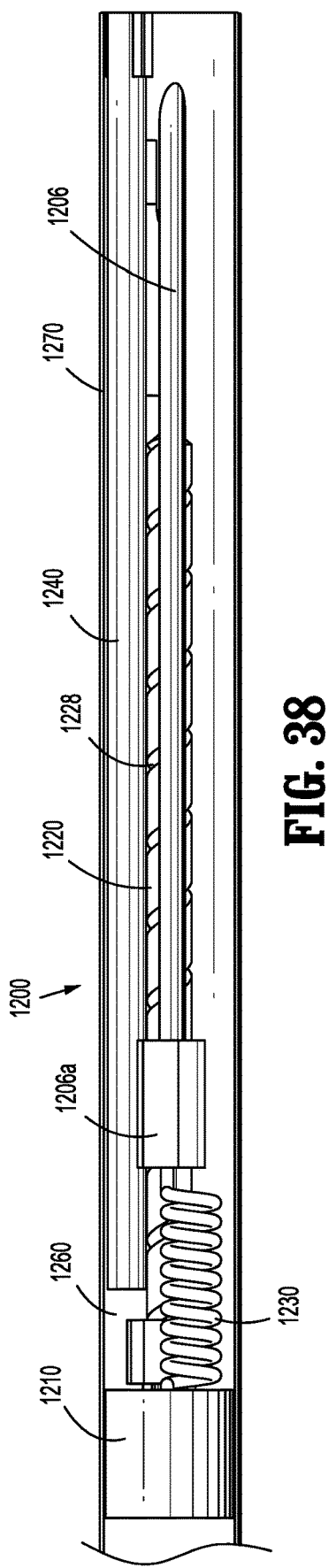
FIG. 38 is a cross-sectional view of an end effector in accordance with embodiments of the present disclosure.
Figure 39:
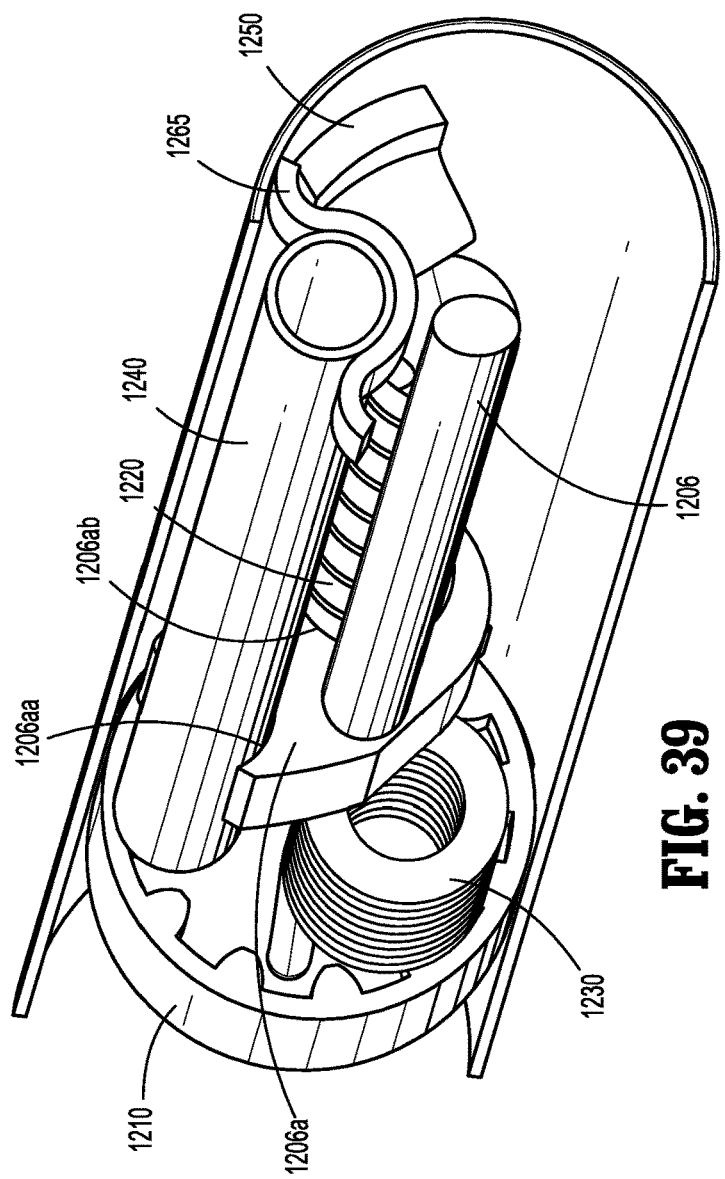
FIG. 39 is a perspective view of a portion of the end effector of FIG. 38.

With particular reference to FIG. 37, safety cover assembly 2800 includes cover 2810, a drive member 2820, a biasing member 2830, a gear 2840, a clutch 2850, and an outer tube 2870. Cover 2810 includes a proximal lip 2812, and an angled blocking portion 2814 (FIG. 36). Proximal lip 2812 is configured to pivotably engage a distal finger 2872 of outer tube 2870 to facilitate pivotal movement therebetween. Blocking portion 2814 of cover 2810 is configured to selectively engage a portion of needle 2806 and/or clutch 2850. The engagement between blocking portion 2814 and needle 2806 and/or clutch 2850 restricts the biasing force supplied by biasing member 2830.

Biasing member 2830 of cover assembly 2800 includes a first portion 2832 engaged with (e.g., affixed to) a proximal portion of needle 2086, and a second portion 2834 engaged with (e.g., affixed to) a proximal portion of cover 2810. Biasing member 2830 is configured to bias cover 2810 away from needle 2806 toward its second position (FIG. 35). As noted above, the engagement between blocking portion 2814 of cover 2810 and needle 2806 and/or clutch 2850 resists the biasing force supplied by biasing member 2830.

Drive member 2820, gear 2840, and clutch 2850 of cover assembly 2800 are disposed radially within outer tube 2870. Drive member 2820 is mechanically engaged (e.g., operatively coupled, directly affixed, etc.) to drive rod 150 of surgical device 100 of the present disclosure. Accordingly, rotation of the drive rod 150 in the general direction of arrow "FSA" results in a corresponding rotation of drive member 2820. Additionally, drive member 2820 is configured to engage gear 2840 such that rotation of drive member 2820 in the general direction of arrow "FSA" causes a corresponding rotation of gear 2840 in the general direction of arrow "FSA." Further, gear 2840 is configured to engage clutch 2850 such that rotation of gear 2840 in the general direction of arrow "FSA" causes a corresponding rotation of clutch 2850.

With reference to FIGS. 35-37, clutch 2850 of cover assembly 2800 is configured to engage a portion of cover 2810, such that rotation of clutch 2850 in the general direction of arrow "FSA" causes a corresponding rotation of cover 2810 in the general direction of arrow "FSA." With particular reference to FIG. 36, rotation of cover 2810 in the general direction of arrow "FSA" causes blocking portion 2814 of cover 2810 to rotate with respect to needle 2806, such that blocking portion 2814 no longer resists the force exerted by biasing member 2830 onto cover 2810. Accordingly, rotation of drive rod 150 in the general direction of arrow "FSA" causes a corresponding rotation of drive member 2820, gear 2840, clutch 2850 and cover 2810, thus causing cover 2810 to pivot in the general direction of arrow "FSB" (FIG. 35) toward its second position, since blocking portion 2814 no longer resists the force exerted by biasing member 2830 onto cover 2810. Additionally, proximal teeth 2852 of clutch 2850, which mate with distal teeth 2842 of gear 2840, are configured to skip following additional rotation of gear 2840 after cover 2810 moves toward its second position.

When cover 2810 is in its second position, needle 2806 is exposed and is able to be driven into tissue, for example. If a user desires to move cover 2810 back toward its first position, the user may use a secondary instrument or the user's hand, to pivot cover 2810 toward its first position against the bias of biasing member 2830. The cover 2810 can be rotated in the general direction of arrow "FSC" (FIG. 35) such that blocking portion 2814 engages needle 2806 and resists the force exerted by biasing member 2830.

Gear Design

Referring now to FIGS. 38-45, an embodiment of an end effector 1200 including a gear design assembly is shown. End effector 1200 is configured for use in connection with surgical device 100. Generally, end effector 1200 is configured to advance a needle 1206 towards tissue. While FIGS. 38-45 illustrate a particular type of needle 1206, end effector 1200 may be used with different types of needles.

Figure 40:
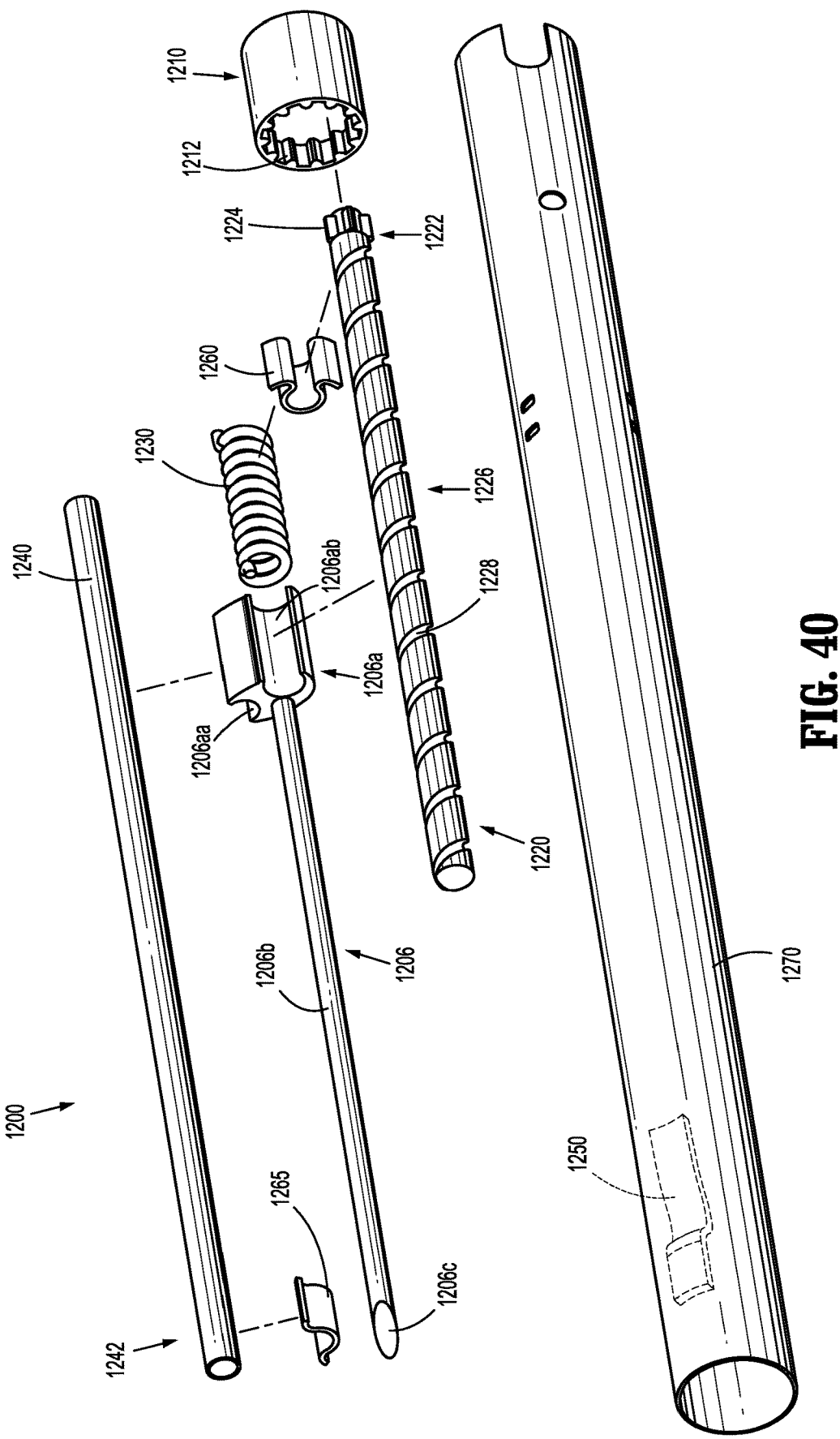
FIG. 40 is an assembly view of the end effector of FIGS. 38-39.

With particular reference to FIG. 40, end effector 1200 includes a drive gear 1210, a drive shaft 1220, a retraction spring 1230, a guide shaft 1240, a deflection member 1250, a proximal support 1260, a distal support 1265, and an outer tube 1270.

Drive gear 1210 is mechanically engaged (e.g., operatively coupled, directly affixed, etc.) to drive rod 150 of surgical device 100 of the present disclosure. Rotation of drive rod 150 in the general direction of arrow "GDA" in FIG. 41 results in a corresponding rotation of drive gear 1210. Drive gear 1210 includes a plurality of teeth 1212 adjacent its distal end, and is rotationally supported within outer tube 1270.

Drive shaft 1220 includes a proximal portion 1222 including a plurality of teeth 1224, and an elongated portion 1226 including a helical groove 1228 therein. Teeth 1224 are configured to rotationally engage teeth 1212 of drive gear 1210, such that rotation of drive gear 1210 in the general direction of arrow "GDA" causes a corresponding rotation of drive shaft 1220, depicted by arrow "GDB" in FIG. 42. Elongated portion 1226 of drive shaft 1220 is configured to engage a portion of needle 1206, such that rotation of elongated portion 1226 causes longitudinal translation of needle 1206, as discussed below. Proximal support 1260 of end effector 1200 engages a portion of drive shaft 1220 to help support drive shaft 1220 within outer tube 1270.

Guide shaft 1240 of end effector 1200 is longitudinally and rotationally fixed within outer tube 1270, and is configured to engage a portion of needle 1206 to help guide needle 1206 as needle 1206 travels distally and proximally with respect to outer tube 1270. A distal portion 1242 of guide shaft 1240 is supported within outer tube 1270 by engaging distal support 1265.

Needle 1206 includes a proximal hub 1206a, an elongated portion 1206b extending distally from proximal hub 1206a, and a distal tip 1206c configured to pierce tissue. Proximal hub 1206a of needle 1206 includes a first longitudinal groove 1206aa and a second longitudinal groove 1206ab. First longitudinal groove 1206aa of proximal hub 1206a is configured to slidably engage guide shaft 1240. Second longitudinal groove 1206ab of proximal hub 1206a is configured to threadedly engage drive shaft 1220.

Retraction spring 1230 of end effector 1200 is engaged with (e.g., affixed to) a proximal end of needle 1206 and a portion of drive gear 1210. Retraction spring 1230 of end effector 1200 is configured to bias needle 1206 proximally.

Deflection member 1250 of end effector 1200 extends radially inward from a distal portion of outer tube 1270, and is configured to cause proximal hub 1206a of needle 1206 to move laterally or radially, as discussed below.

Outer tube 1270 of end effector 1200 is configured for positioning radially outward of at least portions of needle 1206, drive gear 1210, drive shaft 1220, retraction spring 1230, guide shaft 1240, proximal support 1260, and distal support 1265.

Figure 41:
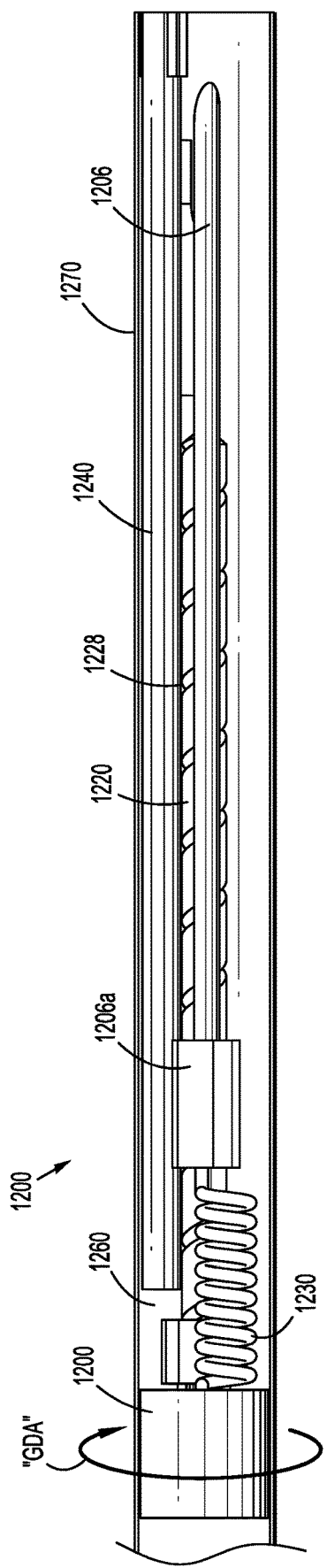
FIG. 41 is a cross-sectional view of the end effector of FIGS. 38-40.
Figure 42:
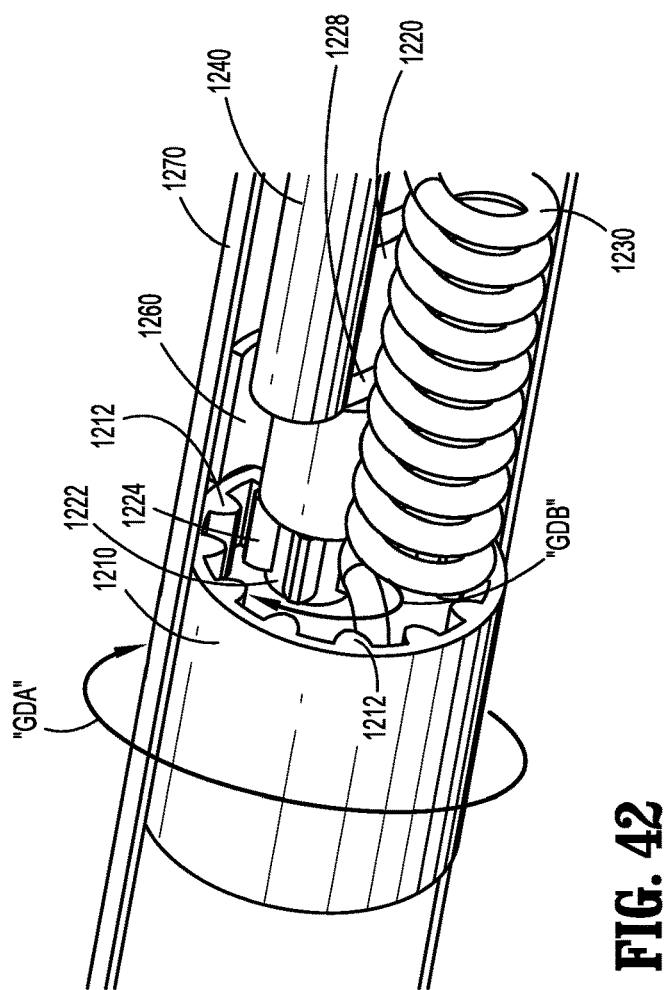
FIGS. 42-45 are perspective views of portions of the end effector of FIGS. 38-41 during various stages of operation.
Figure 43:
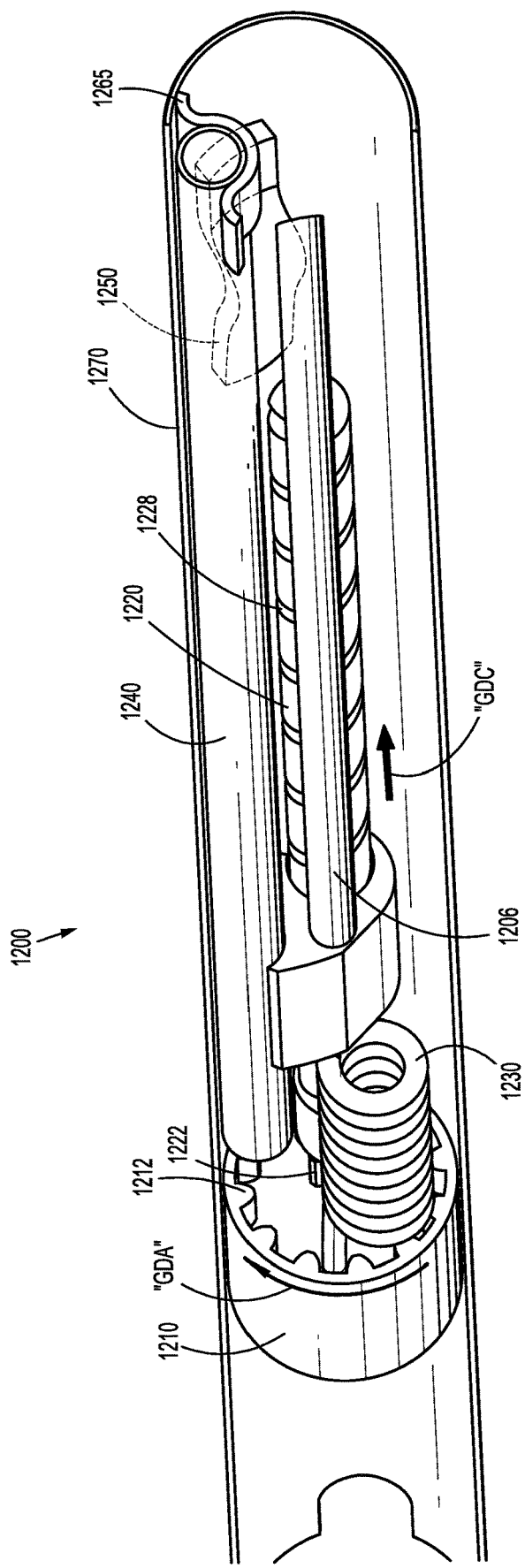
Figure 44:
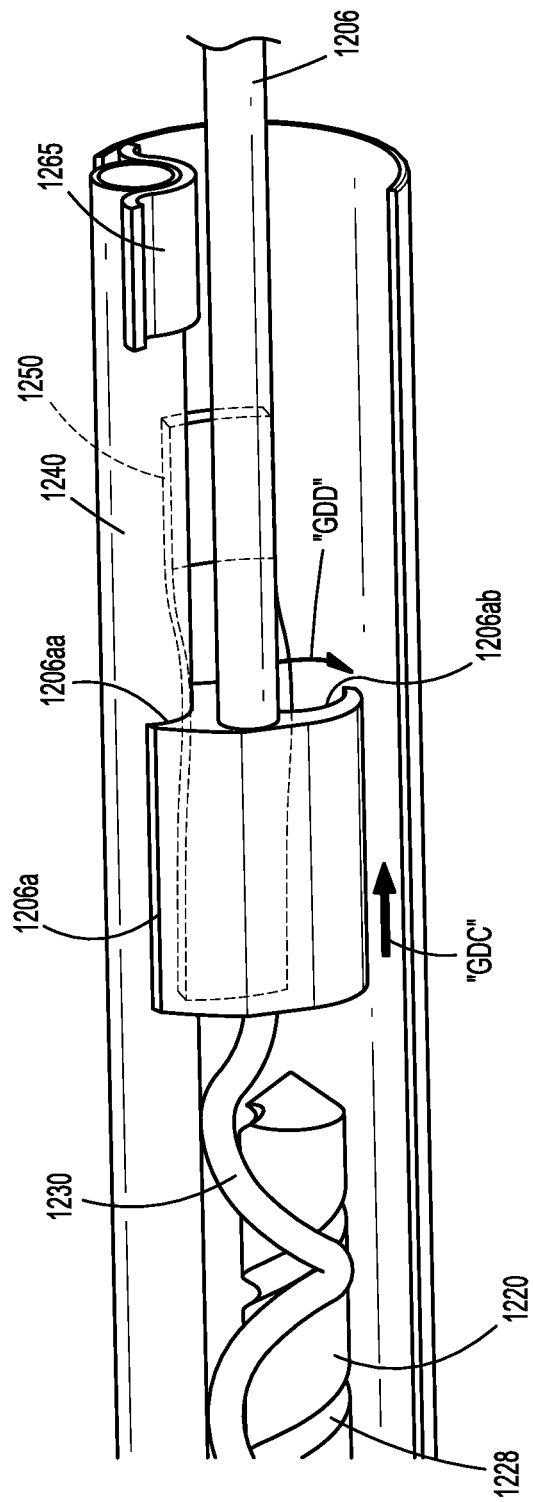
Figure 45:
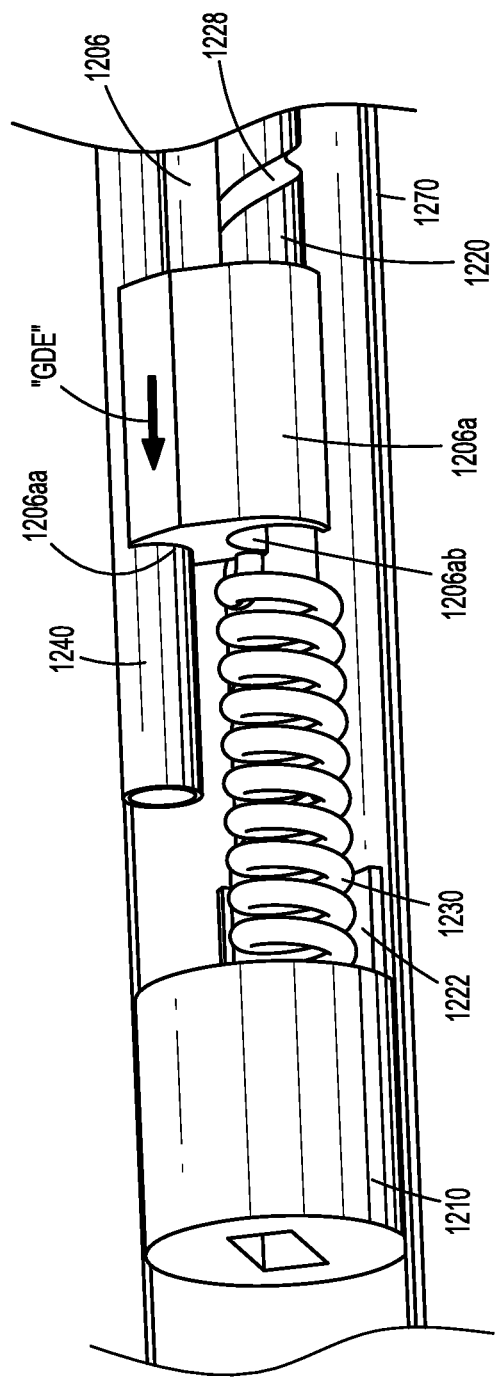

In use, in response to at least a partial actuation of the trigger of surgical device 100, drive rod 150 rotates, as discussed above. With reference to FIGS. 41-43, initial rotation of the drive rod 150 results in a corresponding rotation of drive gear 1210 of end effector 1200 with respect to outer tube 1270 in the general direction of arrow "GDA" in FIGS. 41 and 42. Due to the engagement between teeth 1212 of drive gear 1210 and teeth 1224 of drive shaft 1220, rotation of drive gear 1210 in the general direction of arrow "GDA" causes a corresponding rotation of drive shaft 1220 in the general direction of arrow "GDB" (see FIG. 42).

Rotation of drive shaft 1220 in the general direction of arrow "GDB" results in distal translation of needle 1206 in the general direction of arrow "GDC" in FIG. 43. In particular, second longitudinal groove 1206ab of proximal hub 1206a of needle 1206 includes a pin (not explicitly shown) extending radially therefrom, which engages helical groove 1228 of drive shaft 1220. Accordingly, as drive shaft 1220 rotates, the pin of second longitudinal groove 1206ab travels within helical groove 1228, and thus translates longitudinally. It is also envisioned that in lieu of or in addition to the pin, a thread feature engages helical groove 1228. Further, the engagement between first longitudinal groove 1206aa of proximal hub 1206a of needle 1206 and guide shaft 1240 helps ensure linear and longitudinal movement of needle 1206 with respect to outer tube 1270.

Continued rotation of drive gear 1210 in the general direction of arrow "GDA" causes continued distal advancement of needle 1206 until distal tip 1206c of needle 1206 extends a sufficient distance distally beyond a distal end of outer tube 1270. After a predetermined amount of rotation of drive gear 1210 and distal travel of needle 1206 (e.g., corresponding to when distal tip 1206c is sufficiently advanced within tissue), proximal hub 1206a of needle 1206 contacts deflection member 1250 (see FIG. 44). The contact or engagement between proximal hub 1206a and deflection member 1250, results in deflection member 1250 deflecting proximal hub 1206a in the general direction of arrow "GDD" in FIG. 44, such that second longitudinal groove 1206ab of proximal hub 1206a is pushed out of engagement from drive shaft 1220.

Disengagement between second longitudinal groove 1206ab of proximal hub 1206a and drive shaft 1220 results in the pin of second longitudinal groove 1206ab disengaging from helical groove 1228 of drive shaft 1220. Further, since the engagement between the pin and helical groove 1228 opposed the proximal force exerted by retraction spring 1230, and since the pin is no longer engaged with helical groove 1228, retraction spring 1230 pulls needle 1206 proximally in the general direction of arrow "GDE" in FIG. 45, thereby retracting needle 1206. Needle 1206 continues to retract proximally until it reaches the approximate position shown in FIG. 45.

Outside Tube—Cartridge Design

Referring now to FIGS. 46-56, an embodiment of an end effector 1300 including a carriage assembly is shown. End effector 1300 is configured for use in connection with surgical device 100. Generally, end effector 1300 is configured to advance a needle 1306 towards tissue. While FIGS. 46-56 illustrate a particular type of needle 1306, end effector 1300 may be used with different types of needles.

Figure 48:
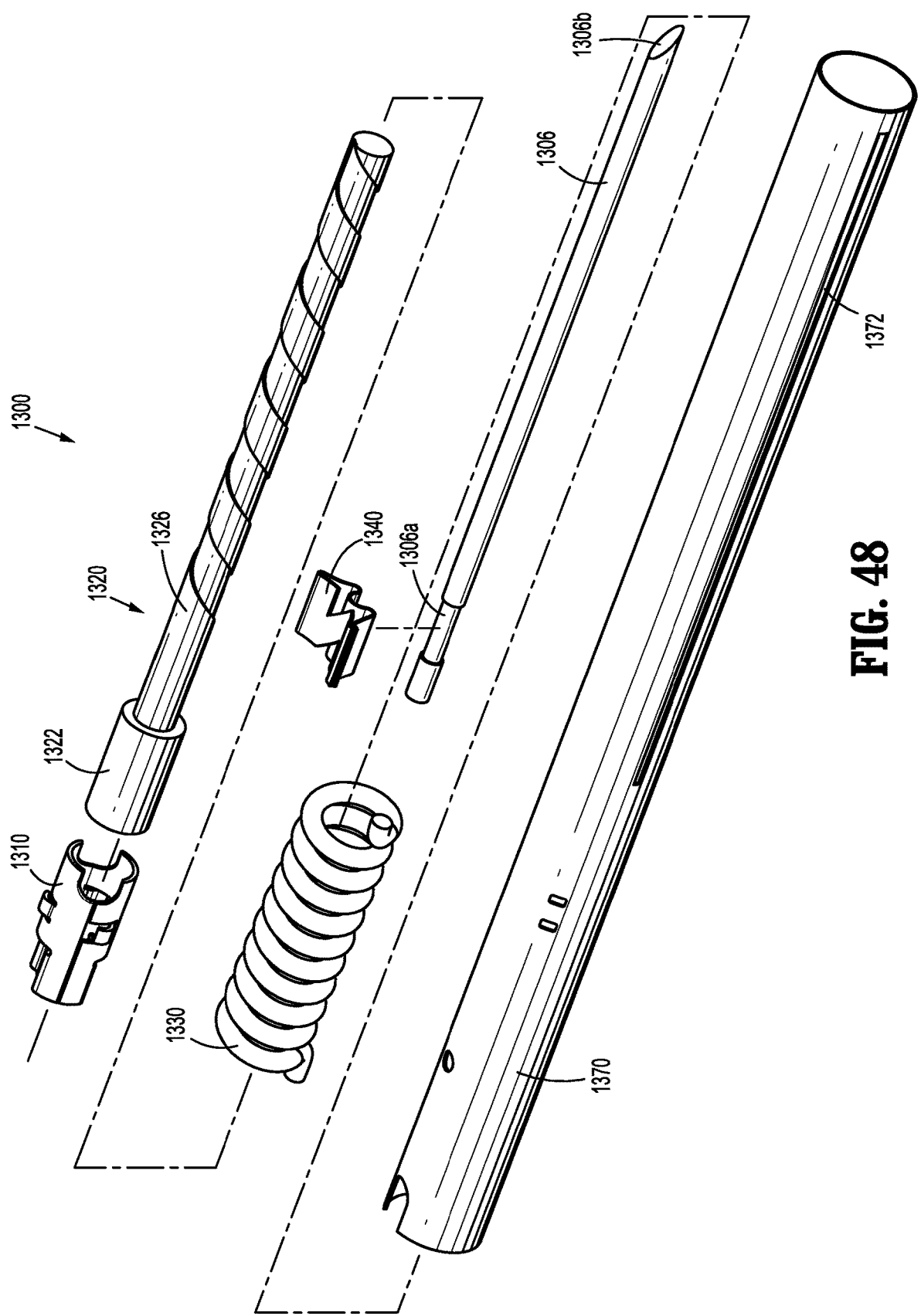
FIG. 48 is an assembly view of the end effector of FIGS. 46-47.
Figure 49:
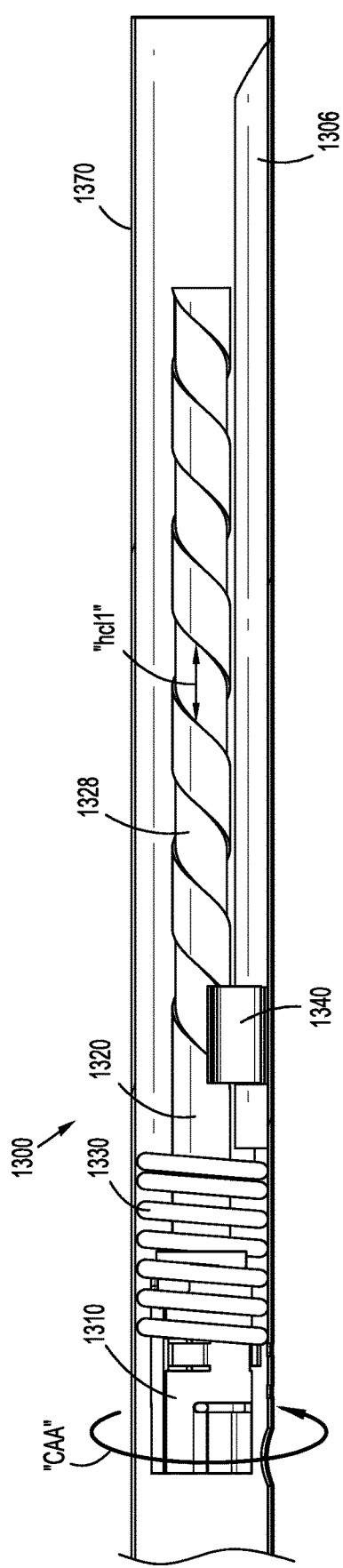
FIG. 49 is a side view of portions of the end effector of FIGS. 46-48.
Figure 51:
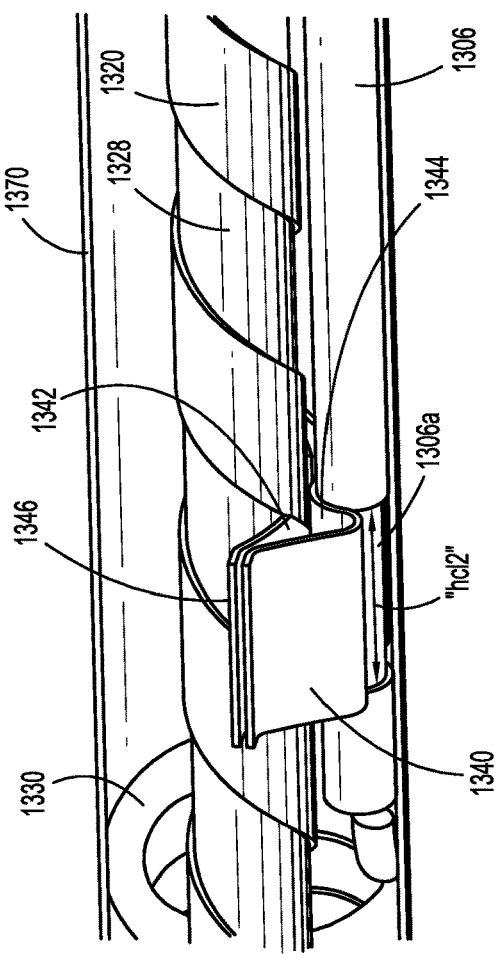
FIG. 51 is a perspective view of portions of the end effector of FIGS. 46-50.
Figure 50:
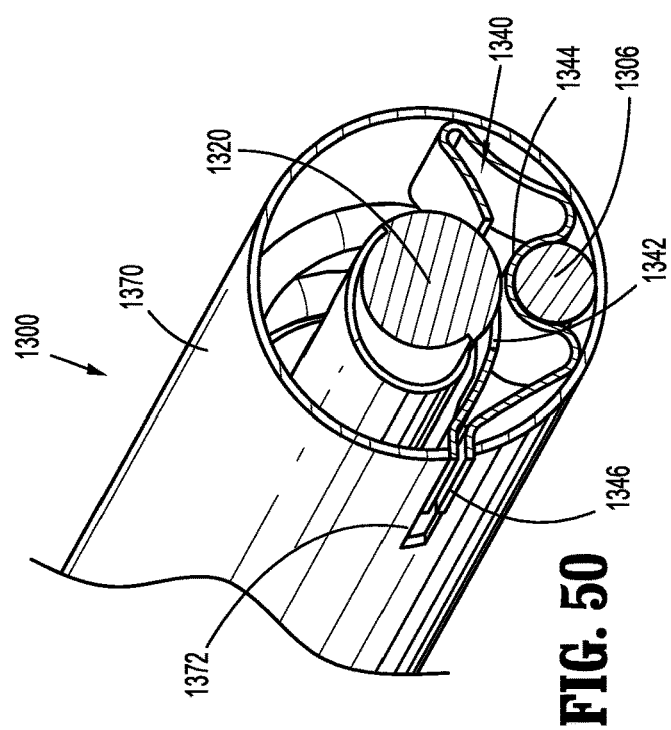
FIG. 50 is a cut-away view of the end effector of FIGS. 46-49.
Figure 57:
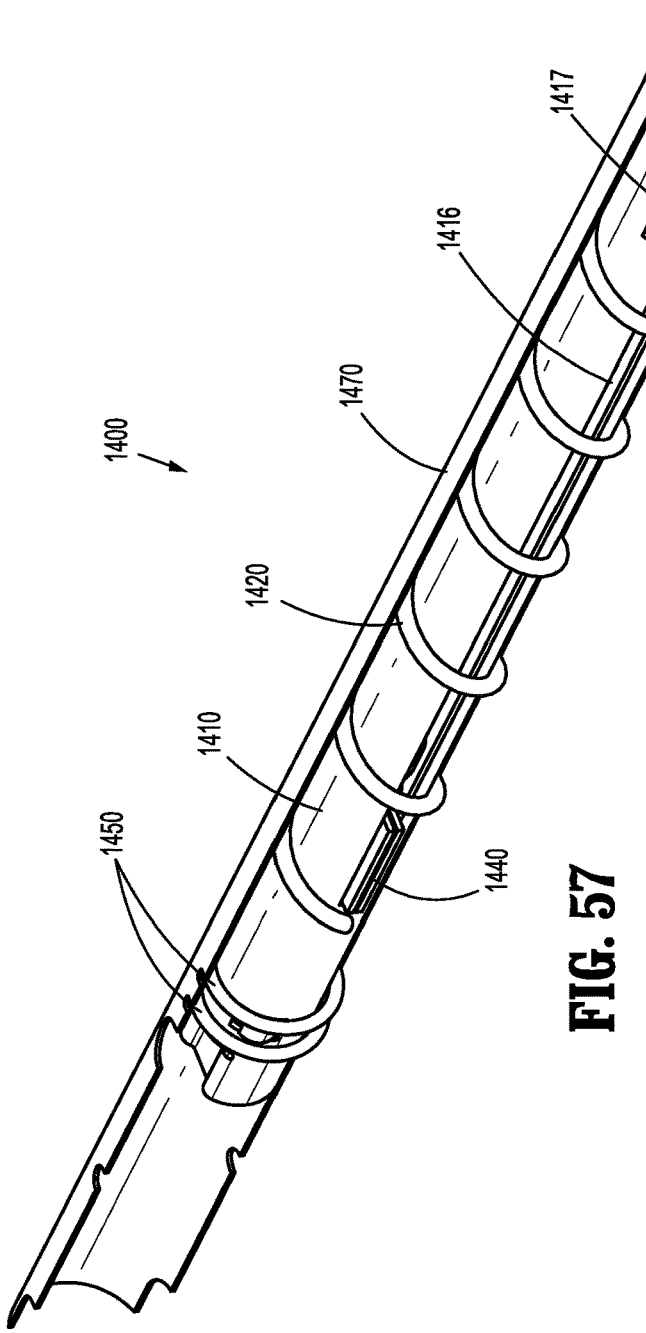
FIG. 57 is a perspective view of portions of an end effector in accordance with embodiments of the present disclosure.
Figure 58:
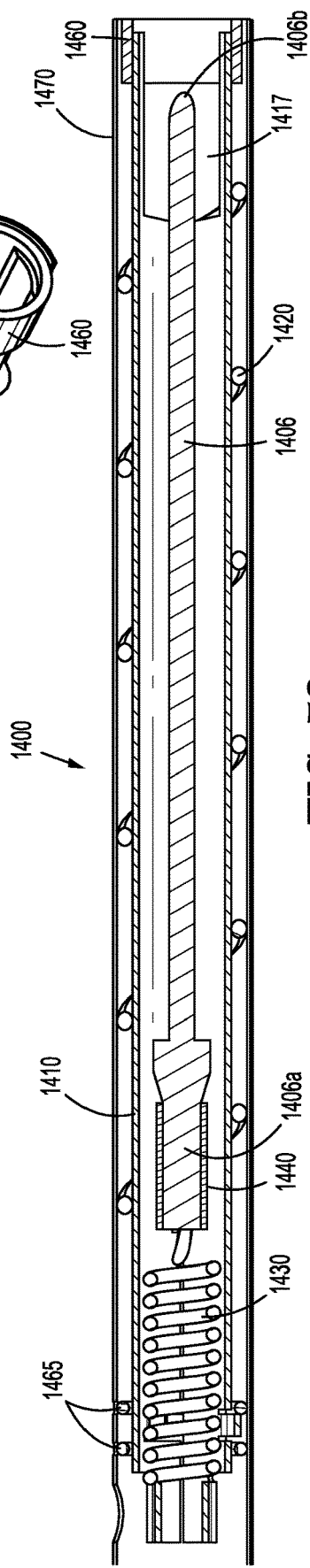
FIG. 58 is a cross-sectional view of the end effector of FIG. 57.

With particular reference to FIG. 48, end effector 1300 includes a drive assembly 1310, a drive shaft 1320, a retraction spring 1330, a carriage 1340, and an outer tube 1370

Drive assembly 1310 of end effector 1300 is mechanically engaged (e.g., operatively coupled, directly affixed, etc.) to drive rod 150 of surgical device 100 of the present disclosure. Rotation of drive rod 150 in the general direction of arrow "CAA" in FIG. 49 results in a corresponding rotation of drive shaft 1320.

Drive shaft 1320 of end effector 1300 includes a proximal hub 1322 and an elongated portion 1326 extending distally from proximal hub 1322. Proximal hub 1322 of drive shaft 1320 mechanically engages drive assembly 1310 and is rotationally fixed thereto such that rotation of drive assembly 1310 in the general direction of arrow "CAA" results in a corresponding rotation of drive shaft 1320 in the general direction of arrow "CAA." Elongated portion 1326 of drive shaft 1320 includes a helical channel 1328 therein. Elongated portion 1326 is configured to engage a portion of carriage 1340, such that rotation of elongated portion 1326 causes longitudinal translation of carriage 1340, as discussed below.

Needle 1306 includes a recessed portion 1306a, and a distal tip 1306b configured to pierce tissue. Recessed portion 1306a is configured to engage a portion of carriage 1340.

Retraction spring 1330 of end effector 1300 is engaged with (e.g., affixed to) a proximal end of needle 1306 and a portion of drive assembly 1310. Retraction spring 1330 is configured to bias needle 1306 proximally.

Outer tube 1370 of end effector 1300 is configured for positioning radially outward of at least portions of needle 1306, drive assembly 1310, drive shaft 1320, retraction spring 1330, and carriage 1340. Outer tube 1370 includes an elongated slot 1372 configured to slidingly engage a portion of carriage 1340.

Carriage 1340 of end effector 1300 includes a first engagement section 1342 configured to engage helical channel 1328 of drive shaft 1320, a second engagement section 1344 configured to engage recessed portion 1306a of needle 1306, and an extension 1346 configured to slidingly engage elongated slot 1372 of outer tube 1370. First engagement section 1342 includes a length in the longitudinal direction that is substantially the same as or slightly smaller than a longitudinal length "hcl1" (see FIG. 49) of helical channel 1328, thereby facilitating a frictional engagement therebetween. Second engagement section 1344 is arcuate, and includes the same or a similar radius of curvature as recessed portion 1306a of needle 1306. Second engagement section 1344 also includes a length in the longitudinal direction that is substantially the same as or slightly smaller than a longitudinal length "hcl2" (see FIG. 51) of recessed portion 1306a. Extension 1346 of carriage 1340 extends at least partially within or at least partially through (e.g., radially outward of) elongated slot 1372 of outer tube 1370, and is configured to longitudinally travel along elongated slot 1372 as carriage 1340 translates distally and proximally with respect to outer tube 1370.

In use, in response to at least a partial actuation of the trigger of surgical device 100, drive rod 150 rotates, as discussed above. With reference to FIGS. 49-53, initial rotation of the drive rod 150 results in a corresponding rotation of drive assembly 1310 and drive shaft 1320 with respect to outer tube 1370 in the general direction of arrow "CAA" in FIGS. 49 and 53. Due to the engagement between helical channel 1328 of drive shaft 1320 and first engagement section 1342 of carriage 1340, rotation of drive assembly 1310 and drive shaft 1320 in the general direction of arrow "CAA" results in distal translation of carriage 1340, which is guided by the engagement between extension 1346 and elongated slot 1372.

As carriage 1340 translates distally with respect to outer tube 1370, needle 1306 also travels distally in the general direction of arrow "CAB" in FIG. 53. In particular, the engagement between second engagement section 1344 of carriage 1340 and recessed portion 1306a of needle 1306 causes needle 1306 to travel distally as carriage 1340 travels distally. As noted above, the engagement between extension 1346 of carriage 1340 and elongated slot 1372 of outer tube 1370 helps guide the longitudinal translation of carriage 1340. Thus, rotation of drive assembly 1310 and drive shaft 1320 in the general direction of arrow "CAA" causes distal translation of carriage 1340 and needle 1306 in the general direction of arrow "CAB."

Continued rotation of drive assembly 1310 and drive shaft 1320 in the general direction of arrow "CAA" causes continued distal advancement of needle 1306 until distal tip 1306b of needle 1306 extends a sufficient distance distally beyond a distal end of outer tube 1370. With particular reference to FIGS. 54-56, after a predetermined amount of rotation of drive assembly 1310 and drive shaft 1320, and distal travel of needle 1306 (e.g., corresponding to when distal tip 1306b is sufficiently advanced within tissue), carriage 1340 travels distally of drive shaft 1320, thus disengaging therefrom. This disengagement between first engagement section 1342 of carriage 1340 and drive shaft 1320 causes carriage 1340 to move laterally, or radially inward, in the general direction of arrow "CAC" in FIG. 54, in response to the natural deflection of carriage 1340, for instance. Additionally, with particular reference to FIG. 55, a distal portion of elongated slot 1372 includes a height "h1" that is greater than a height "h2" of portion of elongated slot 1372 disposed proximally thereof. The increased height "h1" at the distal portion of elongated slot 1372 helps prevent extension 1346 or carriage 1340 from becoming wedged within elongated slot 1372, which may hinder the lateral movement of carriage 1340 with respect to drive shaft 1320. The increased height "h1" also helps allow a greater freedom of movement of carriage 1340 after ending its travel with respect to drive shaft 1320, which may also help distal translation of needle 1306.

The lateral movement of carriage 1340 with respect to drive shaft 1320 also causes second engagement section 1344 of cartridge 1340 to disengage from recessed portion 1306a of needle 1306. Since the engagement between carriage 1340 and needle 1306 is opposed the proximal force exerted by retraction spring 1330, and since the carriage 1340 is no longer engaged with needle 1306, retraction spring 1330 pulls needle 1306 proximally in the general direction of arrow "CAD" in FIG. 56, thereby retracting needle 1306. Needle 1306 continues to retract proximally until it reaches the approximate position shown in FIG. 56.

Carriage Driver

Referring now to FIGS. 57-64, an embodiment of an end effector 1400 including a carriage assembly is shown. End effector 1400 is configured for use in connection with surgical device 100. Generally, end effector 1400 is configured to advance a needle 1406 towards tissue. While FIGS. 57-64 illustrate a particular type of needle 1406, end effector 1400 may be used with different types of needles.

Figure 59:
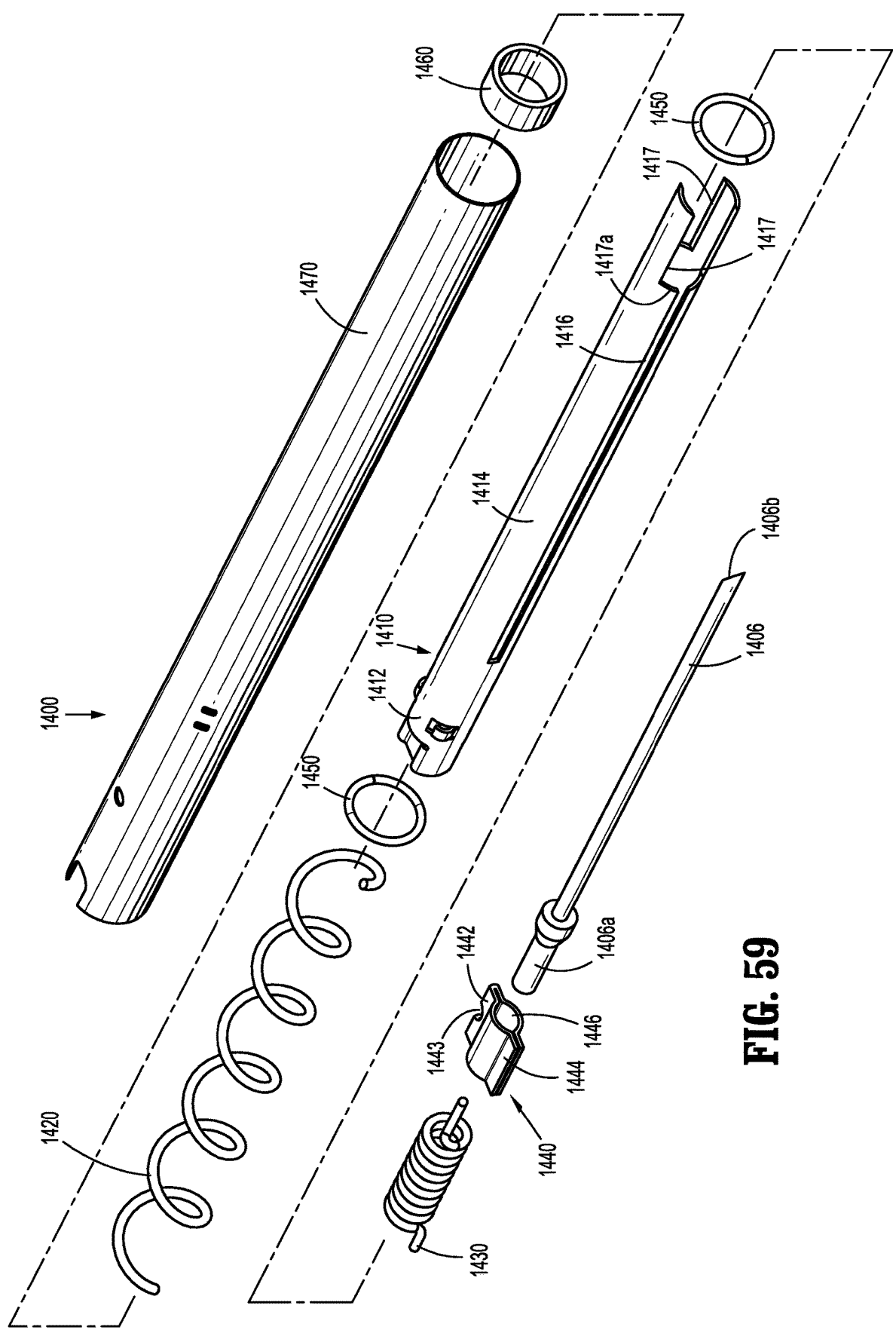
FIG. 59 is an assembly view of the end effector of FIGS. 57-58.

With particular reference to FIG. 59, end effector 1400 includes a drive assembly 1410, a helix or coil assembly 1420, a retraction spring 1430, a carriage 1440, a pair of rings, 1450, a distal stop 1460, and an outer tube 1470.

Drive assembly 1410 is mechanically engaged (e.g., operatively coupled, directly affixed, etc.) to drive rod 150 of surgical device 100 of the present disclosure. Rotation of drive rod 150 in the general direction of arrow "CDA" in FIG. 60 results in a corresponding rotation of drive assembly 1410. Drive assembly 1410 includes a proximal hub 1412 and a pair of arms 1414 extending therefrom. Arms 1414 of drive assembly 1410 define a pair of slots 1416 therebetween. Slots 1416 are configured to slidingly receive portions of carriage 1440, as discussed below.

Needle 1406 includes a proximal portion 1406a, and a distal tip 1406b configured to pierce tissue. Proximal portion 1406a of needle 1406 is configured to engage a portion of carriage 1440, as discussed below.

Retraction spring 1430 of end effector 1400 is engaged with (e.g., affixed to) a proximal end of needle 1406 and a portion of drive assembly 1410. Retraction spring 1430 is configured to bias needle 1406 proximally.

Figure 60:
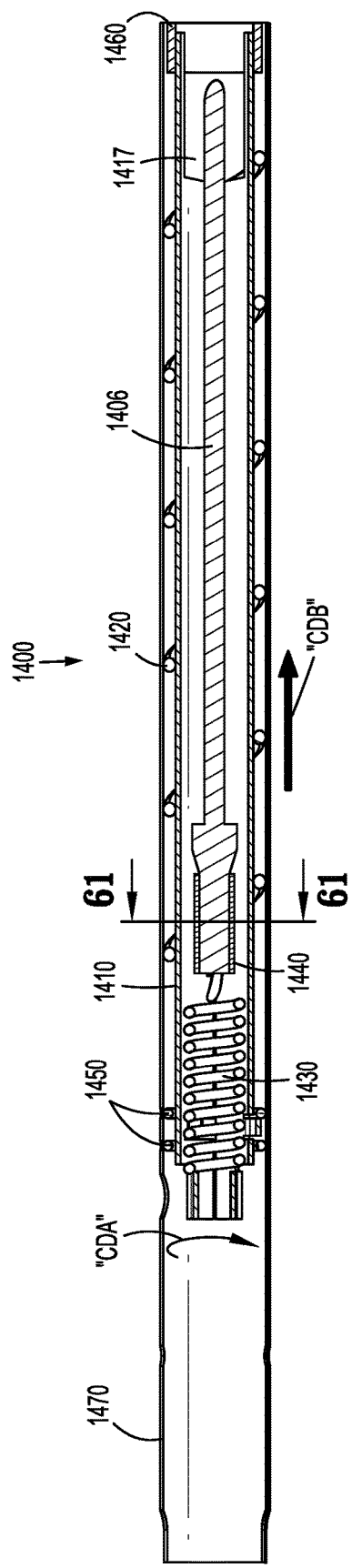
FIG. 60 is a cross-sectional view of the end effector of FIGS. 57-59.
Figure 61:
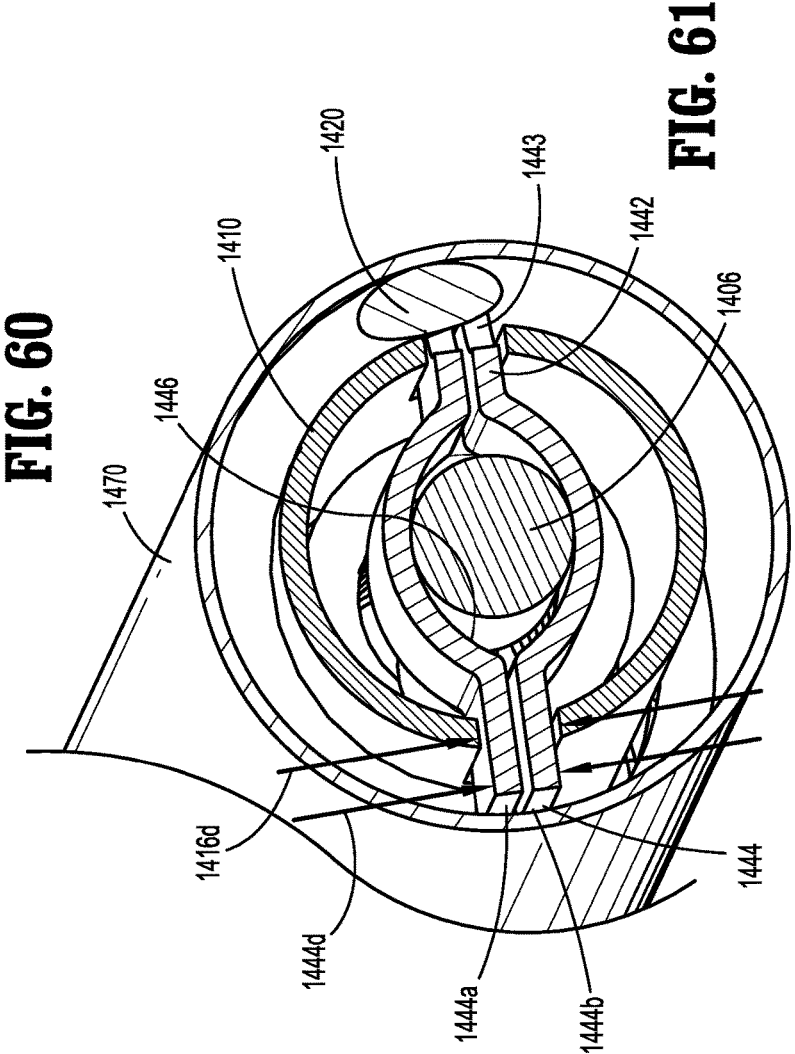
FIG. 61 is a cut-away view of the end effector of FIGS. 57-60.
Figure 62:
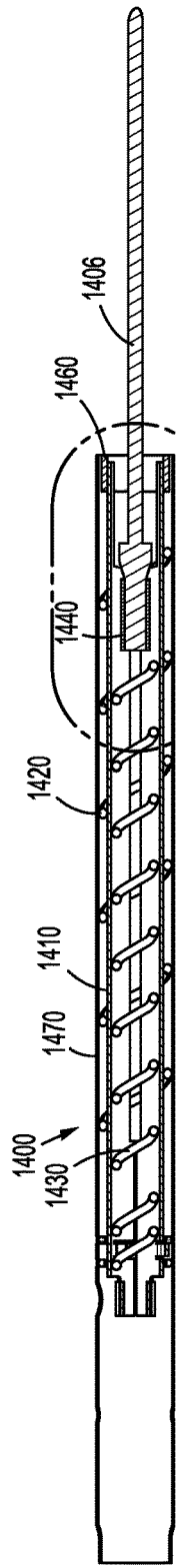
FIG. 62 is a cross-sectional view of the end effector of FIGS. 57-61 illustrating a needle in an advanced position.
Figure 63:
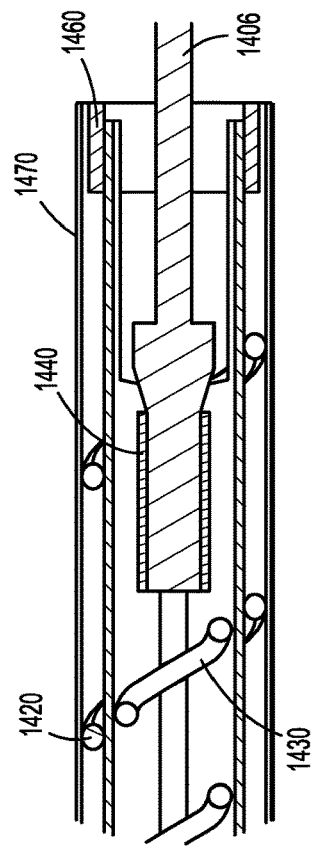
FIG. 63 is an enlarged view of the area of detail indicated in FIG. 62.

With particular reference to FIG. 60, rings 1450 (e.g., O-rings) of end effector 1400 are positioned radially outward of a proximal portion drive assembly 1410. Rings 1450 help maintain appropriate spacing between drive assembly 1410 and outer tube 1470, and help facilitate rotation of drive assembly 1410 with respect to outer tube 1470.

Outer tube 1470 of end effector 1400 is configured for positioning radially outward of at least portions of needle 1406, drive assembly 1410, retraction spring 1430, and carriage 1440. Distal stop 1460 of end effector 1400 is secured within a distal portion of outer tube 1470, and is configured to prevent carriage 1440 from distally exiting outer tube 1470.

Helix or coil assembly 1420 of end effector 1400 extends between a proximal portion of drive assembly 1410 and distal stop 1460, and is disposed radially within outer tube 1470. Helix or coil assembly 1420 is stationary with respect to outer tube 1470, and is configured to engage a portion of carriage 1440 such that carriage 1440 can move longitudinally and rotationally within outer tube 1470 and with respect to outer tube 1470.

Carriage 1440 of end effector 1400 is generally eye-lid or ovoid shaped including a first lateral portion 1442, a second lateral portion 1444, and defining a central aperture 1446 configured to engage proximal portion 1406a of needle 1406. It is envisioned that carriage 1440 is made from a single piece of material, which is folded at one of the first lateral portion 1442 (as shown) or second lateral portion 1444. Each of first lateral portion 1442 and second lateral portion 1444 of carriage 1440 is configured to slidingly engage slot 1416 of drive assembly 1410. Additionally, first lateral portion 1442 includes a notch 1443 therein which is configured to engage helix or coil assembly 1420, and second lateral portion 1444 includes a first leg 1444a and a second leg 1444b. Carriage 1440 is configured to move rotationally and longitudinally with respect to outer tube 1470.

In use, in response to at least a partial actuation of the trigger of surgical device 100, drive rod 150 rotates, as discussed above. With reference to FIGS. 60-63, initial rotation of the drive rod 150 results in a corresponding rotation of drive assembly 1410, carriage 1440 and needle 1406 with respect to outer tube 1470 in the general direction of arrow "CDA" in FIG. 60. Due to the engagement between helix or coil assembly 1420 and notch 1443 of first lateral portion 1442 of carriage 1440, rotation of carriage 1440 in the general direction of arrow "CDA" results in distal translation of carriage 1440 and needle 1406 with respect to outer tube 1470 in the general direction of arrow "CDB" in FIG. 60. Additionally, the engagement between notch 1443 and helix or coil assembly 1420 resists the proximal biasing force provided by retraction spring 1430. The distal translation of carriage 1440 is guided by the engagement between first lateral portion 1442 and slot 1416, and between second lateral portion 1444 and slot 1416. Thus, rotation of drive assembly 1410 in the general direction of arrow "CDA" causes distal translation of carriage 1440 and needle 1406 in the general direction of arrow "CDB."

Figure 64:
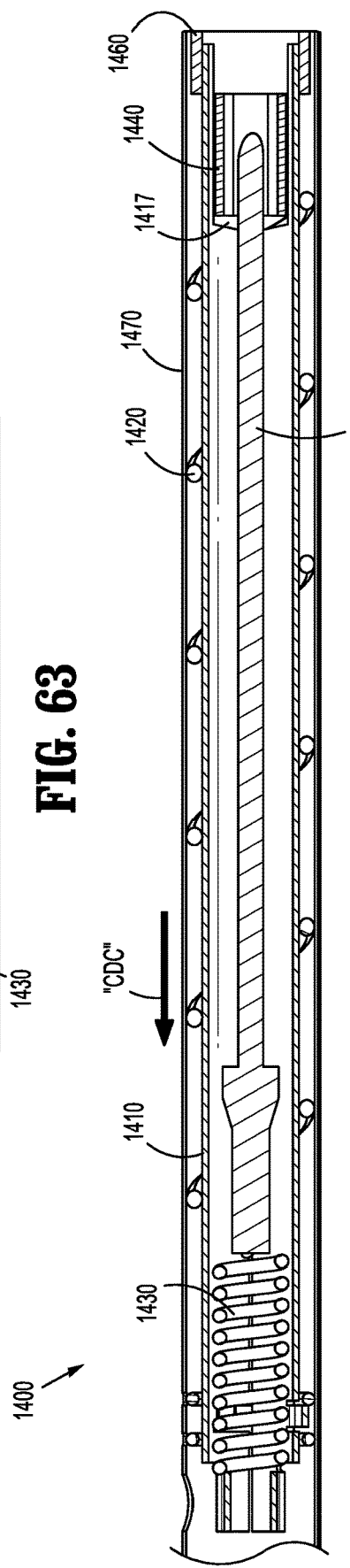
FIG. 64 is a cross-sectional view of the end effector of FIGS. 57-63 illustrating the needle in a retracted position.

Continued rotation of drive assembly 1410 in the general direction of arrow "CDA" causes continued distal advancement of needle 1406 until distal tip 1406b of needle 1406 extends a sufficient distance distally beyond a distal end of outer tube 1470. With particular reference to FIG. 64, after a predetermined amount of rotation of drive assembly 1410 and distal travel of needle 1406 (e.g., corresponding to when distal tip 1406b is sufficiently advanced within tissue), notch 1443 of carriage 1440 is advanced distally beyond helix or coil assembly 1420, and portions of carriage 1440 are distally advanced into a widened portion 1417 (see FIGS. 57 and 59) of slot 1416 of drive assembly 1410. In this position, carriage 1440 is configured to spring from an approximated position, where first leg 1444a and second leg 1444b are relatively close to each other, toward an open position where first leg 1444a and second leg 1444b of second lateral portion 1444 are farther apart from each other. It is envisioned that carriage 1440 is spring biased into the open position, cammed into the open position, or otherwise moved toward the open position.

In the approximated position, a distance 1444d (FIG. 61) between outer edges of first leg 1444a and second leg 1444b is smaller than a width 1416d (FIG. 61) of slot 1416. In the open portion, distance 1444d is greater than width 1416d of slot 1416. Accordingly, in the open position, carriage 1440 is prevented from moving proximally with respect to outer tube 1470. Additionally, distal stop 1460 prevents carriage 1440 from moving distally beyond outer tube 1470, as first lateral portion 1442 and second lateral portion 1444 would contact distal stop 1460.

Thus, since the proximal force exerted by retraction spring 1430 is no longer opposed by the engagement between carriage 1440 and helix or coil assembly 1420, needle 1406 is able to move proximally in the general direction of arrow "CDC" until it reaches the approximate position shown in FIG. 64. However, since carriage 1440 is in its open position, engagement between a proximal wall 1417a (FIG. 59) of widened portion 1417 of slot 1416, and first lateral portion 1442 and second lateral portion 1444 of carriage 1440 resists the proximal force exerted by retraction spring 1430, which causes carriage 1440 to remain in the approximate position shown in FIG. 64. Accordingly, at least a portion of needle 1406 is retracted through aperture 1446 of carriage 1440 after notch 1443 of carriage 1440 extends beyond helix or coil assembly 1420.

Offset Needle

Referring now to FIGS. 65-70, an embodiment of an end effector 1500 including a longitudinally offset needle 1506 is shown. End effector 1500 is configured for use in connection with surgical device 100. Generally, end effector 1500 is configured to advance needle 1506 towards tissue. While FIGS. 65-70 illustrate a particular type of needle 1506, end effector 1500 may be used with different types of needles.

Figure 66:
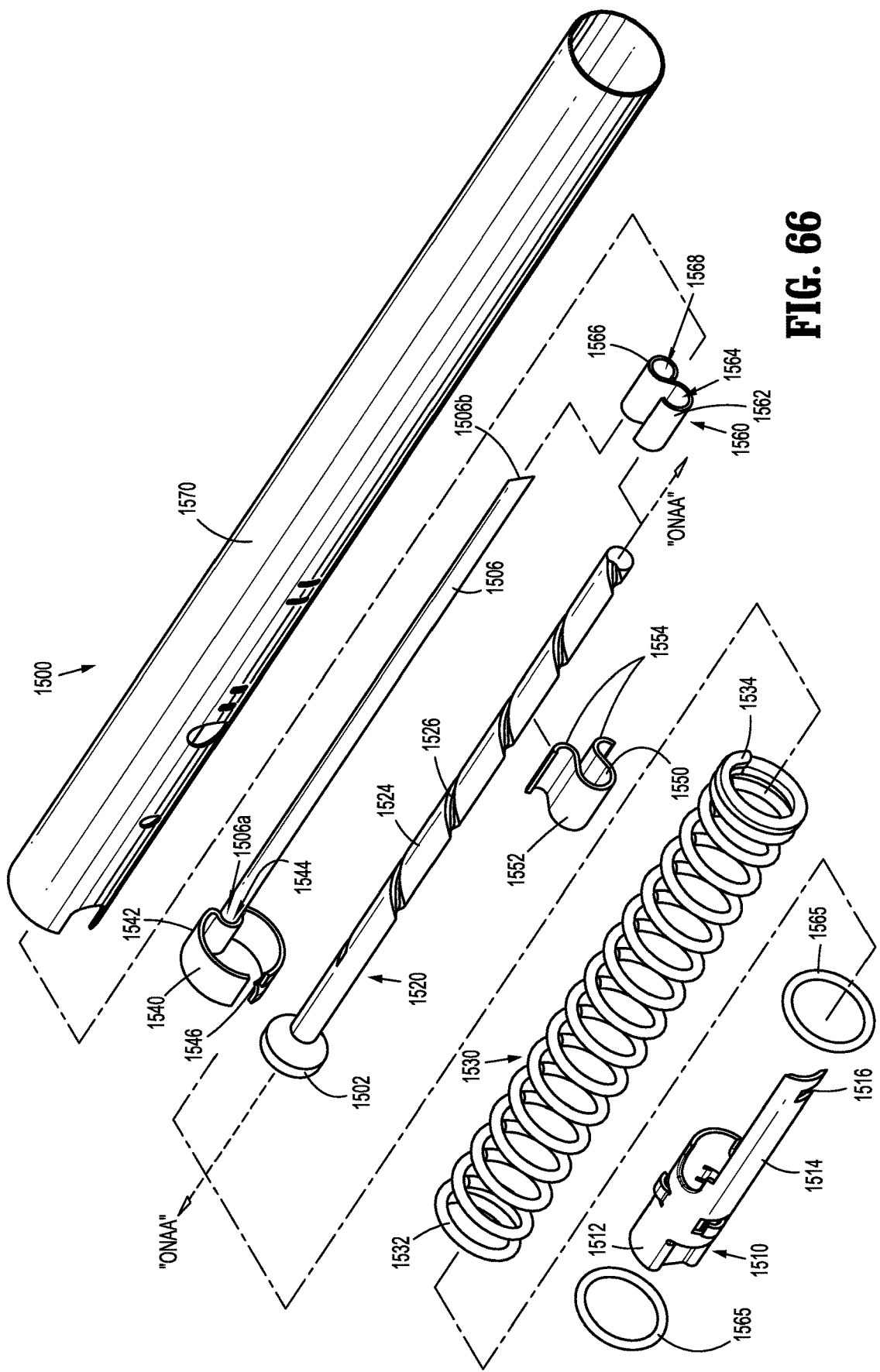
FIG. 66 is an assembly view of the end effector of FIG. 65.

With particular reference to FIG. 66, end effector 1500 includes a drive assembly 1510, a drive shaft 1520, a biasing element 1530, a needle ring 1540, a reverse drive unit 1550, a guide bracket 1560, a pair of rings 1565, and an outer tube 1570.

Drive assembly 1510 of end effector 1500 is mechanically engaged (e.g., operatively coupled, directly affixed, etc.) to drive rod 150 of surgical device 100 of the present disclosure. Drive assembly 1510 includes a proximal portion 1512 and an arm 1514 extending distally from proximal portion 1512. Arm 1514 of drive assembly 1510 includes a notch 1516 disposed on a distal portion thereof. As discussed below, notch 1516 is configured to engage a portion of needle ring 1540.

Drive shaft 1520 of end effector 1500 includes a proximal portion 1522 and an elongated portion 1524 extending distally from proximal portion 1522. Proximal portion 1522 of drive shaft 1520 is configured to engage (e.g., non-rotationally engage) drive assembly 1510, such that rotation of drive assembly 1510 results in a corresponding rotation of drive shaft 1520. Elongated portion 1524 of drive shaft 1520 defines a longitudinal axis "ONAA" disposed at a radial center of end effector 1500. Elongated portion 1524 also includes a helical groove 1526 therein, which is configured to engage reverse drive unit 1550, as discussed below.

Needle 1506 is disposed radially outward of elongated portion 1524 of drive shaft 1520, and is thus laterally offset from longitudinal axis "ONAA." A proximal portion 1506*a* of needle 1506 engages (e.g., frictionally engages) a portion of needle ring 1540, as discussed below. A distal tip 1506*b* of needle 1506 is configured to pierce tissue.

Biasing element 1530, e.g., a compression spring, of end effector 1500 includes a proximal portion 1532 and a distal portion 1534. Proximal portion 1532 of biasing element 1530 is positioned radially outward of and in mechanical cooperation (e.g., affixed to) drive assembly 1510 (e.g., proximal portion 1512 of drive assembly 1510). Distal portion 1534 of biasing element 1530 is disposed proximally of at least a portion of needle ring 1540, and is configured to urge needle ring 1540, and thus needle 1506, distally with respect to outer tube 1570.

Needle ring 1540 of end effector 1500 includes an engagement portion 1542 defining a channel 1544, and includes a finger 1546 positioned generally opposite engagement portion 1542. Channel 1544 of engagement portion 1542 of needle ring 1540 is configured to engage proximal portion 1506*a* of needle 1506, such that needle 1506 is longitudinally fixed with respect to needle ring 1540, for instance. Finger 1546 extends radially inward and is configured for selective engagement by notch 1516 of arm 1514 of drive assembly 1510.

Reverse drive unit 1550 of end effector 1500 includes an arcuate body portion 1552 and a pair of legs 1554 extending generally laterally therefrom. Body portion 1552 of reverse drive unit 1550 is configured to engage elongated portion 1524 of drive shaft 1520. Legs 1554 of reverse drive unit 1550 are configured to engage or contact an inner wall of outer tube 1570 to help maintain the lateral position of reverse drive unit 1550 with respect to outer tube 1570. Additionally, reverse drive unit 1550 includes a pin (not explicitly shown) extending generally laterally from body portion 1552. The pin is configured to slidingly engage helical groove 1526 of elongated portion 1524 of drive shaft 1520, such that rotation of drive shaft 1520 results in longitudinal movement of reverse drive unit 1550.

Guide bracket 1560 of end effector 1500 is generally shaped similar to a FIG. 8 and/or letter S, and includes a first engagement portion 1562 defining a first aperture 1564, and a second engagement portion 1566 defining a second aperture 1568. Guide bracket 1560 is positioned distally of reverse drive unit 1550 and helps maintain the desired lateral spacing between drive shaft 1520 and needle 1506. First aperture 1564 of first engagement portion 1562 is configured to engage a distal portion of drive shaft 1520. Drive shaft 1520 is rotatable with respect to guide bracket 1560, such that rotation of drive shaft 1520 does not effect the rotational position of guide bracket 1560. Second aperture 1568 of second engagement portion 1566 is configured to slidingly receive at least a portion of needle 1506 therethrough, such that needle 1506 is longitudinally translatable with respect to guide bracket 1560.

Rings 1565 (e.g., O-rings) of end effector 1500 are positioned radially outward of proximal portion 1512 of drive assembly 1510. Rings 1565 help maintain appropriate spacing between drive assembly 1510 and outer tube 1570, and help facilitate rotation of drive assembly 1510 with respect to outer tube 1570.

Outer tube 1570 of end effector 1500 is configured for positioning radially outward of at least portions of needle 1506, drive assembly 1510, drive shaft 1520, biasing element 1530, needle ring 1540, reverse drive unit 1550, guide bracket 1560, and rings 1565.

Figure 65:
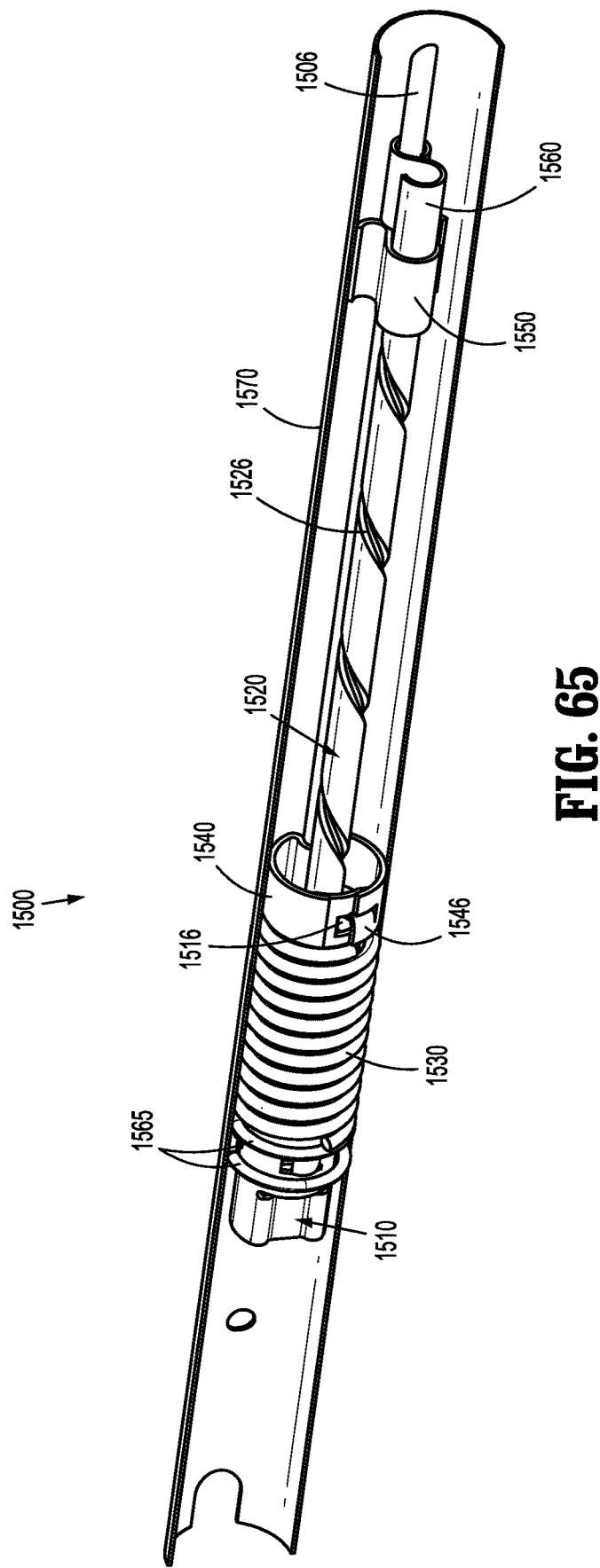
FIG. 65 is a perspective view of portions of an end effector in accordance with embodiments of the present disclosure.

As shown in FIGS. 65 and 67, prior to use, notch 1516 of drive assembly 1510 is in contact with finger 1546 of needle ring 1540. This contact between notch 1516 and finger 1546 resists the distal bias of biasing element 1530, and thus prevents needle 1506 from distally translating with respect to outer tube 1570.

In use, in response to at least a partial actuation of the trigger of surgical device 100, drive rod 150 rotates, as discussed above. With reference to FIGS. 67-69, rotation of the drive rod 150 results in a corresponding rotation of drive assembly 1510 with respect to outer tube 1570. A predetermined amount of rotation (e.g., about 10°) of drive assembly 1510 causes notch 1516 of drive assembly 1510 to rotate in the general direction of arrow "ONA" (FIG. 67) from a first position where notch 1516 (or walls defining notch 1516) is in contact with finger 1546 of needle ring 1540, to a second position where notch 1516 (or walls defining notch 1516) is free from contact with finger 1546. The disengagement between notch 1516 and finger 1546 results in finger 1546 no longer resisting the distal bias of biasing element 1530, thus resulting in needle 1506 distally translating with respect to outer tube 1570 in the general direction of arrow "ONB" in FIG. 67 to the position shown in FIG. 69 where needle ring 1540 contacts reverse drive unit 1550. Thus, to insert needle 1506 into tissue, a distal end of end effector 1500 is positioned adjacent or in contact with tissue, and the trigger of surgical device 100 is at least partially actuated, thus distally advancing a portion of needle 1506 into tissue.

As described above, rotation of drive assembly 1510 of end effector 1500 results in a corresponding rotation of drive shaft 1520. Additionally, due to the engagement between reverse drive unit 1550 and helical groove 1526 of drive shaft 1520, rotation of drive shaft 1520 in the general direction of arrow "ONA" results in reverse drive unit 1550 moving proximally in the general direction of arrow "ONC" (FIGS. 69 and 70) with respect to drive shaft 1520. This proximal movement of reverse drive unit 1550 causes a corresponding proximal movement of needle ring 1540 and needle 1506 due to the engagement between reverse drive unit 1550 and needle ring 1540.

Continued or additional actuation of the trigger of surgical device 100 results in reverse drive unit 1550 reaching its proximal-most position, as shown in FIG. 70, where needle 1506 is positioned such that distal tip 1506*b* thereof is longitudinally aligned with or proximal of a distal end of outer tube 1570, thereby reducing the possibility of a user unintentionally contacting needle 1506.

Further, the rotation of drive assembly 1510 (e.g., in response to continued actuation or an additional actuation of trigger) results in notch 1516 of arm 1514 re-engaging finger 1546 of needle ring 1540. Here, a second distal advancement of needle 1506 with respect to outer tube 1570 is prevented due to the engagement between needle ring 1540 and reverse drive unit 1550 (FIG. 70). Moreover, the engagement between reverse drive unit 1550 and helical groove 1526 prevents distal movement of reverse drive unit 1550 with respect to drive shaft 1520.

Spring Return "A"

Referring now to FIGS. 71-76, an embodiment of an end effector 1700 is shown. End effector 1700 is configured for use in connection with surgical device 100. Generally, end effector 1700 is configured to advance a needle 1706 towards tissue and to eject a barbed suture 1702 towards tissue. While FIGS. 71-76 illustrate a particular type of barbed suture 1702 and a particular type of needle 1706, end effector 1700 may be used with different types of sutures and/or needles.

Figure 72:
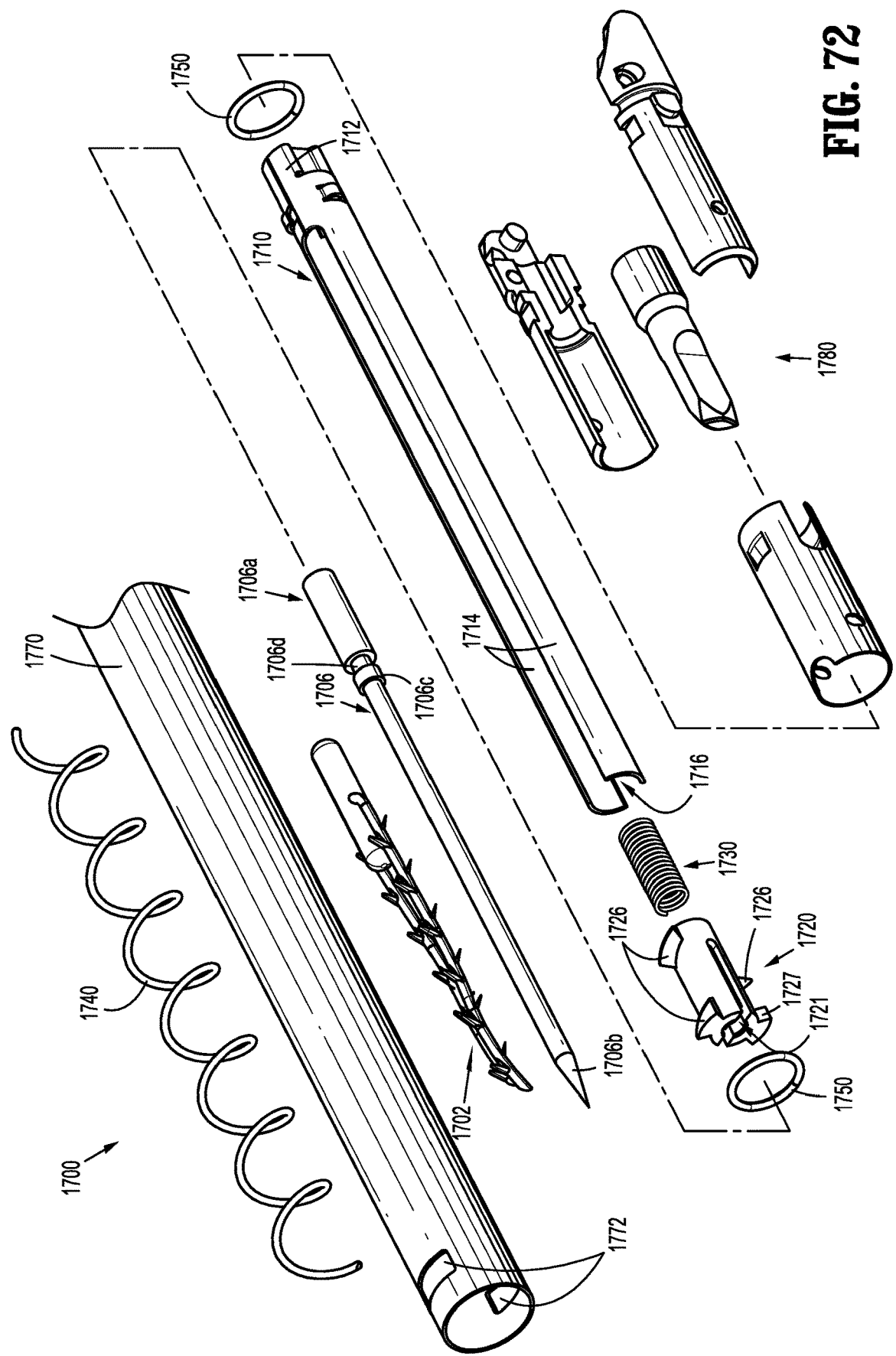
FIG. 72 is an assembly view of the end effector of FIG. 71.

With particular reference to FIG. 72, end effector 1700 includes a drive assembly 1710, a driver 1720, a retraction spring 1730, a helix or coil assembly 1740, a pair of rings 1750, and an outer tube 1770.

Drive assembly 1710 of end effector 1700 is mechanically engaged (e.g., operatively coupled, directly affixed, etc.) to a drive rod assembly 1780 of the handle assembly of the surgical device 100 of the present disclosure. Rotation of drive rod assembly 1780 in the general direction of arrow "SRA" in FIG. 73 results in a corresponding rotation of drive assembly 1710. Drive assembly 1710 includes a proximal hub 1712 and a pair of arms 1714 extending therefrom. Arms 1714 of drive assembly 1710 define a pair of slots 1716 therebetween. Slots 1716 are configured to slidingly receive portions of driver 1720.

Needle 1706 includes a proximal hub 1706a, and a distal tip 1706b configured to pierce tissue. Needle 1706 also includes a lip 1706c disposed distally of proximal hub 1706a. Lip 1706c is configured to engage a portion of driver 1720, as discussed below.

Retraction spring 1730 of end effector 1700 is engaged with (e.g., affixed to) a proximal end of needle 1706 and a portion of drive assembly 1710. Retraction spring 1730 is configured to bias needle 1706 proximally.

Figure 71:
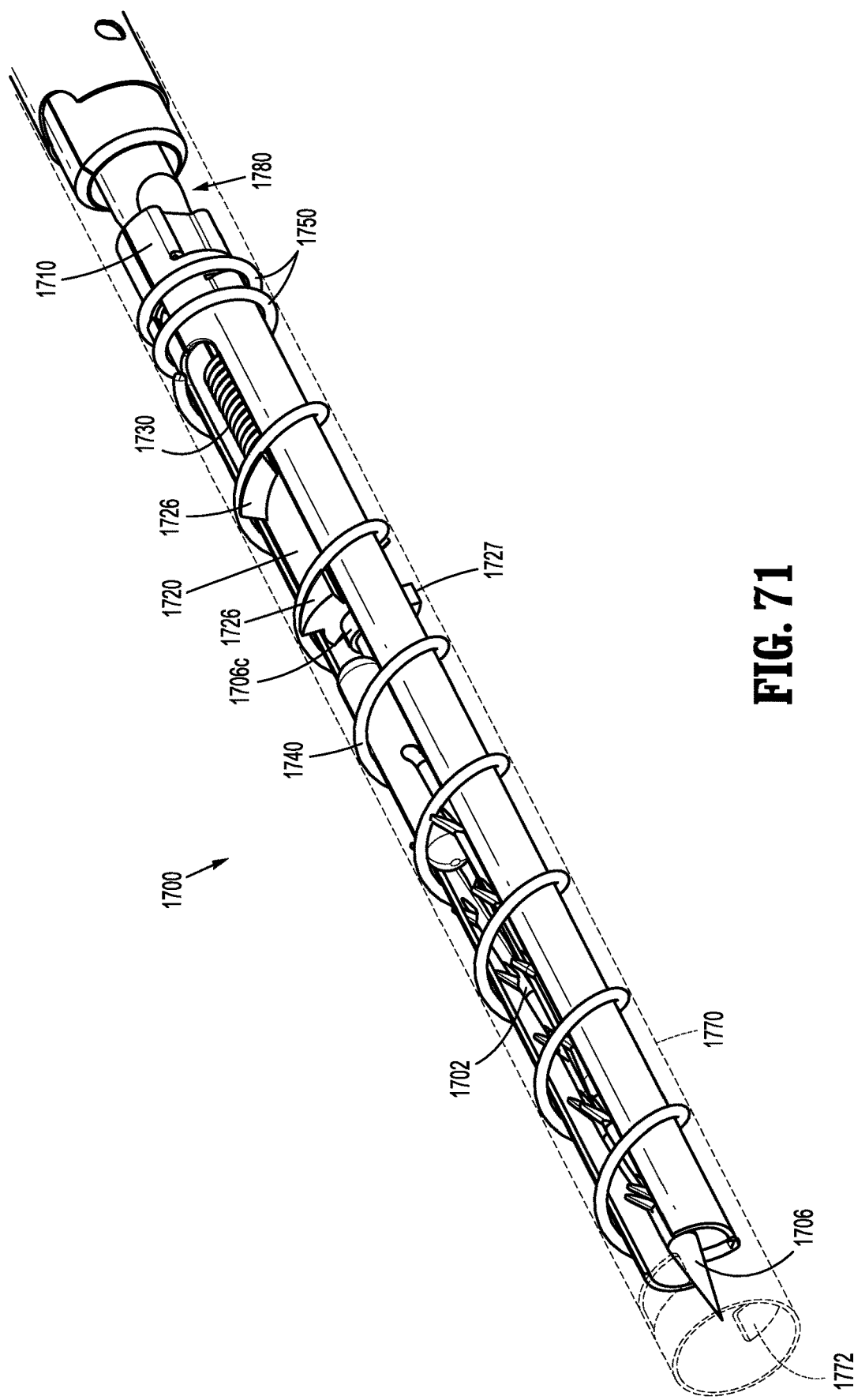
FIG. 71 is a perspective view of an end effector in accordance with embodiments of the present disclosure.

With particular reference to FIGS. 71 and 73, rings 1750 (e.g., O-rings) of end effector 1700 are positioned radially outward of a proximal portion drive assembly 1710. Rings 1750 help maintain appropriate spacing between drive assembly 1710 and outer tube 1770, and help facilitate rotation of drive assembly 1710 with respect to outer tube 1770.

Helix or coil assembly 1740 of end effector 1700 extends between a proximal portion of drive assembly 1410 and a distal portion of outer tube 1770, and is disposed radially within outer tube 1770. Helix or coil assembly 1740 is stationary with respect to outer tube 1770, and is configured to engage a portion of driver 1720 such that driver 1720 can move longitudinally and rotationally within outer tube 1770 and with respect to outer tube 1770.

With particular reference to FIG. 74, driver 1720 of end effector 1700 includes a proximal portion 1722 and a pair of arms 1724 extending distally from proximal portion 1722. Arms 1724, including a first arm 1724a and a second arm 1724b, are biased radially outwardly in the general direction of arrow "SRB" in FIG. 75. Engagement between arms 1724 and outer tube 1770 prevent arms 1724 from moving radially out of engagement with needle 1706. Driver 1720 defines a cavity 1721 (FIG. 72) therein, which is configured to releasably retain proximal hub 1706a of needle 1706 therein. Driver 1720 further includes a plurality of threads 1726 extending radially outward from proximal portion 1722 and/or at least one arm 1724. Threads 1726 are configured to engage helix or coil assembly 1740 (e.g., distal edges of helix or coil assembly 1740). In the illustrated embodiment, driver 1720 includes a first thread 1726a extending radially outward from proximal portion 1722, a second thread 1726b extending radially outward from first arm 1724a, and a third thread 1726c extending radially outward from a distal portion of second arm 1724b. Proximal portions of threads 1726 are generally arcuate for engaging with helix or coil assembly 1740. A distal face 1726ca of third thread 1726c is generally perpendicular to needle 1706.

Driver 1720 also includes a finger 1727 extending radially outward from the arm that does not include a thread at its distal portion. In the illustrated embodiment, first arm 1724a of arms 1724 of end effector 1700 includes finger 1727. A distal face 1727a of finger 1727 is generally perpendicular to needle 1706 and generally parallel to distal face 1726ca of third thread 1726c. As shown in FIG. 74, distal face 1726ca of third thread 1726c and distal face 1727a of finger 1727 are each configured to mechanically engage a proximal surface of lip 1706c of needle 1706.

With particular reference to FIG. 73, driver 1720 of end effector 1700 further includes tabs 1728 disposed adjacent a distal end of each arm 1724. Tabs 1728 extend radially inward from the respective arm 1724, and are each configured to engage a recess 1706d of needle 1706. Recesses 1706d of needle 1706 are disposed between proximal hub 1706a and lip 1706c of needle 1706. Driver 1720 is rotatable with respect to needle 1706.

Outer tube 1770 of end effector 1700 is configured for positioning radially outward of at least portions of needle 1706, drive assembly 1710, driver 1720, retraction spring 1730, and helix or coil assembly 1740. Outer tube 1770 includes a pair of apertures 1772 disposed adjacent its distal end. Each aperture 1772 is configured to engage (e.g., releasably engage) one of third thread 1726c or finger 1727 of driver 1720.

In use, in response to at least a partial actuation of the trigger of surgical device 100, drive rod assembly 1780 rotates, as discussed above. With reference to FIGS. 73-76, initial rotation of the drive rod assembly 1780 results in a corresponding rotation of drive assembly 1710 and driver 1720 of end effector 1700 with respect to outer tube 1770 in the general direction of arrow "SRA" in FIG. 73. Due to the engagement between helix or coil assembly 1740 and fingers 1726 of driver 1720, rotation of driver 1720 in the general direction of arrow "SRA" results in a corresponding rotation and distal translation of driver 1720 with respect to outer tube 1770 in the general direction of arrow "SRC" in FIG. 73. Distal translation of driver 1720 causes a corresponding distal translation of needle 1706. Additionally, since driver 1720 is rotatable with respect to needle 1706, rotation of driver 1720 does not cause rotation of needle 1706.

Continued rotation of drive assembly 1710 in the general direction of arrow "SRA" causes continued distal advancement of driver 1720 and needle 1706 until distal tip 1706b of needle 1706 extends a sufficient distance distally beyond a distal end of outer tube 1770. Thus, to insert needle 1706 and/or barbed suture 1702 into tissue, a distal end of end effector 1700 is positioned adjacent or in contact with tissue, and the trigger of surgical device 100 is at least partially actuated, thus distally advancing a portion of needle 1706 and/or barbed suture 1702 into tissue.

Figure 75:
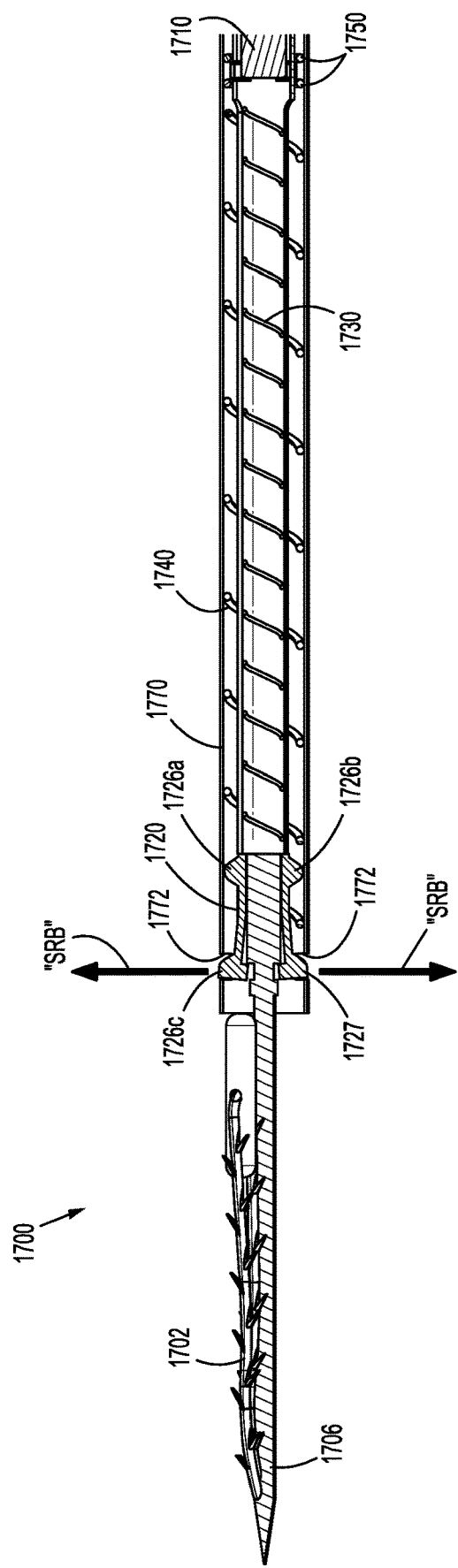
FIG. 75 is a cross-sectional view of the end effector of FIGS. 71-74 illustrating a needle in an advanced position.
Figure 76:
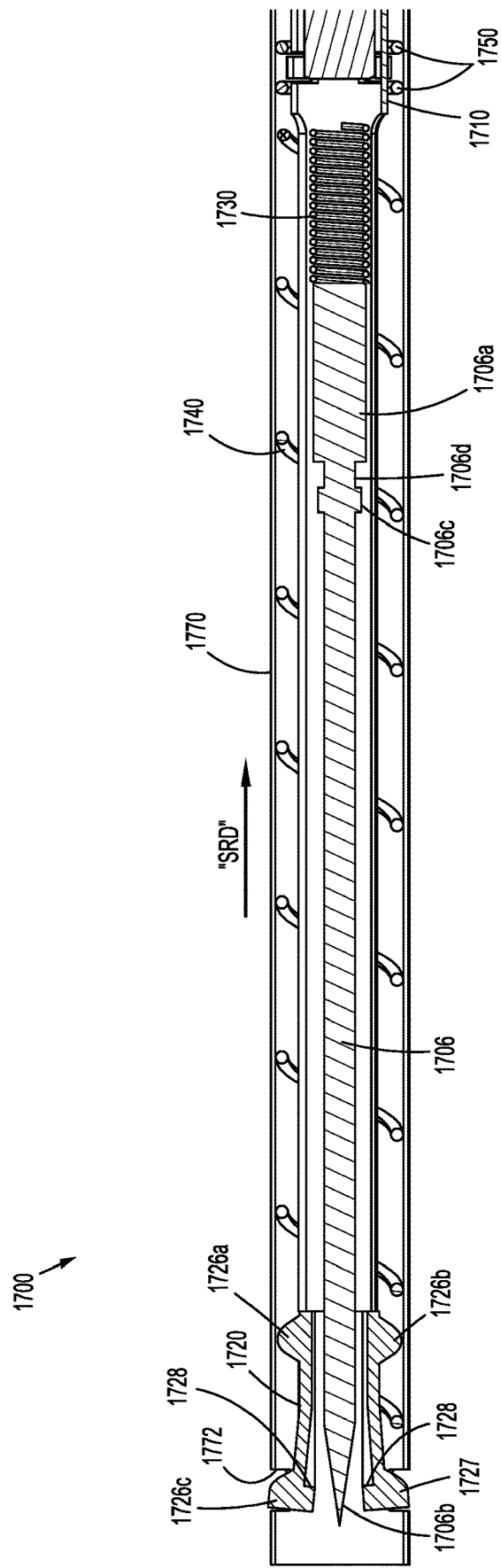
FIG. 76 is a cross-sectional view of the end effector of FIGS. 71-75 illustrating the needle in a retracted position.

With particular reference to FIGS. 75 and 76, after a predetermined amount of rotation of drive assembly 1710 of end effector 1700 and distal travel of needle 1706 (e.g., corresponding to when distal tip 1706b is sufficiently advanced within tissue), fingers 1726 of driver 1720 are advanced distally beyond helix or coil assembly 1710. In this position, third thread 1726c and finger 1727 of driver 1720 are axially aligned with apertures 1772 of outer tube 1770. Here, outer tube 1770 no longer resists the radially outward bias of arms 1724 of driver 1720, thus permitting arms 1724 to flex radially outward in the direction of "SRB" in FIG. 75 such that third thread 1726c and finger 1727 engage apertures 1772, which causes driver 1720 to stop moving distally with respect to outer tube 1770.

Further, the radially outward movement of arms 1724 causes tabs 1728 of driver 1720 of end effector 1700 to disengage recess 1706*d* of needle 1706. Thus, since the proximal force exerted by retraction spring 1730 of end effector 1700 is no longer opposed by the engagement between driver 1720 and needle 1706, needle 1706 is able to move proximally in the general direction of arrow "SRD" until needle 1706 reaches the approximate position shown in FIG. 76. Since driver 1720 is engaged with apertures 1772 of outer tube 1770 and is no longer mechanically engaged with needle 1706, the proximal movement of needle 1706 causes at least a portion of needle 1706 to move through cavity 1721 of driver 1720, while driver 1720 remains adjacent a distal portion of outer tube 1770, as shown in FIG. 76.

It is envisioned that end effector 1700 can be used more than once. After its initial use, as described above, a user can manually pull needle 1706 distally (e.g., using a pliers-like tool) until recess 1706*d* of needle 1706 is axially aligned with tabs 1728 of driver 1720. In this position, while needle 1706 is being maintained in its longitudinal position, a user can manually move arms 1724 of driver 1720 radially inwardly by exerting an appropriate force (e.g., through apertures 1772) on third thread 1726*c* and finger 1727 to cause tabs 1728 to engage recess 1706*d*. Here, the proximal force exerted by retraction spring 1730 causes both needle 1706 and driver 1720 to move proximally to their initial positions such that end effector 1700 can be used again to advance needle 1706. Additionally, if a user wishes to use another barbed suture 1702, needle 1706 can be pulled farther proximally to allow an additional barbed suture 1702 to engage needle 1706 prior to driver 1720 re-engaging needle 1706.

Lead Screw Spring Clip

Referring now to FIGS. 77-82, an embodiment of an end effector 2000 including a pre-loaded spring assembly is shown. End effector 2000 is configured for use in connection with surgical device 100. Generally, end effector 2000 is configured to advance a needle 2006 towards tissue. While FIGS. 77-82 illustrate a particular type of needle 2006, end effector 2000 may be used with different types of needles.

Figure 78:
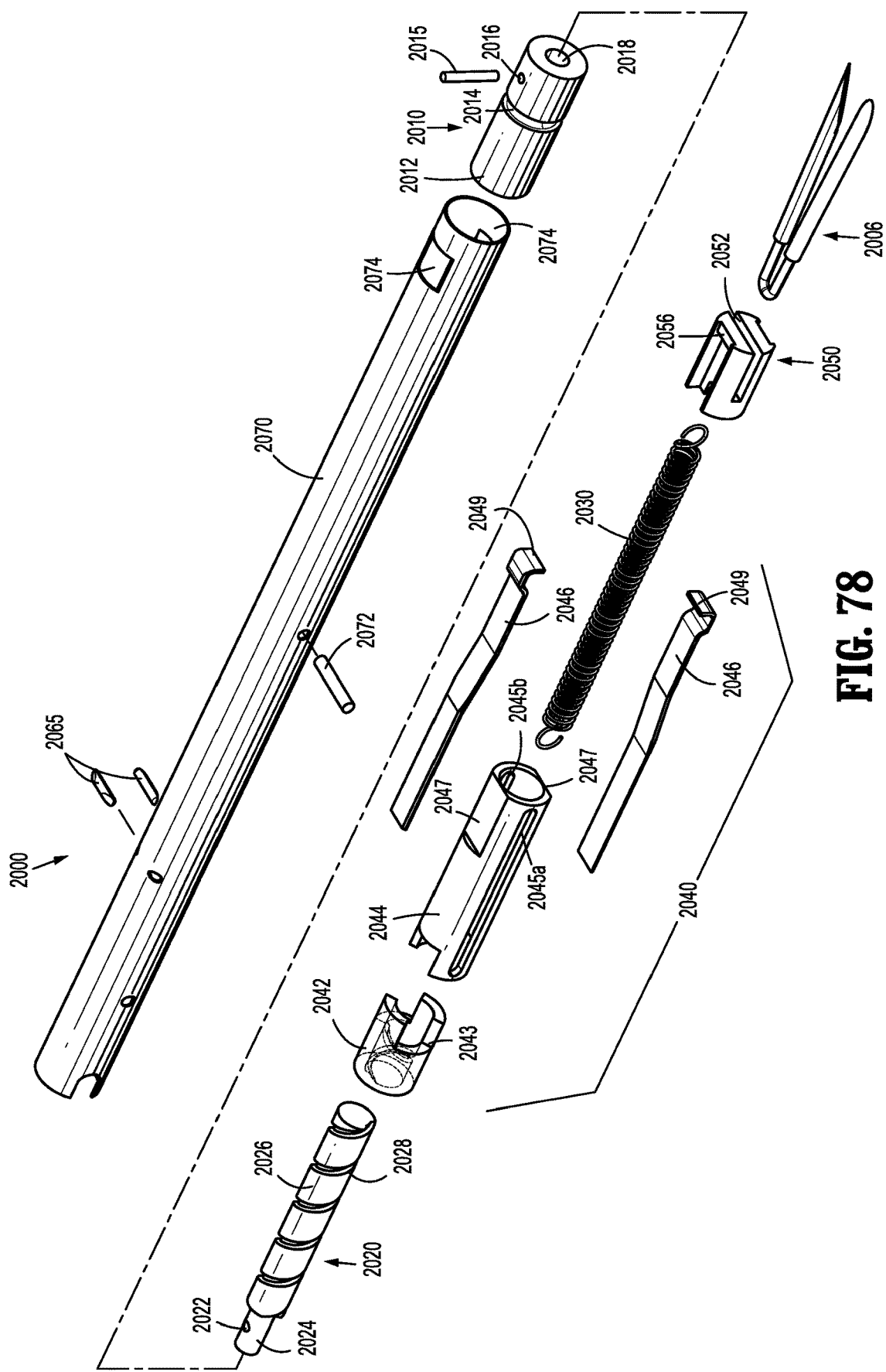
FIG. 78 is an assembly view of the end effector of FIG. 77.
Figure 79:
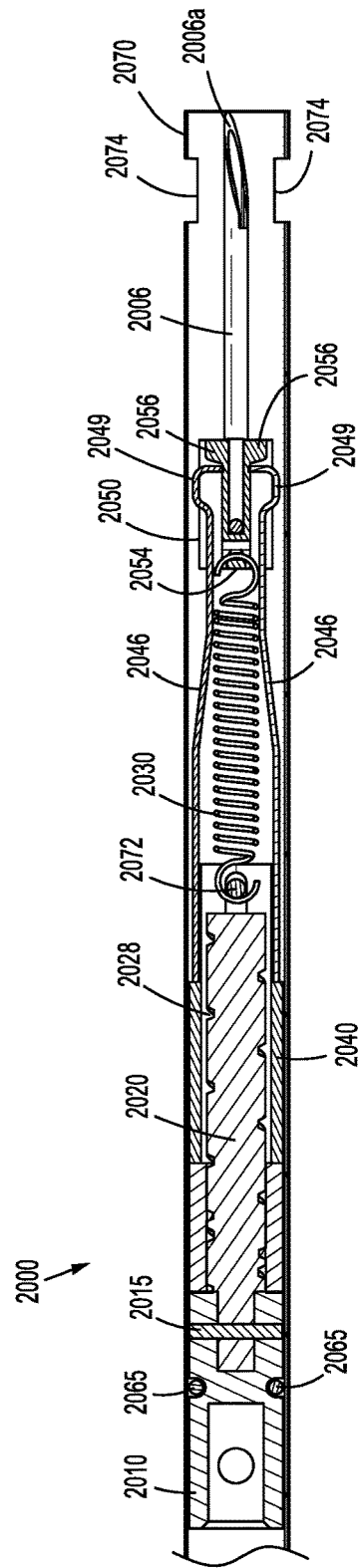
FIG. 79 is a cross-sectional view of the end effector of FIGS. 77-78.
Figure 80:
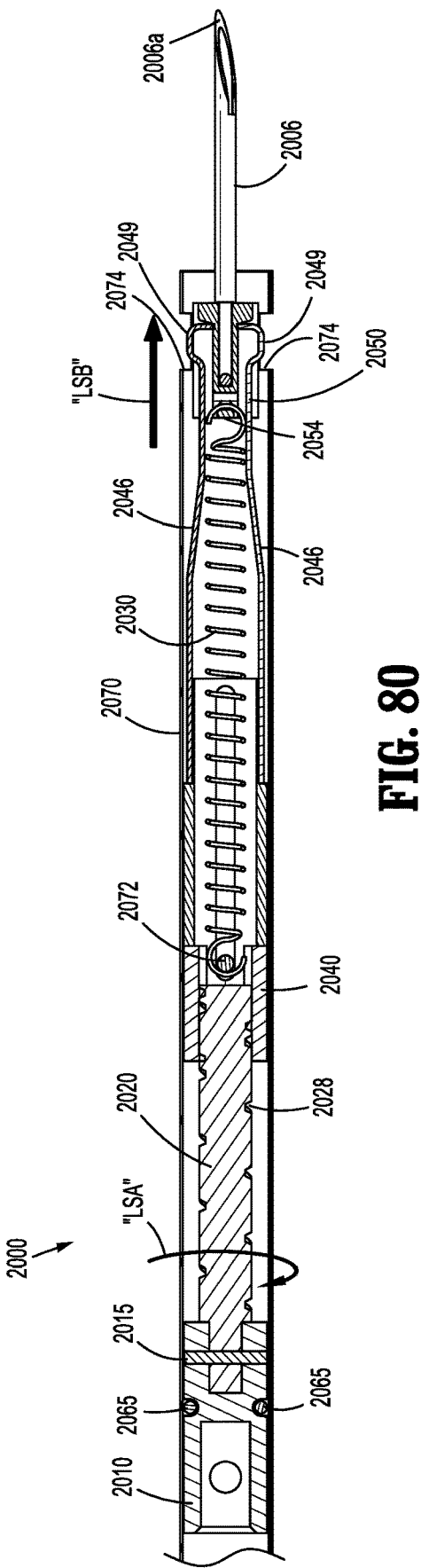
FIGS. 80 and 81 are cross-sectional views of the end effector of FIGS. 77-79 illustrating a needle in an advanced position.

With particular reference to FIG. 78, end effector 2000 includes a drive assembly 2010, a driver 2020, a biasing element or retraction spring 2030, a clip assembly 2040, a needle assembly 2050, pins 2065, and an outer tube 2070.

Drive assembly 2010 of end effector 2000 is mechanically engaged (e.g., operatively coupled, directly affixed, etc.) to drive rod 150 of surgical device 100 of the present disclosure. Rotation of the drive rod assembly in the general direction of arrow "LSA" in FIG. 80 results in a corresponding rotation of drive assembly 2010. Drive assembly 2010 includes a proximal hub 2012, a groove 2014 and a lateral aperture 2016, and defines a cavity 2018 extending at least partially therethrough. Groove 2014 is configured to engage pins 2065, which facilitates the rotation of drive assembly 2010 with respect to outer tube 2070, and which prevents or limits longitudinal translation therebetween. Lateral aperture 2016 of drive assembly 2010 is configured to receive a portion of a pin 2015; pin 2015 also extends at least partially through an aperture 2022 of driver 2020, as discussed below. Cavity 2018 of drive assembly 2010 is configured to receive a proximal portion 2024 of driver 2020, as discussed below.

Driver 2020 of end effector 2000 includes an aperture 2022, a proximal portion 2024, and a body portion 2026 including a helical groove 2028. Proximal portion 2024 of driver 2020 has a smaller diameter than body portion 2026 and is configured to slidingly engage cavity 2018 of drive assembly 2010. When proximal portion 2024 is engaged with cavity 2018, and when aperture 2022 of driver 2020 is rotationally aligned with lateral aperture 2016 of drive assembly 2010, pin 2015 is insertable through lateral aperture 2016 and aperture 2022 to prevent or limit rotational movement and longitudinal movement between drive assembly 2010 and driver 2020.

Figure 77:
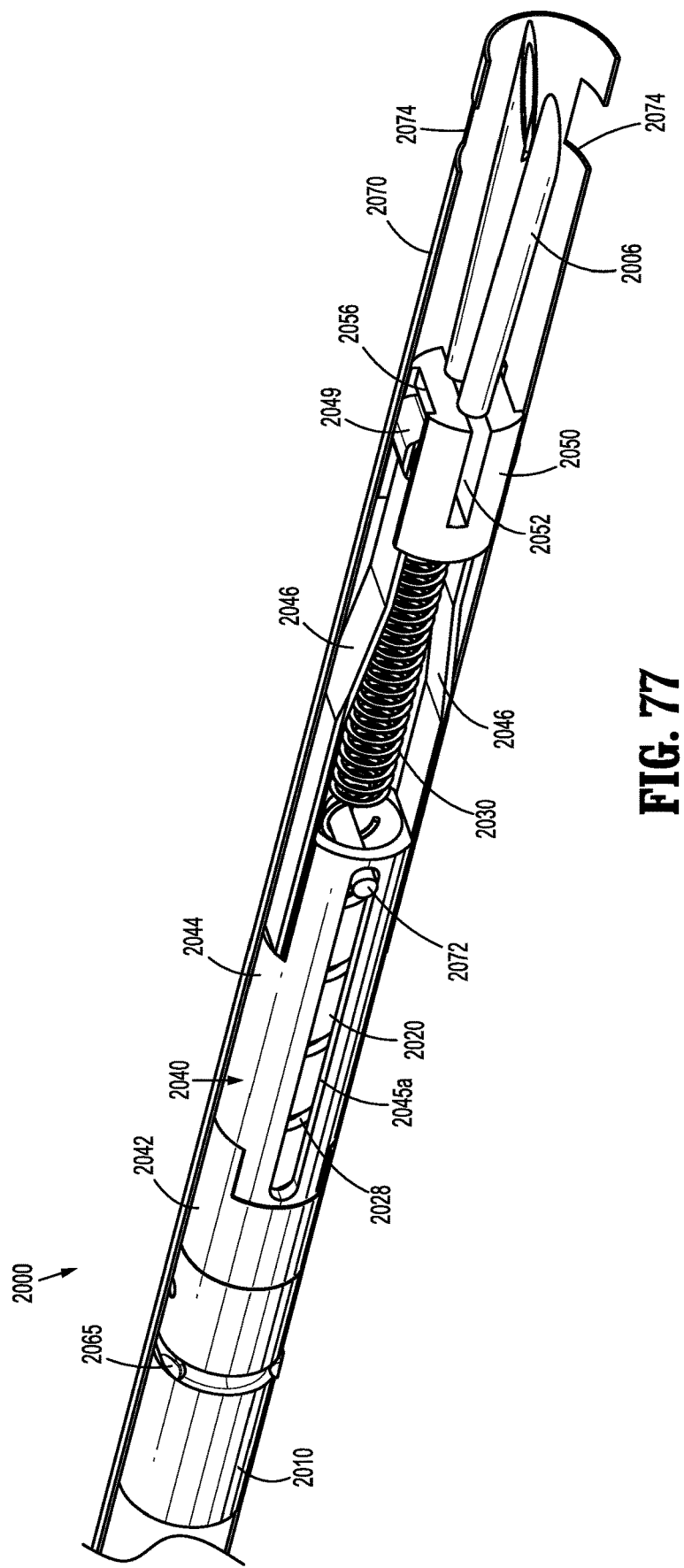
FIG. 77 is a perspective view of portions of an end effector in accordance with embodiments of the present disclosure.

Retraction spring 2030 of end effector 2000 is engaged with (e.g., hooked on) a proximal end of needle assembly 2050 and a pin 2072 extending through outer tube 2070 and through a portion of clip assembly 2040 (see FIG. 77). Retraction spring 2030 is configured to bias needle assembly 2050 proximally.

Clip assembly 2040 of end effector 2000 includes a proximal portion 2042, a body portion 2044, and a pair of arms 2046 extending distally from body portion 2044. Proximal portion 2042 of clip assembly 2040 is configured to engage driver 2020. In particular, proximal portion 2042 of clip assembly 2040 is positionable radially outward of driver 2020 and includes an engagement structure 2043 configured to engage helical groove 2028 of driver 2020. While engagement structure 2043 is illustrated as a helical thread, engagement structure 2043 may also be a pin or the like. Due to the engagement between proximal portion 2042 and helical groove 2028 of driver 2020, rotation of driver 2020 results in longitudinal translation of proximal portion 2042.

Body portion 2044 of clip assembly 2040 is mechanically engaged with proximal portion 2042, and includes a pair of longitudinal slots 2045*a*, 2045*b* extending therethrough. Slots 2045*a*, 2045*b* are configured to slidingly receive pin 2072, such that pin 2072 helps guide longitudinal translation of body portion 2042 with respect to pin 2072 and outer tube 2070. Body portion 2044 also includes recessed or flattened portions 2047 for engaging a proximal portion of each arm 2046. It is envisioned that proximal portions of arms 2046 are rigidly affixed to flattened portions 2047 of body portion 2044.

Arms 2046 of clip assembly 2040 extend distally from body portion 2044. Each arm 2046 includes a finger 2049 adjacent a distal portion thereof. Fingers 2049 are configured to releasably engage a portion of needle assembly 2050, as discussed below. At least portions of arms 2046 (e.g., fingers 2049) are biased radially outwardly in the general direction of arrow "LSC" in FIG. 81 into contact with outer tube 2070, for example. Engagement between fingers 2049 and outer tube 2070 prevent fingers 2049 from moving radially out of engagement with needle assembly 2050.

Needle assembly 2050 is configured to hold or releasably hold needle 2006 or a portion of needle 2006. In embodiments, needle assembly 2050 includes a distal recess 2052 for engaging needle 2006. Additionally, needle assembly 2050 includes a proximal portion 2054 configured to engage a distal portion of retraction spring 2030. Needle assembly 2050 also includes a pair of distal lips 2056, which are each configured to engage a respective finger 2049 of arms 2046 of clip assembly 2040. The engagement between fingers 2049 and distal lips 2056 resists the proximal force exerted on needle assembly 2050 by retraction spring 2030.

Outer tube 2070 of end effector 2000 is configured for positioning radially outward of at least portions of needle 2006, drive assembly 2010, driver 2020, retraction spring 2030, clip assembly 2040, and needle assembly 2050. Outer tube 2070 includes a pair of apertures 2074 disposed adjacent its distal end. Each aperture 2074 is configured to engage (e.g., releasably engage) portions of fingers 2049 of arms 2046 of clip assembly 2040 (see FIGS. 81 and 82).

In use, in response to at least a partial actuation of the trigger of surgical device 100, drive rod 150 rotates, as discussed above. With reference to FIGS. 79-82, initial rotation of the drive rod 150 results in a corresponding rotation of drive assembly 2010 and driver 2020 with respect to outer tube 2070 in the general direction of arrow "LSA" in FIG. 80. Due to the engagement between helical groove 2028 of driver 2020 and engagement structure 2043 of clip assembly 2040, rotation of driver 2020 in the general direction of arrow "LSA" results in distal translation of clip assembly 2040 with respect to outer tube 2070 in the general direction of arrow "LSB" in FIG. 80. Distal translation of clip assembly 2040 causes a corresponding distal translation of needle assembly 2050 and needle 2006.

Continued rotation of drive assembly 2010 in the general direction of arrow "LSA" causes continued distal advancement of driver clip assembly 2040, needle assembly 2050, and needle 2006 until a distal tip 2006a of needle 2006 extends a sufficient distance distally beyond a distal end of outer tube 2070. Thus, to insert needle 2006 into tissue, a distal end of end effector 2000 is positioned adjacent or in contact with tissue, and the trigger of surgical device 100 is at least partially actuated, thus distally advancing a portion of needle 2006 into tissue.

Figure 81:
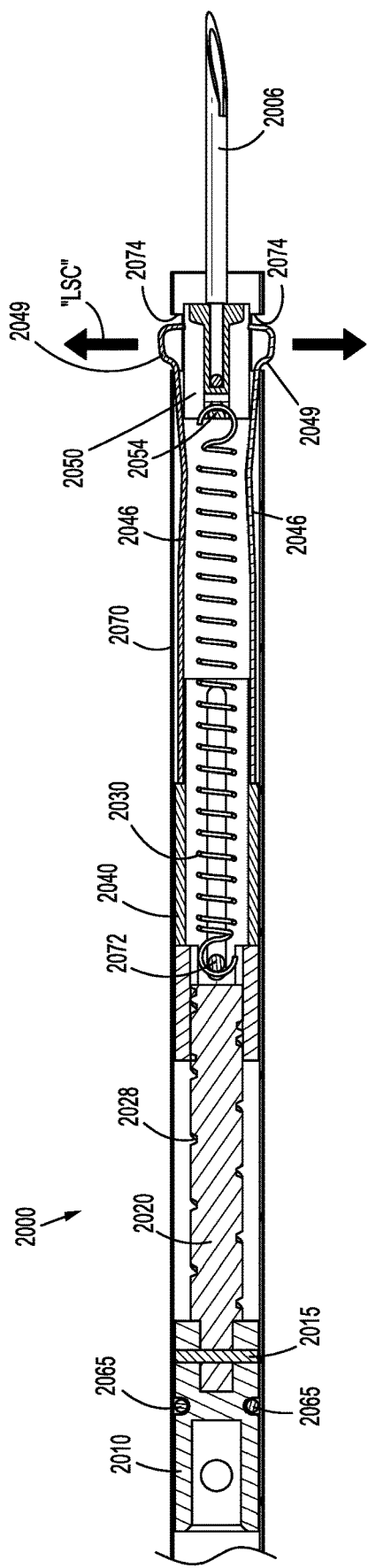
Figure 82:
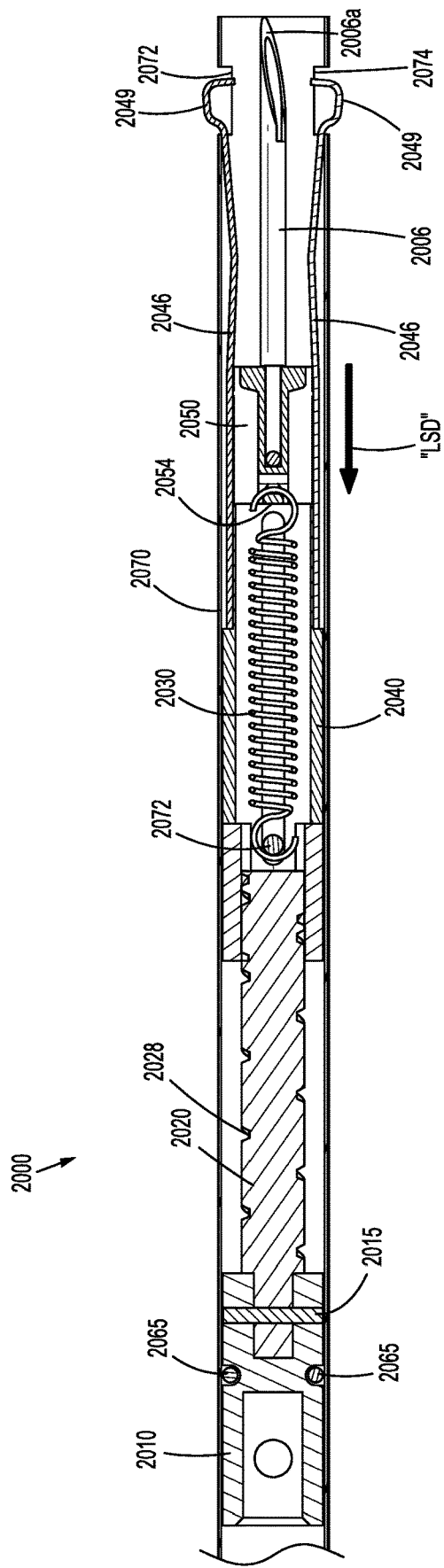
FIG. 82 is a cross-sectional view of the end effector of FIGS. 77-81 illustrating the needle in a retracted position.
Figure 83:
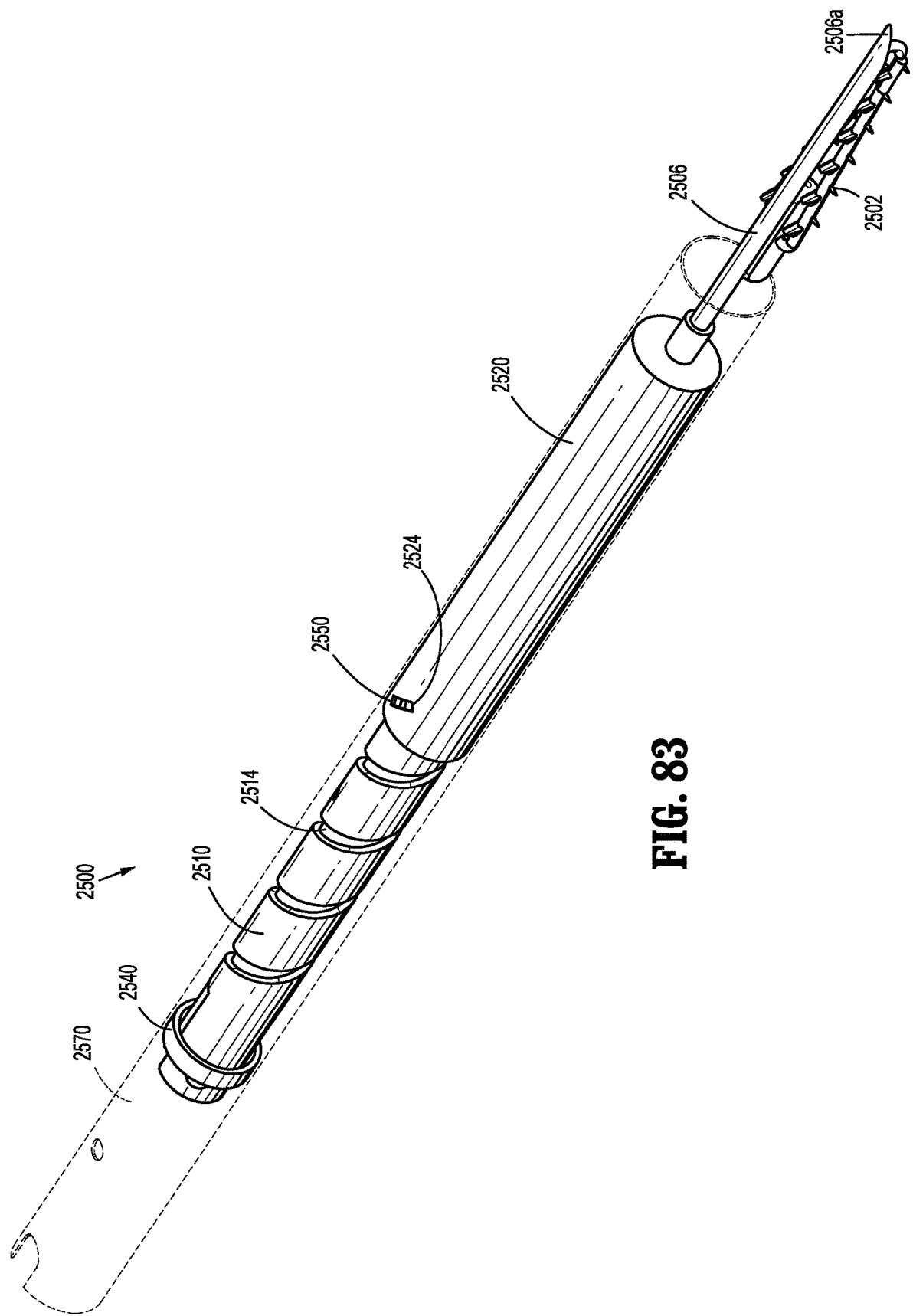
FIG. 83 is a perspective view of an end effector in accordance with embodiments of the present disclosure.

With particular reference to FIGS. 81 and 82, after a predetermined amount of rotation of drive assembly 2010 and distal travel of clip assembly 2040, needle assembly 2050, and needle 2006 (e.g., corresponding to when distal tip 2006a is sufficiently advanced within tissue), fingers 2049 of arms 2046 of clip assembly 2040 are advanced distally until fingers 2049 are axially aligned with apertures 2074 of outer tube 2070. Here, outer tube 2070 no longer resists the radially outward bias of arms 2046, thus permitting arms 2046 to flex radially outward in the direction of "LSC" in FIG. 81 such that fingers 2049 engage apertures 2074, which causes clip assembly 2040, needle assembly 2050, and needle 2006 to stop moving distally with respect to outer tube 2070.

Further, the radially outward movement of arms 2046 causes fingers 2049 to disengage distal lips 2056 of needle assembly 2050. Thus, since the proximal force exerted by retraction spring 2030 is no longer opposed by the engagement between clip assembly 2040 and needle assembly 2050, needle assembly 2050 is able to move proximally in the general direction of arrow "LSD" until needle 2006 reaches the approximate position shown in FIG. 82.

It is envisioned that end effector 2000 can be used more than once. After its initial use, as described above, a user can manually pull needle 2006, and thus needle assembly 2050, distally (e.g., using a pliers-like tool) until distal lips 2056 of needle assembly 2050 are disposed distally fingers 2049. In this position, while needle 2006 is being maintained in its longitudinal position, a user can manually move arms fingers 2049 of clip assembly 2040 radially inwardly by exerting an appropriate force (e.g., through apertures 2074) on fingers 2049 to cause each finger 2049 to engage a distal lip 2056. Here, the proximal force exerted by retraction spring 2030 causes both needle 2006, needle assembly 2050 and clip assembly 2040 to move proximally to their initial positions such that end effector 2000 can be used again to advance needle 2006.

Helix Drive Drop Tab

Referring now to FIGS. 83-90, an embodiment of an end effector 2500 is shown. End effector 2500 is configured for use in connection with surgical device 100. Generally, end effector 2500 is configured to advance a needle 2506 towards tissue and to eject a barbed suture 2502 towards tissue. While FIGS. 83-90 illustrate a particular type of barbed suture 2502 and a particular type of needle 2506, end effector 2500 may be used with different types of sutures and/or needles.

Figure 84:
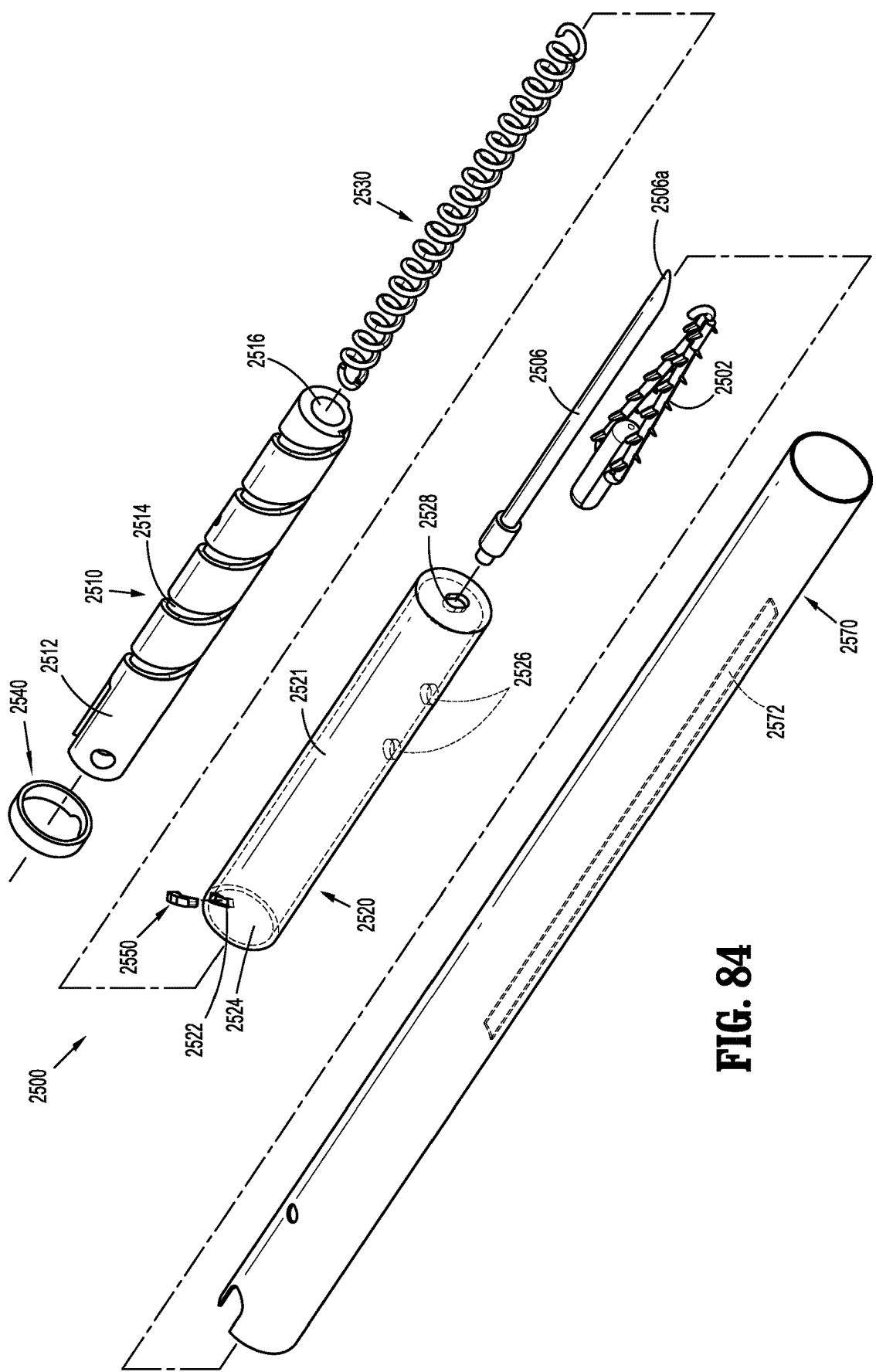
FIG. 84 is an assembly view of the end effector of FIG. 83.

With particular reference to FIG. 84, end effector 2500 includes a drive assembly or drive shaft 2510, a driver 2520, a retraction spring 2530, a proximal ring 2540, a tab 2550, and an outer tube 2570.

Drive shaft 2510 of end effector 2500 is mechanically engaged (e.g., operatively coupled, directly affixed, etc.) to drive rod 150 of surgical device 100 of the present disclosure. Rotation of the drive rod assembly in the general direction of arrow "HDA" in FIG. 85 results in a corresponding rotation of drive shaft 2510. Drive shaft 2510 includes a proximal hub 2512, a helical groove 2514, and defines a cavity 2516 defined within a distal end of drive shaft 2510 and extending proximally through at least a portion of a length of drive shaft 2510 (see FIGS. 85 and 86, for example). Helical groove 2514 of drive shaft 2510 is configured to engage tab 2550, such that rotation of drive shaft 2510 causes tab 2550 to travel at least partially along helical groove 2514. Cavity 2516 of drive shaft 2510 is configured to receive at least a portion of retraction spring 2530 therein.

Driver 2520 of end effector 2500 is a generally hollow cylinder and is configured to be positioned radially outward of at least portions of drive shaft 2520. Driver 2520 includes a body portion 2521, a slot 2522 disposed adjacent a proximal end of body portion 2521 and extending at least partially through a wall of body portion 2521, a proximal aperture 2524, bosses 2526, and a distal aperture 2528. Slot 2522 of driver 2520 is arcuate-shaped in a manner that substantially matches a section of helical groove 2514 of drive shaft 2510. Slot is 2522 is configured to releasably retain a portion of tab 2550 therein. Proximal aperture 2524 of driver 2520 is configured to allow drive shaft 2520 and retraction spring 2530 to pass at least partially therethrough. Bosses 2526 of driver 2520 extend radially outward from body portion 2521 and are configured to slidingly engage a longitudinal slot 2572 of outer tube 2570. The engagement between bosses 2526 and longitudinal slot 2572 helps facilitate and guide longitudinal movement of driver 2520 with respect to outer tube 2570, which helping to restrict the rotational movement of driver 2520 with respect to outer tube 2570. While two bosses 2526 are illustrated, more or fewer bosses 2526 may be utilized. Distal aperture 2528 of driver 2520 is configured to engage a proximal portion of needle 2506.

A proximal portion of retraction spring 2530 of end effector 2500 extends through cavity 2516 and is mechanically engaged with drive shaft 2510. A distal portion of retraction spring 2530 is engaged with (e.g., hooked on) a proximal end of needle 2506 and/or driver 2520. Retraction spring 2530 is configured to bias needle 2506 proximally with respect to outer tube 2570.

Proximal ring 2540 of end effector 2500 is disposed about a proximal end of drive shaft 2510 and is configured to facilitate rotation between drive shaft 2510 and outer tube 2570.

Outer tube 2570 of end effector 2500 is configured for positioning radially outward of at least portions of barbed suture 2502, needle 2506, drive shaft 2510, driver 2520, retraction spring 2530, and proximal ring 2540. Outer tube 2570 includes longitudinal slot 2572 configured to slidingly receive bosses 2526 of driver 2520.

Figure 85:
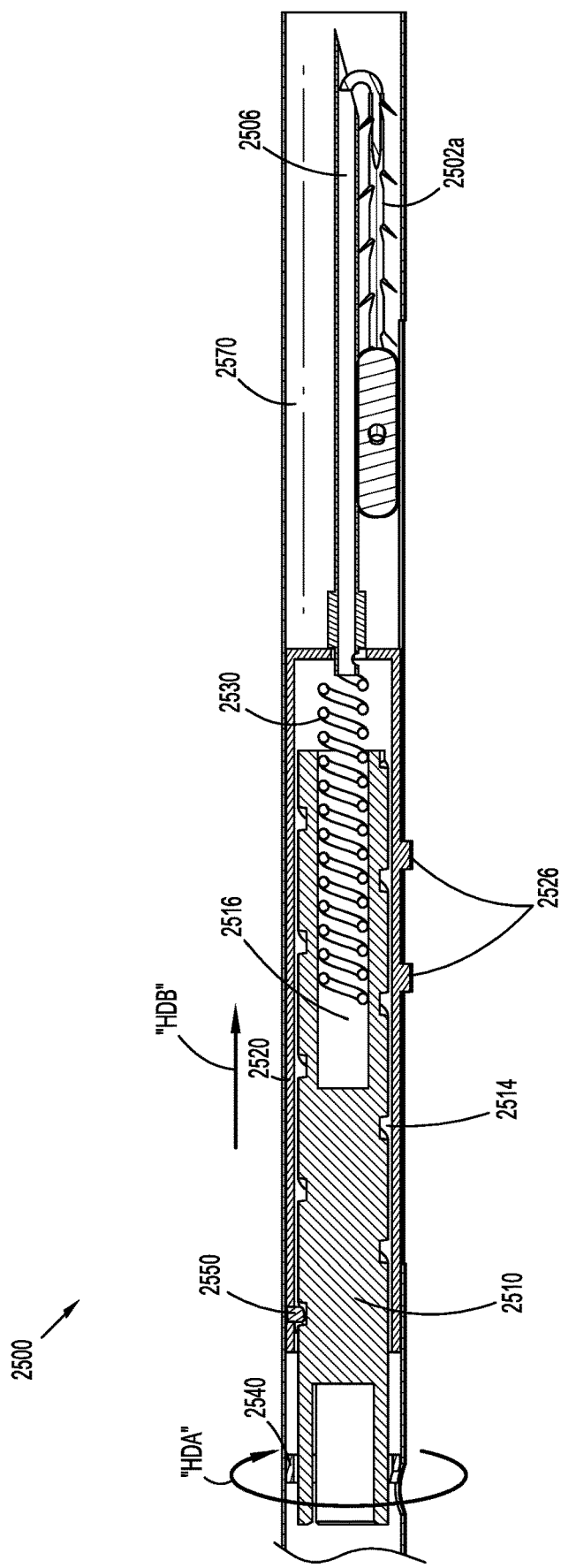
FIG. 85 is a cross-sectional view of the end effector of FIGS. 83-84.

In use, in response to at least a partial actuation of the trigger of surgical device 100, drive rod 150 rotates, as discussed above. With reference to FIGS. 85-87, initial rotation of the drive rod 150 results in a corresponding rotation of drive shaft 2510 with respect to outer tube 2570 in the general direction of arrow "HDA" in FIG. 85. Due to the engagement between helical groove 2514 of drive shaft 2510 and tab 2550, rotation of drive shaft 2510 in the general direction of arrow "HDA" results in distal translation of tab 2550 within helical groove 2514 and with respect to drive shaft 2510. Since tab 2550 is non-rotatably engaged with driver 2520, and since driver 2520 is rotatably fixed with respect to outer tube 2570 due to the engagement between bosses 2526 and longitudinal slot 2572, the distal translation of tab 2550 results in distal translation of driver 2520 with respect to outer tube 2570 toward the position shown in FIGS. 86 and 87, for example. The engagement between tab 2550, drive shaft 2510 and driver 2520 opposes the proximal force exerted by retraction spring 2530.

Continued rotation of drive shaft 2510 in the general direction of arrow "HDA" causes continued distal advancement of tab 2550, driver 2520, needle 2506 and barbed suture 2502 until a distal tip 2506a of needle 2506 extends a sufficient distance distally beyond a distal end of outer tube 2570. Thus, to insert needle 2506 into tissue, a distal end of end effector 2500 is positioned adjacent or in contact with tissue, and the trigger of surgical device 100 is at least partially actuated, thus distally advancing a portion of needle 2506 and/or barbed suture 2502 into tissue.

Figure 88:
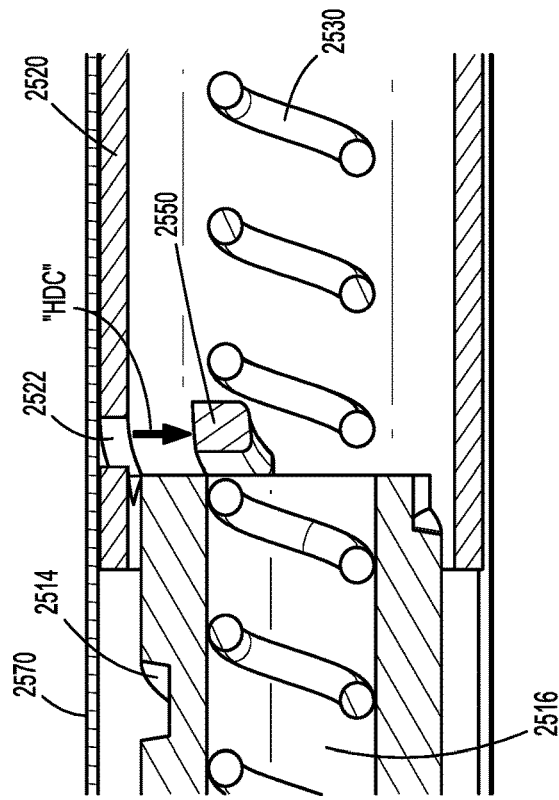
FIG. 88 is a perspective view of portions of the end effector of FIGS. 83-87.
Figure 89:
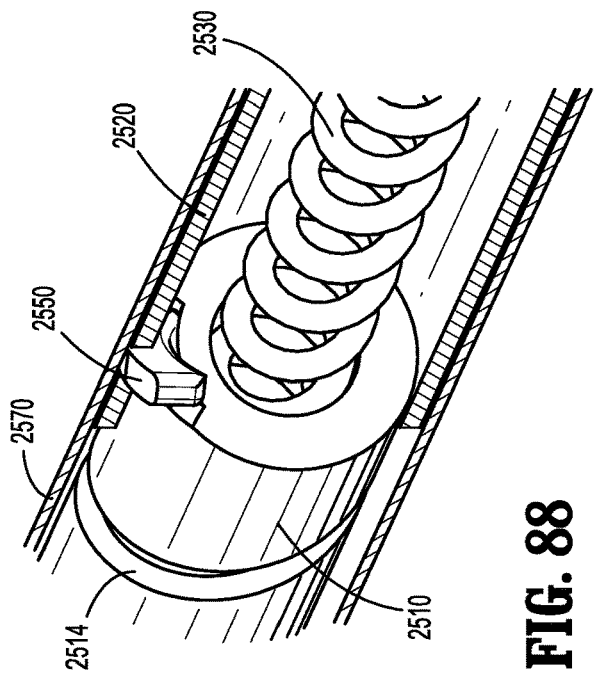
FIG. 89 is a cross-sectional view of portions of the end effector of FIGS. 83-88.
Figure 90:
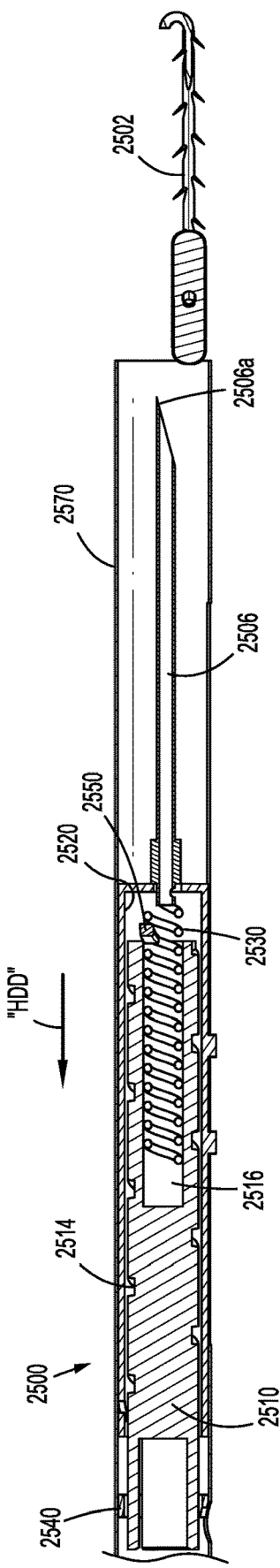
FIG. 90 is a cross-sectional view of the end effector of FIGS. 83-89 illustrating a barbed suture ejected therefrom.

With particular reference to FIGS. 88-90, after a predetermined amount of rotation of drive shaft 2510 and distal travel of tab 2550, driver 2520, needle 2506 and/or barbed suture 2502 (e.g., corresponding to when distal tip 2506a of needle 2506 is sufficiently advanced within tissue), tab 2550 has travelled through a distal-most end of helical groove 2514 and is located distally beyond a distal edge of driver 2510. Here, as shown in FIG. 89, driver 2510 is no longer restricting the movement of tab 2550. This results in tab 2550 moving radially inward of walls of driver 2510 (e.g., due to gravity or biased out of thread) in the general direction of arrow "HDC" and thus out of engagement with driver 2510. Here, tab 2550 is no longer helping to resist the proximal forced exerted by retraction spring 2530.

Thus, since the proximal force exerted by retraction spring 2530 is no longer opposed by the engagement between tab 2550, drive shaft 2510 and driver 2520, needle 2506 is able to move proximally in the general direction of arrow "HDD" until needle 2506 reaches the approximate position shown in FIG. 90. As shown, barbed suture 2502 remains external of end effector 2500 (e.g., at least partially within tissue).

Spring Return "C"

Referring now to FIGS. 91-98, an embodiment of an end effector 2600 is shown. End effector 2600 is configured for use in connection with surgical device 100. Generally, end effector 2600 is configured to advance a needle 2606 towards tissue and to eject a barbed suture (not explicitly shown) towards tissue. While FIGS. 91-98 illustrate a particular type of needle 2606, end effector 2600 may be used with different types of needles.

Figure 92:
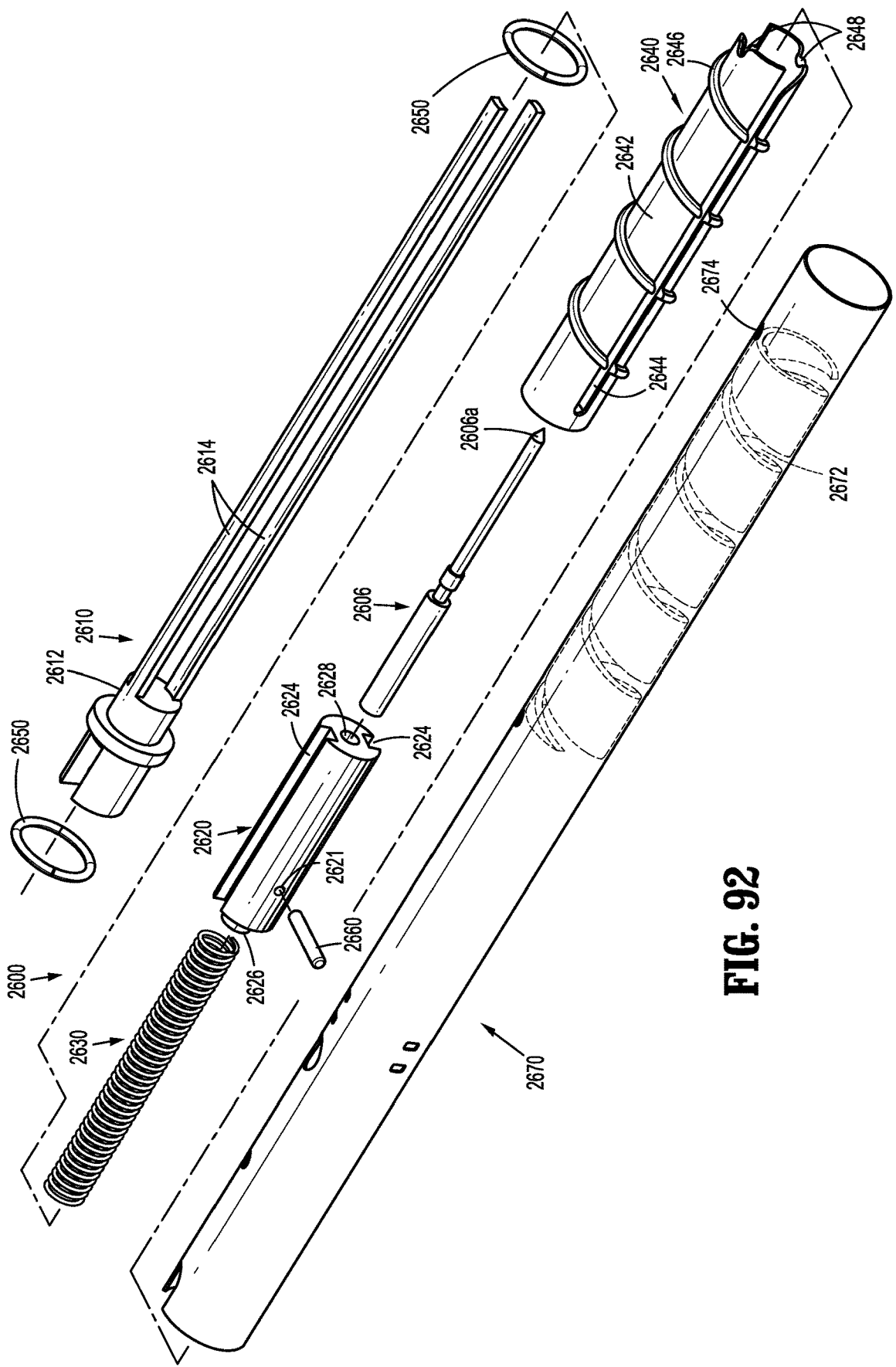
FIG. 92 is an assembly view of the end effector of FIG. 91.

With particular reference to FIG. 92, end effector 2600 includes a drive assembly 2610, a needle assembly or needle block 2620, a retraction spring 2630, a driver 2640, a pair of rings 2650, and an outer tube 2670.

Drive assembly 2610 of end effector 2600 is mechanically engaged (e.g., operatively coupled, directly affixed, etc.) to drive rod 150 of surgical device 100 of the present disclosure. Rotation of the drive rod 150 in the general direction of arrow "SRCA" in FIG. 91 results in a corresponding rotation of drive assembly 2610. Drive assembly 2610 includes a body portion 2612 and a pair of arms 2614 extending therefrom. Arms 2614 of drive assembly 2610 are configured to slidingly receive portions of needle block 2620.

Needle block 2620 of end effector 2600 includes a body portion 2622 having a pair of longitudinal slots 2624. Each longitudinal slot 2624 is configured to slidingly receive one arm 2614 of drive assembly 2610 therein. Accordingly, needle block 2620 is longitudinally translatable with respect to drive assembly 2610. Additionally, the engagement between arms 2614 of drive assembly 2610 and longitudinal slots 2624 of needle block 2620 causes needle block 2620 to rotate in a corresponding manner as drive assembly 2610. Needle block 2620 also includes a proximal portion 2626 configured to engage a distal portion of retraction spring 2630, and defines an aperture 2628 configured to engage a portion of needle 2606. It is envisioned that needle block 2620 is neither rotatable nor longitudinally translatable with respect to needle 2606 due to the engagement therebetween.

A pin 2660 of end effector 2600 extends through an aperture 2621 of needle block 2620. Pin 2660 is wider or longer than a width of needle block 2620 such that pin 2660 extends laterally beyond walls of needle block 2620. Further, pin 2660 is positioned such that pin 2660 extends laterally beyond both walls of needle block 2620 to engage portions of driver 2640, as discussed below. Additionally, pin 2660 is positioned proximally of needle 2606, and may be positioned in contact with needle 2606.

Driver 2640 of end effector 2600 is generally hollow and includes a body portion 2642, a pair of longitudinal slots 2644 extending along a majority of a length of body portion 2642, a threaded portion or helix portion 2646 extending radially outward from body portion 2642, and a distal guide 2648. Distal guide 2648 of driver 2640 includes arcuate portions configured to releasably receive portions of pin 2660. Pin 2660 is positioned in contact with distal guide 2648 in such a manner that rotation of pin 2660 causes rotation of driver helix 2648. Additionally, longitudinal slots 2644 of driver 2640 are configured to allow pin 2660 to longitudinally travel therethrough. Helix portion 2646 of driver 2640 is configured to engage a threaded portion or helical recess 2672 disposed in outer tube 2670, such that driver 2640 is rotatable with respect to outer tube 2670.

A proximal portion of retraction spring 2630 of end effector 2600 is mechanically engaged with drive assembly 2610, and a distal portion of retraction spring 2630 is mechanically engaged with proximal portion 2626 of needle block 2620. Retraction spring 2630 is configured to proximally bias needle block 2620, and thus needle 2606, with respect to outer tube 2670.

Outer tube 2670 of end effector 2600 is configured for positioning radially outward of at least portions of needle 2606, drive assembly 2610, needle block 2620, retraction spring 2630, and driver 2640. Outer tube 2670 includes helical recess 2672 defined therein, which is configured to rotationally engage helix portion 2646 of driver 2640. Driver 2640 is configured to longitudinally translatable with respect to outer tube 2670 in response to rotation of driver 2640 with respect to outer tube 2670. That is, as driver 2640 rotates with respect to outer tube 2670, the engagement between helix portion 2646 and helical recess 2672 cause driver 2640 to rotate. Additionally, the engagement between distal guide 2648 and pin 2660 resists the proximal force exerted by retraction spring 2630. Outer tube 2670 also includes a stop 2674 extending radially inward from a distal portion thereof. Stop 2674 is configured to selectively engage pin 2660, as discussed below.

Rings 2650 (e.g., O-rings) of end effector 2600 are positioned radially outward of a proximal portion of drive assembly 2610. Rings 2650 help maintain appropriate spacing between drive assembly 2610 and outer tube 2670, and help facilitate rotation of drive assembly 2610 with respect to outer tube 2670.

Figure 91:
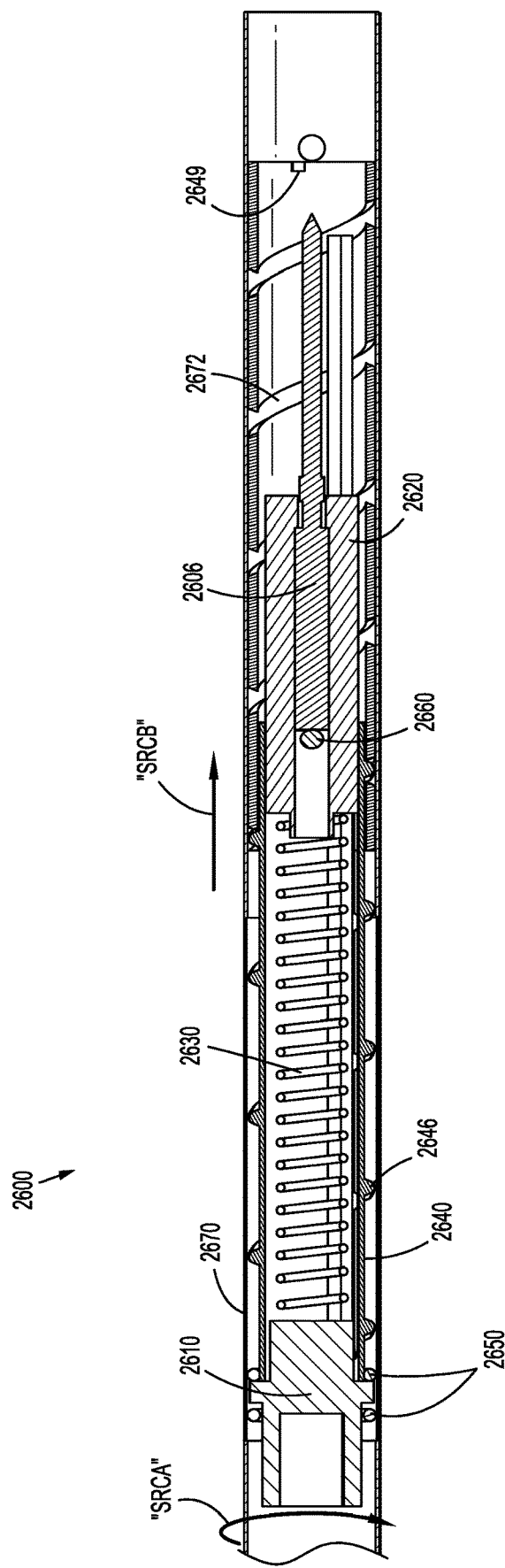
FIG. 91 is a cross-sectional view of an end effector in accordance with embodiments of the present disclosure.

In use, in response to at least a partial actuation of the trigger of surgical device 100, drive rod 150 rotates, as discussed above. With reference to FIG. 91, initial rotation of the drive rod 150 results in a corresponding rotation of drive assembly 2610 with respect to outer tube 2670 in the general direction of arrow "SRCA" in FIG. 91. Due to the engagement between arms 2614 of drive assembly 2610 and longitudinal slots 2624 of needle block 2620, rotation of drive assembly 2610 in the general direction of arrow "SRCA" results in a corresponding rotation of needle block 2620. Due to the engagement between pin 2660 and needle block 2620, and between pin 2660 and distal guide 2648 of driver 2640, rotation of needle block 2620 results in a corresponding rotation of driver 2640 with respect to outer tube 2670.

Further, as driver 2640 rotates with respect to outer tube 2670, the engagement between helix portion 2646 and helical recess 2672 of outer tube 2670 causes driver 2640 to distally translate with respect to outer tube 2670 in the general direction of arrow "SRCB" in FIG. 91. Due to the engagement between driver 2640 and needle block 2620 via pin 2660, distal translation of driver 2640 results in a corresponding distal translation of needle block 2620 and needle 2606.

Figure 94:
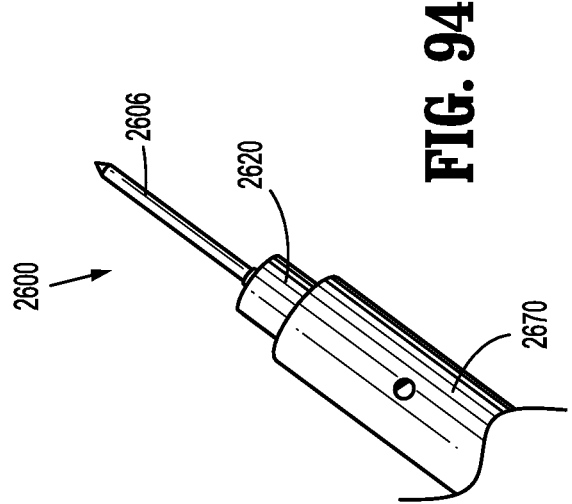
FIGS. 94 and 95 are perspective views of portions of the end effector of FIGS. 91-93.
Figure 95:
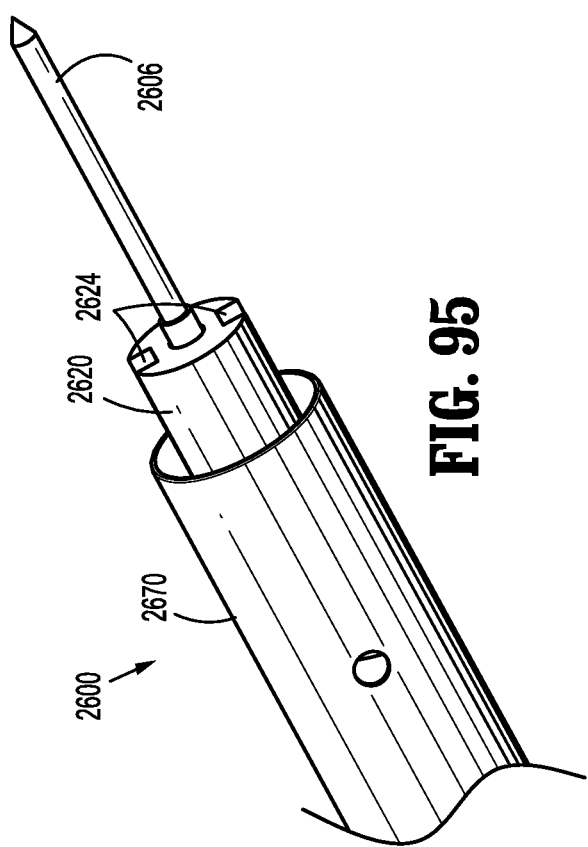
Figure 96:
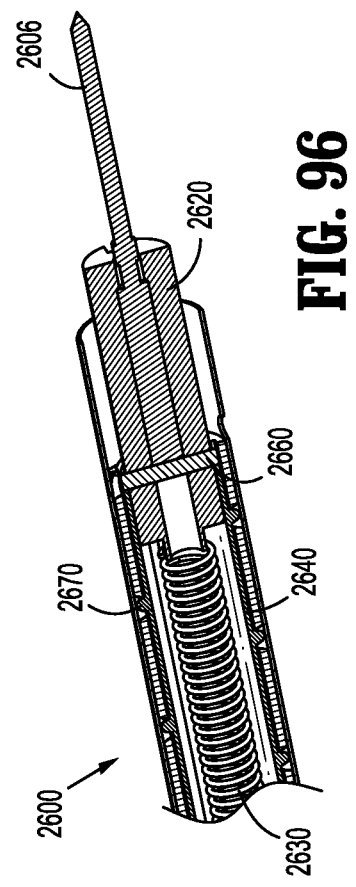
FIG. 96 is a cross-sectional view of portions of the end effector of FIGS. 91-95.
Figure 99:
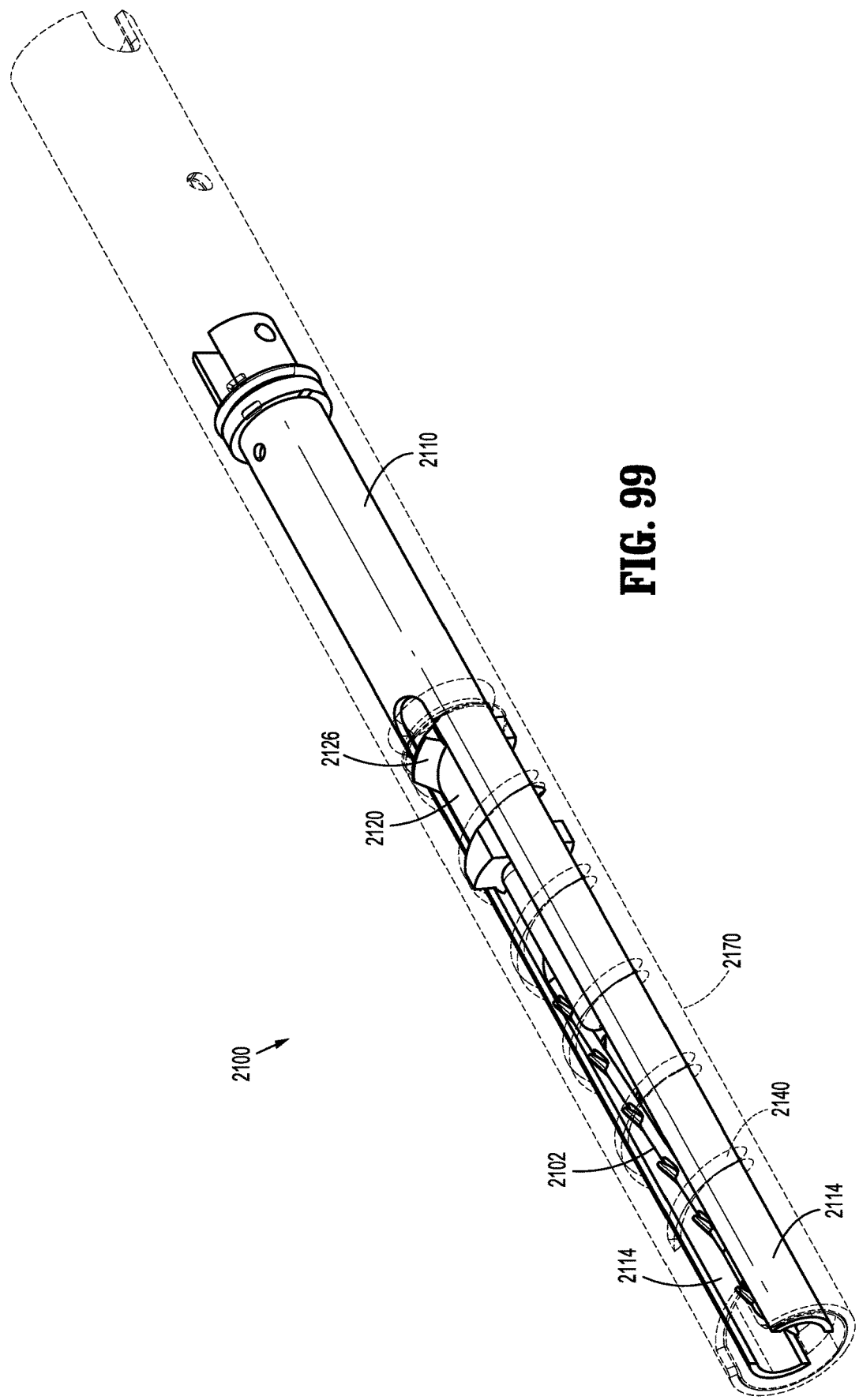
FIG. 99 is a perspective view of an end effector in accordance with embodiments of the present disclosure.

Continued rotation of drive assembly 2610 in the general direction of arrow "SRCA" causes continued distal advancement of needle block 2620 and needle 2606 until a distal tip 2606b of needle 2606 extends a sufficient distance distally beyond a distal end of outer tube 2670 as shown in FIGS. 94-96, for example. Thus, to insert needle 2606 and/or a barbed suture into tissue, a distal end of end effector 2600 is positioned adjacent or in contact with tissue, and the trigger of surgical device 100 is at least partially actuated, thus distally advancing a portion of needle 2606 and/or barbed suture into tissue.

Figure 93:
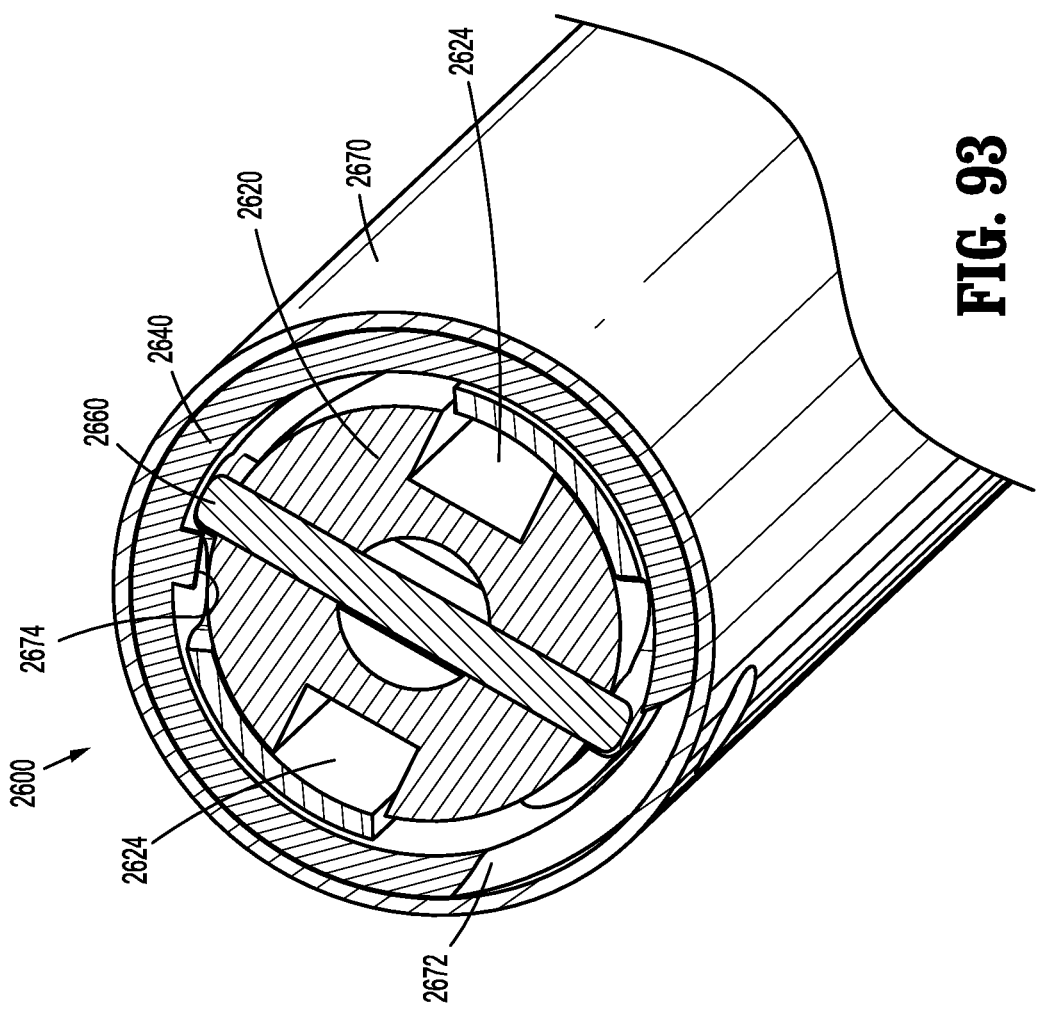
FIG. 93 is a cut-away view of the end effector of FIGS. 91-92.

With particular reference to FIG. 93, after a predetermined amount of rotation of drive assembly 2610 and distal travel of needle 2606 (e.g., corresponding to when distal tip 2606b is sufficiently advanced within tissue), pin 2660 contacts stop 2674 of outer tube 2670. In connection with rotation of needle block 2620, the contact between pin 2660 and stop 2674 of outer tube 2670 causes pin driver 2640 to rotate with respect to pin 2660 such that pin 2660 moves out of engagement with distal guide 2648 until pin 2660 is rotationally aligned with longitudinal slots 2644 of driver 2640.

In this position, the engagement between pin 2660 and distal guide 2648 is no longer resisting the proximal bias provided by retraction spring 2630, and pin 2660 is able to proximally translate through longitudinal slots 2644. Accordingly, retraction spring 2630 pulls needle block 2620, pin 2660 and needle 2606 proximally with respect to outer tube 2670 in the general direction of arrow "SRCC" in FIG. 97.

Spring Return "B"

Referring now to FIGS. 99-103, an embodiment of an end effector 2100 is shown. End effector 2100 is configured for use in connection with surgical device 100. Generally, end effector 2100 is configured to advance a needle 2106 towards tissue and to eject a barbed suture 2102 towards tissue. While FIGS. 99-103 illustrate a particular type of barbed suture 2102 and a particular type of needle 2106, end effector 2100 may be used with different types of sutures and/or needles.

Figure 100:
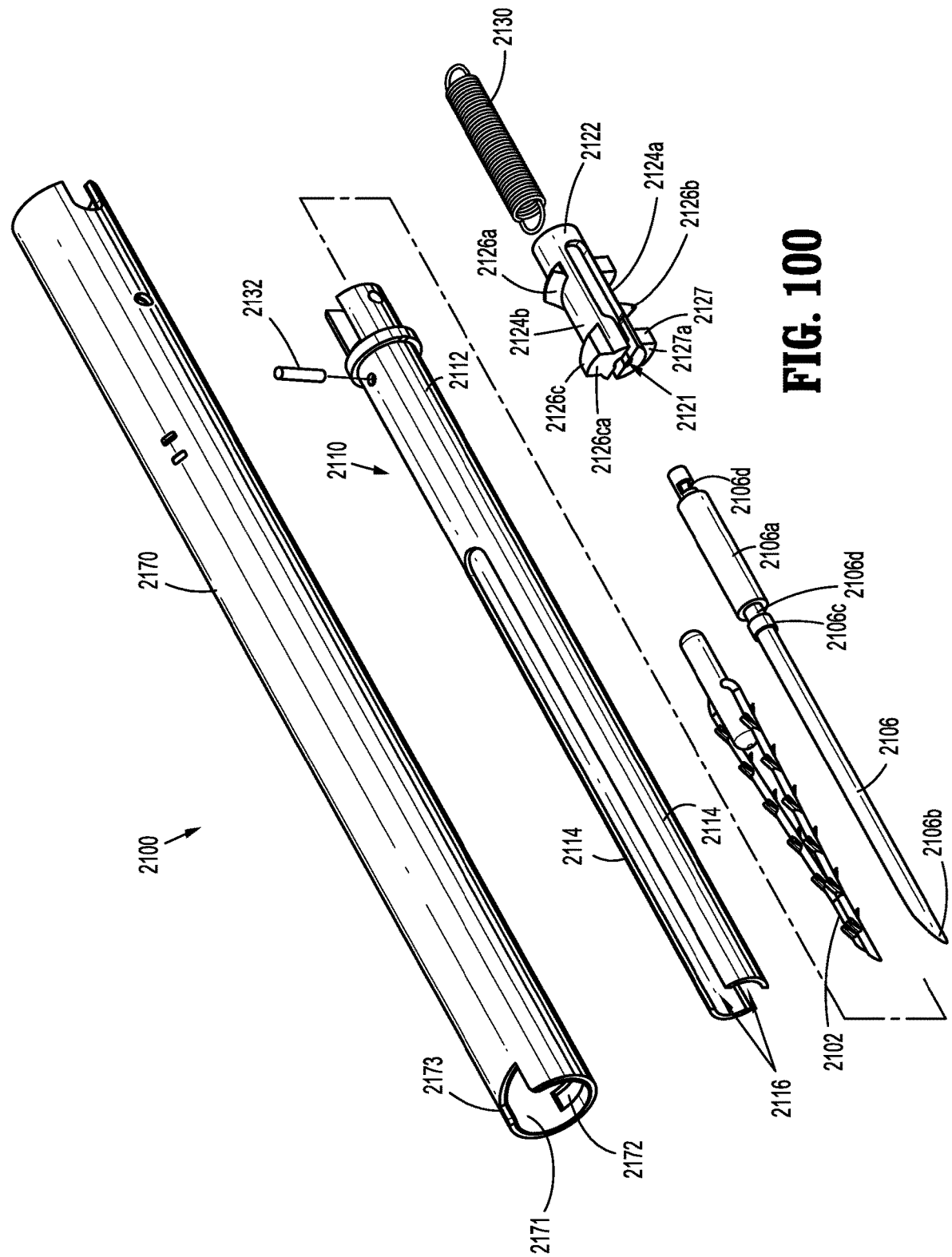
FIG. 100 is an assembly view of the end effector of FIG. 99.

With particular reference to FIG. 100, end effector 2100 includes a drive assembly 2110, a driver 2120, a retraction spring 2130, and an outer tube 2170.

Drive assembly 2110 of end effector 2100 is mechanically engaged (e.g., operatively coupled, directly affixed, etc.) to drive rod 150 of surgical device 100 of the present disclosure. Rotation of the drive rod 150 in the general direction of arrow "SBA" in FIG. 102 results in a corresponding rotation of drive assembly 2110. Drive assembly 2110 includes a body portion 2112 and a pair of arms 2114 extending therefrom. Arms 2114 of drive assembly 2110 define a pair of slots 2116 therebetween. Slots 2116 of arms 2114 of drive assembly 2110 are configured to slidingly receive portions of driver 2120.

Needle block or needle 2106 includes a proximal hub 2106a, and a distal tip 2106b configured to pierce tissue. Needle 2106 also includes a lip 2106c disposed distally of proximal hub 2106a. Lip 2106c is configured to engage a portion of driver 2120, as discussed below. Additionally, needle 2106 includes a hook 2016d extending proximally from proximal hub 2106a. Hook 2016d is configured to engage a distal portion of retraction spring 2130, as discussed below.

A distal portion of retraction spring 2130 of end effector 2100 is engaged with hook 2016d of needle 2106, and a proximal portion of retraction spring 2130 is engaged with a pin 2132 extending through an aperture of drive assembly 2110. Retraction spring 2130 is configured to bias needle 2106 proximally.

Driver 2120 of end effector 2100 includes a proximal portion 2122 and a pair of arms 2124 extending distally from proximal portion 2122. Arms 2124 of driver 2120, including a first arm 2124a and a second arm 2124b, are biased radially outwardly in the general direction of arrow "SBB" in FIG. 103. Engagement between arms 2124 and outer tube 2170 prevent arms 2124 from moving radially out of engagement with needle 2106. Driver 2120 defines a cavity 2121 (FIG. 100) therein, which is configured to releasably retain proximal hub 2106a of needle 2106 therein. Driver 2120 further includes a threaded portion including a plurality of threads 2126 extending radially outward from proximal portion 2122 and/or at least one arm 2124. Threads 2126 are configured to engage a threaded portion or outer threads 2140 (e.g., distal edges of outer threads 2140), which extend radially inward from an inner wall 2171 of outer tube 2170. In the illustrated embodiment, driver 2120 includes a first thread 2126a extending radially outward from second arm 2124b, a second thread 2126b extending radially outward from first arm 2124a, and a third thread 2126c extending radially outward from a distal portion of second arm 2124b. Proximal portions of threads 2126 are generally arcuate for engaging with outer threads 2140. A distal face 2126ca of third thread 2126c of driver 2120 is generally perpendicular to needle 2106.

Driver 2120 of end effector 2100 also includes a finger 2127 extending radially outward from the arm that does not include a thread at its distal portion. In the illustrated embodiment, first arm 2124a includes finger 2127. A distal face 2127a of finger 2127 of driver 2120 is generally perpendicular to needle 2106 and generally parallel to distal face 2126ca of third thread 2126c. Distal face 2126ca of third thread 2126c and distal face 2127a of finger 2127 of driver 2120 are each configured to mechanically engage a proximal surface of lip 2106c of needle 2106.

Figure 101:
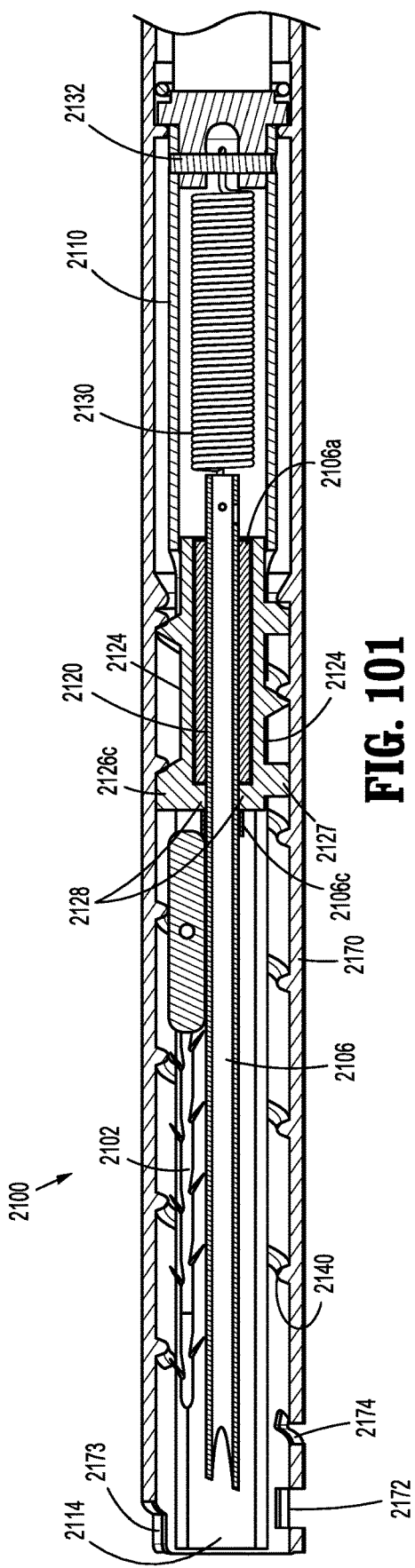
FIG. 101 is a cross-sectional view of the end effector of FIGS. 99-100.

With particular reference to FIG. 101, driver 2120 further includes tabs 2128 disposed adjacent a distal end of each arm 2124. Tabs 2128 extend radially inward from the respective arm 2124, and are each configured to engage a recess 2106d (FIG. 100) of needle 2106. Recess 2106d of needle 2106 is disposed between proximal hub 2106a and lip 2106c of needle 2106.

Figure 102:
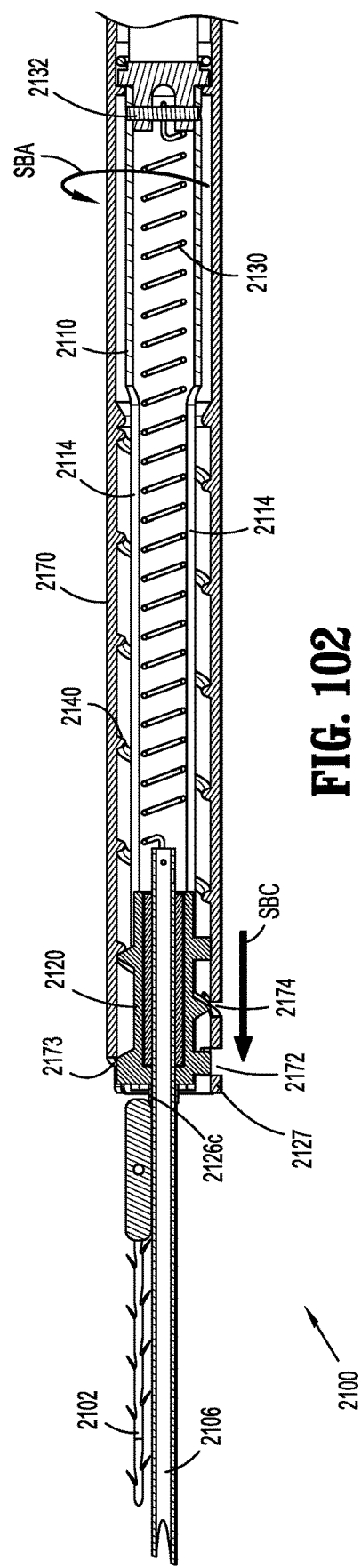
FIG. 102 is a cross-sectional view of the end effector of FIGS. 99-101 illustrating a needle in an advanced position.

Outer tube 2170 of end effector 2100 is configured for positioning radially outward of at least portions of needle 2106, drive assembly 2110, driver 2120, and retraction spring 2130. Outer tube 2170 includes a first aperture 2172 disposed adjacent its distal end, and a second aperture 2174 disposed proximally of first aperture 2172 (see FIGS. 101 and 102). As shown in FIG. 102, first aperture 2172 is configured to engage (e.g., releasably engage) finger 2127 of driver 2120, and second aperture 2174 is configured to engage (e.g., releasably engage) second thread 2126b of driver 2120.

Outer threads 2140 of outer tube 2170 extend radially inward from an inner wall 2171 of outer tube 2170, and are stationary with respect to outer tube 2170. Outer threads 2140 are configured to engage a portion of driver 2120 such that driver 2120 can move longitudinally and rotationally within outer tube 2170 and with respect to outer tube 2170.

Figure 103:
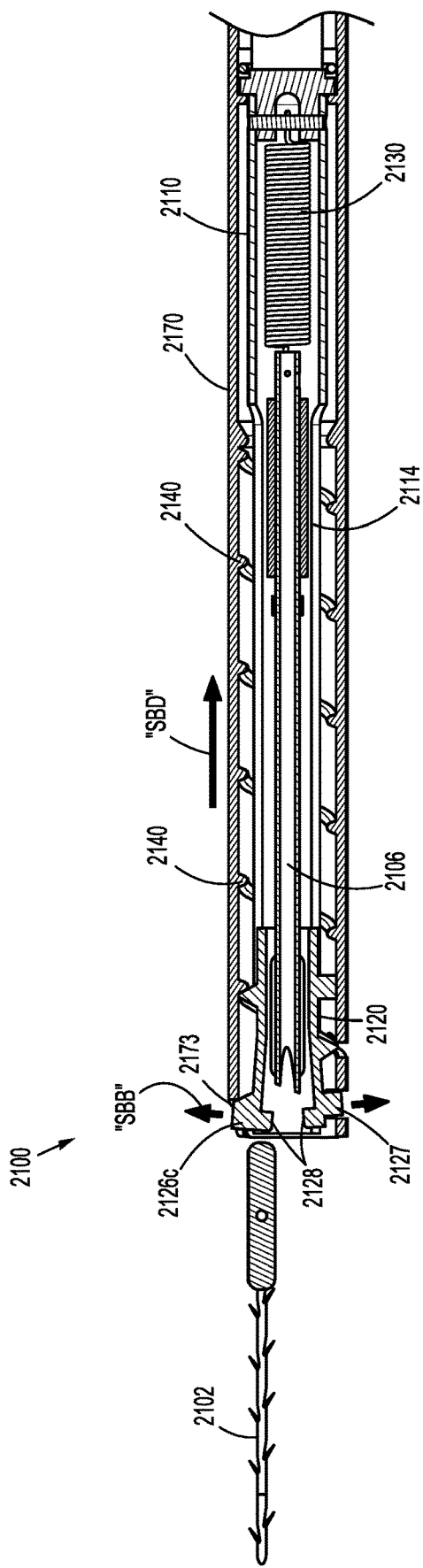
FIG. 103 is a cross-sectional view of the end effector of FIGS. 99-102 illustrating the needle in a retracted position and a barbed suture ejected from the end effector.

In use, in response to at least a partial actuation of the trigger of surgical device 100, drive rod 150 rotates, as discussed above. With reference to FIGS. 102-103, initial rotation of the drive rod 150 results in a corresponding rotation of drive assembly 2110 and driver 2120 with respect to outer tube 2170 in the general direction of arrow "SBA" in FIG. 102. Due to the engagement between outer threads 2140 and fingers 2126 of driver 2120, rotation of driver 2120 in the general direction of arrow "SBA" results in a corresponding rotation and distal translation of driver 2120 with respect to outer tube 2170 in the general direction of arrow "SBC" in FIG. 102. Distal translation of driver 2120 causes a corresponding distal translation of needle 2106. Further, distal translation of driver 2120 also causes a corresponding distal translation of barbed suture 2102 due to the engagement between barbed suture 2102 and distal face 2126ca of third thread 2126c and distal face 2127a of finger 2127.

Continued rotation of drive assembly 2110 in the general direction of arrow "SBA" causes continued distal advancement of driver 2120 and needle 2106 until distal tip 2106b of needle 2106 extends a sufficient distance distally beyond a distal end of outer tube 2170. Thus, to insert needle 2106 and/or barbed suture 2102 into tissue, a distal end of end effector 2100 is positioned adjacent or in contact with tissue, and the trigger of surgical device 100 is at least partially actuated, thus distally advancing a portion of needle 2106 and/or barbed suture 2102 into tissue.

With particular reference to FIG. 103, after a predetermined amount of rotation of drive assembly 2110 and distal travel of needle 2106 (e.g., corresponding to when distal tip 2106b is sufficiently advanced within tissue), fingers 2126 of driver 2120 are advanced distally beyond outer threads 2140. In this position, finger 2127 and second thread 2126b of driver 2120 are axially aligned with first aperture 2172 and second aperture 2174, respectively, of outer tube 2170. Here, outer tube 2170 no longer resists the radially outward bias of arms 2124 of driver 2120, thus permitting arms 2124 to flex radially outward in the direction of "SBB" in FIG. 103 such that finger 2127 engages first aperture 2172, and third thread 2126c engages a distal notch 2173 of outer tube 2170.

Further, the radially outward movement of arms 2124 causes tabs 2128 of driver 2120 to disengage recess 2106d of needle 2106. Thus, since the proximal force exerted by retraction spring 2130 is no longer opposed by the engagement between driver 2120 and needle 2103, needle 2103 is able to move proximally in the general direction of arrow "SBD" until needle 2106 reaches the approximate position shown in FIG. 103. Since driver 2120 is engaged with first aperture 2172 and distal notch 2173 of outer tube 2170 and is no longer mechanically engaged with needle 2106, the proximal movement of needle 2106 causes at least a portion of needle 2106 to move through cavity 2121 of driver 2120, while driver 2120 remains adjacent a distal portion of outer tube 2170, as shown in FIG. 103.

It is envisioned that end effector 2100 can be used more than once. After its initial use, as described above, a user can manually pull needle 2106 distally (e.g., using a pliers-like tool) until recess 2106d of needle 2106 is axially aligned with tabs 2128 of driver 2120. In this position, while needle 2106 is being maintained in its longitudinal position, a user can manually move arms 2124 of driver 2120 radially inwardly by exerting an appropriate force (e.g., through first aperture 2172 and distal notch 2173) on third thread 2126c and finger 2127 to cause tabs 2128 to engage recess 2106d. Here, the proximal force exerted by retraction spring 2130 causes both needle 2106 and driver 2120 to move proximally to their initial positions such that end effector 2100 can be used again to advance needle 2106. Additionally, if a user wishes to use another barbed suture 2102, needle 2106 can be pulled farther proximally to allow an additional barbed suture 2102 to engage needle 2106 prior to driver 2120 re-engaging needle 2106.

While some embodiments of end effectors described herein have been described as being re-usable, it is contemplated that any of the end effectors described herein are configured for release, reloading and/or reuse.

In accordance with the present disclosure, it is contemplated that an electromechanical control module may replace handle assembly 110 to actuate the surgical device 100. The electromechanical control module may include at least one microprocessor, at least one drive motor controllable by the at least one microprocessor, and a source of power for energizing the at least one microprocessor and the at least one drive motor.

As can be appreciated, securement of any of the components of the presently disclosed devices can be effectuated using known fastening techniques such welding, crimping, gluing, etc.

Additionally, the present disclosure includes methods of using the disclosed end effectors, and methods of performing a surgical procedure utilizing the disclosed end effectors. An example of a disclosed method includes using a disclosed end effector to advance stay-sutures (e.g., four stay-sutures) through an implant (e.g., mesh) to hold the implant in a desired position, removing the end effector from the handle portion of a surgical instrument, engaging a second end effector with the same handle portion of the surgical instrument used to advance stay-sutures through the implant, and advancing tacks from the second end effector through the implant.

The present disclosure also includes surgical systems. A disclosed surgical system includes a surgical device, a first end effector and a second end effector. The surgical device includes a handle assembly and an elongated portion extending distally from the handle assembly. The first end effector is configured to releasably engage a distal portion of the elongated portion, and includes a drive assembly and a needle assembly. The drive assembly is configured to advance and retract the needle assembly upon at least a partial actuation of the handle assembly of the surgical device. The second end effector is configured to releasably engage the distal portion of the elongated portion, includes a plurality of tacks therein, and is configured to distally advance the plurality of tacks upon at least a partial actuation of the handle assembly of the surgical device.

The present disclosure also includes surgical kits including a plurality of first end effectors (e.g., pre-loaded with stay-sutures, barbed sutures, etc.), a plurality of second end effectors (e.g., pre-loaded with a plurality of tacks), and a surgical device. The surgical device includes a handle assembly and an elongated portion extending distally from the handle assembly. Each of the first end effectors and second end effectors is configured to releasably engage a distal portion of the elongated portion of the surgical device.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the surgical instruments disclosed herein while another surgeon (or group of surgeons) remotely controls the instrument(s) via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. An end effector for use with a surgical device, the end effector comprising:
a drive shaft defining a longitudinal axis and including a helical groove;
a driver having a slot, at least a portion of the driver positioned radially outward of the drive shaft;
a tab engaged with the slot of the driver and with the helical groove of the drive shaft;
an outer tube, at least a portion of the outer tube positioned radially outward of the driver; and
a needle engaged with a distal portion of the driver,
wherein rotation of the drive shaft about the longitudinal axis causes the tab to travel along the helical groove, and causes the driver to longitudinally translate relative to the outer tube.

2. The end effector according to claim 1, further including a biasing element configured to bias the needle proximally relative to the outer tube.

3. The end effector according to claim 2, wherein a proximal portion of the biasing element is mechanically engaged with the drive shaft.

4. The end effector according to claim 3, wherein a distal portion of the biasing element is mechanically engaged with at least one of the needle or the driver.

5. The end effector according to claim 2, wherein engagement between the tab and the drive shaft opposes a proximal force exerted by the biasing element.

6. The end effector according to claim 1, wherein the tab is arcuate.

7. The end effector according to claim 6, wherein the slot of the driver is arcuate.

8. The end effector according to claim 1, wherein a predetermined amount of rotation of the drive shaft about the longitudinal axis causes the tab to disengage from the helical groove of the drive shaft.

9. The end effector according to claim 1, wherein a predetermined amount of rotation of the drive shaft about the longitudinal axis causes the tab to disengage from the slot of the driver.

10. The end effector according to claim 1, wherein the tab is selectively engaged with the slot of the driver and with the helical groove of the drive shaft.

11. The end effector according to claim 1, wherein the driver includes at least one boss, and the outer tube includes a longitudinal slot, the at least one boss configured to longitudinally translate at least partially within the longitudinal slot.

12. The end effector according to claim 1, wherein the driver is rotationally fixed relative to the outer tube.

13. The end effector according to claim 12, wherein the drive shaft is longitudinally fixed relative to the outer tube.

14. An end effector for use with a surgical device, the end effector comprising:
a drive shaft defining a longitudinal axis and including a groove;
a driver having a slot; and a tab selectively engaged with the slot of the driver and with the groove of the drive shaft;

wherein a first amount rotation of the drive shaft about the longitudinal axis causes the tab to travel along the groove, and wherein a second amount rotation of the drive shaft about the longitudinal axis causes the tab to disengage from the groove.

15. The end effector according to claim 14, further including a needle engaged with a distal portion of the driver, and a biasing element configured to bias the needle proximally relative to the drive shaft.

16. The end effector according to claim 15, wherein disengagement of the tab from the groove causes the needle to move proximally relative to the drive shaft.

17. The end effector according to claim 14, further including an outer tube including a longitudinal slot, wherein the driver includes at least one boss configured to longitudinally translate at least partially within the longitudinal slot.

18. The end effector according to claim 17, wherein the first amount of rotation of the drive shaft about the longitudinal axis causes the driver to longitudinally translate relative to the outer tube.

19. The end effector according to claim 14, wherein the groove of the drive shaft is helical, and the tab is arcuate.

20. The end effector according to claim 14, wherein the second amount rotation of the drive shaft about the longitudinal axis causes the tab to disengage from the slot.

* * * * *